(12) United States Patent
Massingham

(10) Patent No.: US 12,264,360 B2
(45) Date of Patent: Apr. 1, 2025

(54) ANALYSIS OF NANOPORE SIGNAL USING A MACHINE-LEARNING TECHNIQUE

(71) Applicant: Oxford Nanopore Technologies PLC, Oxford (GB)

(72) Inventor: Timothy Lee Massingham, Oxford (GB)

(73) Assignee: Oxford Nanopore Technologies PLC, Oxford (GB)

( * ) Notice: Subject to any disclaimer, the term of this patent is extended or adjusted under 35 U.S.C. 154(b) by 816 days.

(21) Appl. No.: 16/696,010

(22) Filed: Nov. 26, 2019

(65) Prior Publication Data

US 2020/0176082 A1 Jun. 4, 2020

(30) Foreign Application Priority Data

Nov. 28, 2018 (GB) ........................... 1819378

(51) Int. Cl.
*C12Q 1/6869* (2018.01)
*G06F 18/214* (2023.01)
(Continued)

(52) U.S. Cl.
CPC ......... *C12Q 1/6869* (2013.01); *G06F 18/214* (2023.01); *G06N 3/045* (2023.01);
(Continued)

(58) Field of Classification Search
None
See application file for complete search history.

(56) References Cited

U.S. PATENT DOCUMENTS

2015/0057948 A1* 2/2015 Reid ................... C12Q 1/6858
702/25
2016/0162634 A1* 6/2016 Reid ................ G01N 27/44791
702/19
(Continued)

FOREIGN PATENT DOCUMENTS

WO WO 2000/28312 A1 5/2000
WO WO 2000/79257 A1 12/2000
(Continued)

OTHER PUBLICATIONS

Matthew Landry and Stephen Winters-Hilt. Analysis of nanopore detector measurements using Machine-Learning methods, with application to single-molecule kinetic analysis. 2007. BMC Bioinformatics 2007, 8(Suppl 7):S12 (Year: 2007).*
(Continued)

*Primary Examiner* — Olivia M. Wise
*Assistant Examiner* — Mary C Leverett
(74) *Attorney, Agent, or Firm* — Wolf, Greenfield & Sacks, P.C.

(57) ABSTRACT

Techniques for estimating a polymer sequence of a polymer based on a signal produced as a result of translocation of the polymer through a nanopore are described. The techniques may analyze portions of the signal to estimate whether there was a transition in the polymer sequence during each respective portion and which units of the sequence the transition was between. The techniques may comprise operation of one or more neural networks into which data from the signal may be input. The techniques may include generating a plurality of weights for a portion of the signal, wherein each weight is associated with a transition between labeled units of the polymer. The weights may be indicative of a likelihood that a transition occurred between a first of
(Continued)

the labeled units to a second of the labeled units within the portion of the signal.

24 Claims, 20 Drawing Sheets

Specification includes a Sequence Listing.

(51) Int. Cl.
    *G06N 3/045*      (2023.01)
    *G06N 3/084*      (2023.01)
    *G06N 20/20*      (2019.01)
    *G16B 30/00*      (2019.01)
    *G16B 40/10*      (2019.01)

(52) U.S. Cl.
    CPC ............ *G06N 3/084* (2013.01); *G06N 20/20* (2019.01); *G16B 30/00* (2019.02); *G16B 40/10* (2019.02)

(56) References Cited

U.S. PATENT DOCUMENTS

2017/0091427 A1* 3/2017 Massingham .......... G16B 30/00
2017/0096703 A1* 4/2017 Dolan .................... G16B 40/00

FOREIGN PATENT DOCUMENTS

| WO | WO 2005/124888 A1 | 12/2005 | |
|---|---|---|---|
| WO | WO 2008/102102 A2 | 8/2008 | |
| WO | WO 2009/035647 A1 | 3/2009 | |
| WO | WO 2009/077734 A2 | 6/2009 | |
| WO | WO 2010/086603 A1 | 8/2010 | |
| WO | WO 2010/086622 A1 | 8/2010 | |
| WO | WO 2010/109197 A2 | 9/2010 | |
| WO | WO 2010/122293 A1 | 10/2010 | |
| WO | WO 2011/046706 A1 | 4/2011 | |
| WO | WO 2011/067559 A1 | 6/2011 | |
| WO | WO 2012/005857 A1 | 1/2012 | |
| WO | WO 2012/033524 A2 | 3/2012 | |
| WO | WO 2012/107778 A2 | 8/2012 | |
| WO | WO 2012/138357 A1 | 10/2012 | |
| WO | WO 2013/014451 A1 | 1/2013 | |
| WO | WO 2013/041878 A1 | 3/2013 | |
| WO | WO 2013/153359 A1 | 10/2013 | |
| WO | WO 2014/064443 A2 | 5/2014 | |
| WO | WO 2014/064444 A1 | 5/2014 | |
| WO | WO 2015/140535 A1 | 9/2015 | |
| WO | WO-2015173587 A1 * | 11/2015 | ....... G01N 33/48721 |
| WO | WO 2016/034591 A2 | 3/2016 | |
| WO | WO 2016/187519 A2 | 3/2016 | |
| WO | WO 2016/181118 A1 | 11/2016 | |
| WO | WO-2018203084 A1 * | 11/2018 | .......... C12Q 1/6869 |
| WO | WO 2020/049293 A1 | 3/2020 | |

OTHER PUBLICATIONS

Misiunas K, Ermann N, Keyser UF. QuipuNet: Convolutional Neural Network for Single-Molecule Nanopore Sensing. Nano Lett. Jun. 13, 2018;18(6):4040-4045. doi: 10.1021/acs.nanolett.8b01709. Epub Jun. 1, 2018. (Year: 2018).*

Boža V, Brejová B, Vinař T. DeepNano: Deep recurrent neural networks for base calling in MinION nanopore reads. PLoS One. Jun. 5, 2017;12(6):e0178751. doi: 10.1371/journal.pone.0178751. eCollection 2017. (Year: 2017).*

Teng H, Cao MD, Hall MB, Duarte T, Wang S, Coin LJM. Chiron: translating nanopore raw signal directly into nucleotide sequence using deep learning. Gigascience. May 1, 2018;7(5):giy037. doi: 10.1093/gigascience/giy037. (Year: 2018).*

International Search Report and Written Opinion for Application No. PCT/GB2019/053334, mailed Feb. 27, 2020.

International Preliminary Report on Patentability for Application No. PCT/GB2019/053334, mailed Jun. 10, 2021.

Boza et al., DeepNano: Deep recurrent neural networks for base calling in MinION nanopore reads. PLoS One. Jun. 5, 2017;12(6):e0178751. doi: 10.1371/journal.pone.0178751.

Butler et al., Single-molecule DNA detection with an engineered MspA protein nanopore. Proc Natl Acad Sci U S A. Dec. 30, 2008;105(52):20647-52. doi: 10.1073/pnas.0807514106. Epub Dec. 19, 2008.

Gers et al., Recurrent nets that time and count. In Proceedings of the IEEE-INNS-ENNS International Joint Conference on Neural Networks. IJCNN 2000. Neural Computing: New Challenges and Perspectives for the New Millennium Jul. 27, 2000 (vol. 3, pp. 189-194). IEEE.

Gonzalez-Perez et al., Biomimetic triblock copolymer membrane arrays: a stable template for functional membrane proteins. Langmuir. Sep. 15, 2009;25(18):10447-50. doi: 10.1021/la902417m.

Graves et al., Connectionist temporal classification: labelling unsegmented sequence data with recurrent neural networks. In Proceedings of the 23rd international conference on Machine learning Jun. 25, 2006 (pp. 369-376).

Heron et al., Simultaneous measurement of ionic current and fluorescence from single protein pores. J Am Chem Soc. Feb. 11, 2009;131(5):1652-3. doi: 10.1021/ja808128s.

Hochreiter et al., Long short-term memory. Neural Comput. Nov. 15, 1997;9(8):1735-80. doi: 10.1162/neco.1997.9.8.1735.

Ivanov et al., DNA tunneling detector embedded in a nanopore. Nano Lett. Jan. 12, 2011;11(1):279-85. doi: 10.1021/nl103873a. Epub Dec. 6, 2010.

Lafferty et al., Conditional Random Fields: Probabilistic Models for Segmenting and Labeling Sequence Data. In Proceedings of the International Conference on Machine Learning, 2001, 10 pages.

Landry et al., Analysis of nanopore detector measurements using Machine-Learning methods, with application to single-molecule kinetic analysis. BMC Bioinformatics. Nov. 1, 2007;8 Suppl 7(Suppl 7):S12. doi: 10.1186/1471-2105-8-S7-S12.

Li et al., DeepSimulator: a deep simulator for Nanopore sequencing. Bioinformatics. Sep. 1, 2018;34(17):2899-2908. doi: 10.1093/bioinformatics/bty223.

Lieberman et al., Processive replication of single DNA molecules in a nanopore catalyzed by phi29 DNA polymerase. J Am Chem Soc. Dec. 22, 2010;132(50):17961-72. doi: 10.1021/ja1087612. Epub Dec. 1, 2010. Author Manuscript, 21 pages.

Luan et al., Base-by-base ratcheting of single stranded DNA through a solid-state nanopore. Phys Rev Lett. Jun. 11, 2010;104(23):238103. doi: 10.1103/PhysRevLett.104.238103. Epub Jun. 10, 2010. Author Manuscript, 9 pages.

McCallum et al., Maximum entropy Markov models for information extraction and segmentation. In Icml Jun. 29, 2000 (vol. 17, No. 2000, pp. 591-598).

Soni et al., Synchronous optical and electrical detection of biomolecules traversing through solid-state nanopores. Rev Sci Instrum. Jan. 2010;81(1):014301. doi: 10.1063/1.3277116.

Stoddart et al., Multiple base-recognition sites in a biological nanopore: two heads are better than one. Angew Chem Int Ed Engl. 2010;49(3):556-9. doi: 10.1002/anie.200905483. Author Manuscript, 8 pages.

Stoddart et al., Nucleobase recognition in ssDNA at the central constriction of the alpha-hemolysin pore. Nano Lett. Sep. 8, 2010;10(9):3633-7. doi: 10.1021/nl101955a. Author Manuscript, 11 pages.

Stoddart et al., Single-nucleotide discrimination in immobilized DNA oligonucleotides with a biological nanopore. Proc Natl Acad Sci U S A. May 12, 2009;106(19):7702-7. doi: 10.1073/pnas. 0901054106. Epub Apr. 20, 2009.

Stoiber et al., BasecRAWller: Streaming nanopore basecalling directly from raw signal. BioRxiv. Jan. 1, 2017:133058. doi: 10.1101/133058. Retrieved from the Internet: URL:https://www.biorxiv.org/content/biorxiv/early/2017/05/01/133058.full.pdf.

Teng et al., Chiron: translating nanopore raw signal directly into nucleotide sequence using deep learning. Gigascience. May 1, 2018;7(5):giy037. doi: 10.1093/gigascience/giy037. Erratum in: Gigascience. May 1, 2019;8(5).

(56) References Cited

OTHER PUBLICATIONS

Boufounos et al., Basecalling using hidden Markov models. Journal of the Franklin Institute. Jan. 1, 2004;341(1-2):23-36.

\* cited by examiner

Fig. 10

Basic

|   | A | C | G | T |
|---|---|---|---|---|
| A | $W_{11}$ | $W_{12}$ | $W_{13}$ | $W_{14}$ |
| C | $W_{21}$ | $W_{22}$ | $W_{23}$ | $W_{24}$ |
| G | $W_{31}$ | $W_{32}$ | $W_{33}$ | $W_{34}$ |
| T | $W_{41}$ | $W_{42}$ | $W_{43}$ | $W_{44}$ |

Fig. 11

Blanks

|   | A | C | G | T | B |
|---|---|---|---|---|---|
| A | $W_{11}$ | $W_{12}$ | $W_{13}$ | $W_{14}$ | $W_{15}$ |
| C | $W_{21}$ | $W_{22}$ | $W_{23}$ | $W_{24}$ | $W_{25}$ |
| G | $W_{31}$ | $W_{32}$ | $W_{33}$ | $W_{34}$ | $W_{35}$ |
| T | $W_{41}$ | $W_{42}$ | $W_{43}$ | $W_{44}$ | $W_{45}$ |
| B | $W_{51}$ | $W_{52}$ | $W_{53}$ | $W_{54}$ | $W_{55}$ |

Fig. 12

CpG Methylation

|   | A | C | G | T | B | $C^M$ |
|---|---|---|---|---|---|---|
| A | $W_{11}$ | $W_{12}$ | $W_{13}$ | $W_{14}$ | $W_{15}$ | $W_{16}$ |
| C | $W_{21}$ | $W_{22}$ | $W_{23}$ | $W_{24}$ | $W_{25}$ | $W_{26}$ |
| G | $W_{31}$ | $W_{32}$ | $W_{33}$ | $W_{34}$ | $W_{35}$ | $W_{36}$ |
| T | $W_{41}$ | $W_{42}$ | $W_{43}$ | $W_{44}$ | $W_{45}$ | $W_{46}$ |
| B | $W_{51}$ | $W_{52}$ | $W_{53}$ | $W_{54}$ | $W_{55}$ | $W_{56}$ |
| $C^M$ | – | – | $W_{63}$ | – | $W_{65}$ | $W_{66}$ |

Fig. 13

Multi-Stay

|   | A | C | G | T | $A^s$ | $C^s$ | $G^s$ | $T^s$ |
|---|---|---|---|---|---|---|---|---|
| A | $W_{11}$ | $W_{12}$ | $W_{13}$ | $W_{14}$ | $W_{15}$ | – | – | – |
| C | $W_{21}$ | $W_{22}$ | $W_{23}$ | $W_{24}$ | – | $W_{26}$ | – | – |
| G | $W_{31}$ | $W_{32}$ | $W_{33}$ | $W_{34}$ | – | – | $W_{37}$ | – |
| T | $W_{41}$ | $W_{42}$ | $W_{43}$ | $W_{44}$ | – | – | – | $W_{48}$ |
| $A^s$ | $W_{51}$ | $W_{52}$ | $W_{53}$ | $W_{54}$ | $W_{55}$ | – | – | – |
| $C^s$ | $W_{61}$ | $W_{62}$ | $W_{63}$ | $W_{64}$ | – | $W_{66}$ | – | – |
| $G^s$ | $W_{71}$ | $W_{72}$ | $W_{73}$ | $W_{74}$ | – | – | $W_{77}$ | – |
| $T^s$ | $W_{81}$ | $W_{82}$ | $W_{83}$ | $W_{84}$ | – | – | – | $W_{88}$ |

Fig. 14

Flip-Flop

|   | A | C | G | T | $A^f$ | $C^f$ | $G^f$ | $T^f$ |
|---|---|---|---|---|---|---|---|---|
| A | $W_{11}$ | $W_{12}$ | $W_{13}$ | $W_{14}$ | $W_{15}$ | – | – | – |
| C | $W_{21}$ | $W_{22}$ | $W_{23}$ | $W_{24}$ | – | $W_{26}$ | – | – |
| G | $W_{31}$ | $W_{32}$ | $W_{33}$ | $W_{34}$ | – | – | $W_{37}$ | – |
| T | $W_{41}$ | $W_{42}$ | $W_{43}$ | $W_{44}$ | – | – | – | $W_{48}$ |
| $A^f$ | $W_{51}$ | $W_{52}$ | $W_{53}$ | $W_{54}$ | $W_{55}$ | – | – | – |
| $C^f$ | $W_{61}$ | $W_{62}$ | $W_{63}$ | $W_{64}$ | – | $W_{66}$ | – | – |
| $G^f$ | $W_{71}$ | $W_{72}$ | $W_{73}$ | $W_{74}$ | – | – | $W_{77}$ | – |
| $T^f$ | $W_{81}$ | $W_{82}$ | $W_{83}$ | $W_{84}$ | – | – | – | $W_{88}$ |

Fig. 16A

RLE-discrete

| | $A^1$ | $C^1$ | $G^1$ | $T^1$ | $A^2$ | $C^2$ | $G^2$ | $T^2$ | $A^3$ | .... |
|---|---|---|---|---|---|---|---|---|---|---|
| $A^1$ | $W_{11}$ | $W_{12}$ | $W_{13}$ | $W_{14}$ | – | $W_{16}$ | $W_{17}$ | $W_{18}$ | – | .... |
| $C^1$ | $W_{21}$ | $W_{22}$ | $W_{23}$ | $W_{24}$ | $W_{25}$ | – | $W_{27}$ | $W_{28}$ | $W_{29}$ | .... |
| $G^1$ | $W_{31}$ | $W_{32}$ | $W_{33}$ | $W_{34}$ | $W_{35}$ | $W_{36}$ | – | $W_{38}$ | $W_{39}$ | .... |
| $T^1$ | $W_{41}$ | $W_{42}$ | $W_{43}$ | $W_{44}$ | $W_{45}$ | $W_{46}$ | $W_{47}$ | – | $W_{49}$ | .... |
| $A^2$ | – | $W_{52}$ | $W_{53}$ | $W_{54}$ | $W_{55}$ | $W_{56}$ | $W_{57}$ | $W_{58}$ | – | .... |
| $C^2$ | $W_{61}$ | – | $W_{63}$ | $W_{64}$ | $W_{65}$ | $W_{66}$ | $W_{67}$ | $W_{68}$ | $W_{69}$ | .... |
| $G^2$ | $W_{71}$ | $W_{72}$ | – | $W_{74}$ | $W_{75}$ | $W_{76}$ | $W_{77}$ | $W_{78}$ | $W_{79}$ | .... |
| $T^2$ | $W_{81}$ | $W_{82}$ | $W_{83}$ | – | $W_{85}$ | $W_{86}$ | $W_{87}$ | $W_{88}$ | $W_{89}$ | .... |
| $A^3$ | – | $W_{92}$ | $W_{93}$ | $W_{94}$ | – | $W_{96}$ | $W_{97}$ | $W_{98}$ | $W_{99}$ | .... |
| ⋮ | ⋮ | ⋮ | ⋮ | ⋮ | ⋮ | ⋮ | ⋮ | ⋮ | ⋮ | .... |

Fig. 16B

|     | A        | C        | G        | T        | $A^H$    | $C^H$    | $G^H$    | $T^H$    |
|-----|----------|----------|----------|----------|----------|----------|----------|----------|
| A   | –        | $W_{12}$ | $W_{13}$ | $W_{14}$ | $W_{15}$ | –        | –        | –        |
| C   | $W_{21}$ | –        | $W_{23}$ | $W_{24}$ | –        | $W_{26}$ | –        | –        |
| G   | $W_{31}$ | $W_{32}$ | –        | $W_{34}$ | –        | –        | $W_{37}$ | –        |
| T   | $W_{41}$ | $W_{42}$ | $W_{43}$ | –        | –        | –        | –        | $W_{48}$ |
| $A^H$ | –      | $W_{52}$ | $W_{53}$ | $W_{54}$ | $W_{55}$ | –        | –        | –        |
| $C^H$ | $W_{61}$ | –      | $W_{63}$ | $W_{64}$ | –        | $W_{66}$ | –        | –        |
| $G^H$ | $W_{71}$ | $W_{72}$ | –      | $W_{74}$ | –        | –        | $W_{77}$ | –        |
| $T^H$ | $W_{81}$ | $W_{82}$ | $W_{83}$ | –      | –        | –        | –        | $W_{88}$ |

Fig. 17

RLE-Categorical

|   | 1 | 2 | 3 | 4 | .... |
|---|---|---|---|---|------|
| A | $l_{11}$ | $l_{12}$ | $l_{13}$ | $l_{14}$ | .... |
| C | $l_{21}$ | $l_{22}$ | $l_{23}$ | $l_{24}$ | .... |
| G | $l_{31}$ | $l_{32}$ | $l_{33}$ | $l_{34}$ | .... |
| T | $l_{41}$ | $l_{42}$ | $l_{43}$ | $l_{44}$ | .... |

Fig. 18

RLE-Parameterised

|   | $P_1$ | $P_2$ | .... |
|---|-------|-------|------|
| A | $P_{11}$ | $P_{12}$ | .... |
| C | $P_{21}$ | $P_{22}$ | .... |
| G | $P_{31}$ | $P_{32}$ | .... |
| T | $P_{41}$ | $P_{42}$ | .... |

Fig. 20A

| Distribution | Parameters | $\mathbb{P}(X = x)$, scheme 1 | $\mathbb{P}(X = x)$, scheme 2 |
|---|---|---|---|
| Gamma | shape $\alpha > 0$; scale $\beta > 0$ | $\frac{1}{\Gamma(\alpha)}[\gamma(\alpha, \frac{x+1}{\beta}) - \gamma(\alpha, \frac{x}{\beta})]$ | $\frac{1}{\Gamma(\alpha)}[\gamma(\alpha, \frac{x+1/2}{\beta}) - \gamma(\alpha, \frac{x-1/2}{\beta})]$ |
| Log-Logistic | shape $\alpha > 0$; scale $\beta > 0$ | $\frac{1}{1+(\frac{x+1}{\alpha})^{-\beta}} - \frac{1}{1+(x/\alpha)^{-\beta}}$ | $\frac{1}{1+(\frac{x+1/2}{\alpha})^{-\beta}} - \frac{1}{1+(\frac{x-1/2}{\alpha})^{-\beta}}$ |
| Log-Normal | log-mean $\mu \in \mathbb{R}$; log-SD $\sigma > 0$ | $\frac{1}{2}\Phi(\frac{\log(x+1) - \mu}{\sigma\sqrt{2}}) - \frac{1}{2}\Phi(\frac{\log x - \mu}{\sigma\sqrt{2}})$ | $\frac{1}{2}\Phi(\frac{\log(x+1/2) - \mu}{\sigma\sqrt{2}}) - \frac{1}{2}\Phi(\frac{\log(x-1/2) - \mu}{\sigma\sqrt{2}})$ |
| Weibull | shape $\alpha > 0$; scale $\beta > 0$ | $e^{-(x/\beta)^{\alpha}} - e^{-(\frac{x+1}{\beta})^{\alpha}}$ | $e^{-(\frac{x-1/2}{\beta})^{\alpha}} - e^{-(\frac{x+1/2}{\beta})^{\alpha}}$ |

Fig. 20B

|  | $P_1$ | $P_2$ | .... |
|---|---|---|---|
| A→C | $P_{11}$ | $P_{12}$ | .... |
| A→G | $P_{21}$ | $P_{22}$ | .... |
| A→T | $P_{31}$ | $P_{32}$ | .... |
| C→A | $P_{41}$ | $P_{42}$ | .... |
| C→G | $P_{51}$ | $P_{52}$ | .... |
| C→T | $P_{61}$ | $P_{62}$ | .... |
| G→A | $P_{71}$ | $P_{72}$ | .... |
| G→C | $P_{81}$ | $P_{82}$ | .... |
| G→T | $P_{91}$ | $P_{92}$ | .... |
| T→A | $P_{10-1}$ | $P_{10-2}$ | .... |
| T→C | $P_{11-1}$ | $P_{11-2}$ | .... |
| T→G | $P_{12-1}$ | $P_{12-2}$ | .... |

Fig. 20C

|  | $P_1$ | $P_2$ | .... |
|---|---|---|---|
| C→A→C | $P_{11}$ | $P_{12}$ | .... |
| G→A→G | $P_{21}$ | $P_{22}$ | .... |
| T→A→T | $P_{31}$ | $P_{32}$ | .... |
| G→A→C | $P_{41}$ | $P_{42}$ | .... |
| T→A→G | $P_{51}$ | $P_{52}$ | .... |
| T→A→T | $P_{61}$ | $P_{62}$ | .... |
| T→A→C | $P_{71}$ | $P_{72}$ | .... |
| C→A→G | $P_{81}$ | $P_{82}$ | .... |
| G→A→T | $P_{91}$ | $P_{92}$ | .... |
| A→C→A | $P_{10-1}$ | $P_{10-2}$ | .... |
| G→C→G | $P_{11-1}$ | $P_{11-2}$ | .... |
| T→C→T | $P_{12-1}$ | $P_{12-2}$ | .... |
| G→C→A | $P_{13-1}$ | $P_{13-2}$ | .... |
| T→C→G | $P_{14-1}$ | $P_{14-2}$ | .... |
| A→C→T | $P_{15-1}$ | $P_{15-2}$ | .... |
| T→C→A | $P_{16-1}$ | $P_{16-2}$ | .... |
| A→C→G | $P_{17-1}$ | $P_{17-2}$ | .... |
| G→C→T | $P_{18-1}$ | $P_{18-2}$ | .... |
| T→G→T | $P_{19-1}$ | $P_{19-2}$ | .... |
| A→G→A | $P_{20-1}$ | $P_{20-2}$ | .... |
| C→G→C | $P_{21-1}$ | $P_{21-2}$ | .... |
| A→G→T | $P_{22-1}$ | $P_{22-2}$ | .... |
| C→G→A | $P_{23-1}$ | $P_{23-2}$ | .... |
| T→G→C | $P_{24-1}$ | $P_{24-2}$ | .... |
| C→G→T | $P_{25-1}$ | $P_{25-2}$ | .... |
| T→G→A | $P_{26-1}$ | $P_{26-2}$ | .... |
| A→G→C | $P_{27-1}$ | $P_{27-2}$ | .... |
| A→T→A | $P_{28-1}$ | $P_{28-2}$ | .... |
| C→T→C | $P_{29-1}$ | $P_{29-2}$ | .... |
| G→T→G | $P_{30-1}$ | $P_{30-2}$ | .... |
| C→T→A | $P_{31-1}$ | $P_{31-2}$ | .... |
| G→T→C | $P_{32-1}$ | $P_{32-2}$ | .... |
| A→T→G | $P_{33-1}$ | $P_{33-2}$ | .... |
| C→T→A | $P_{34-1}$ | $P_{34-2}$ | .... |
| G→T→C | $P_{35-1}$ | $P_{35-2}$ | .... |
| A→T→G | $P_{36-1}$ | $P_{36-2}$ | .... |

Fig. 21

|       | A        | C        | G        | T        | B        | $C^M$    |
|-------|----------|----------|----------|----------|----------|----------|
| A     | $W_{11}$ | $W_{12}$ | $W_{13}$ | $W_{14}$ | $W_{15}$ | $W_{16}$ |
| C     | $W_{21}$ | $W_{22}$ | $W_{23}$ | $W_{24}$ | $W_{25}$ | $W_{26}$ |
| G     | $W_{31}$ | $W_{32}$ | $W_{33}$ | $W_{34}$ | $W_{35}$ | $W_{36}$ |
| T     | $W_{41}$ | $W_{42}$ | $W_{43}$ | $W_{44}$ | $W_{45}$ | $W_{46}$ |
| B     | $W_{51}$ | $W_{52}$ | $W_{53}$ | $W_{54}$ | $W_{55}$ | $W_{56}$ |
| $C^M$ | $W_{61}$ | $W_{62}$ | $W_{63}$ | $W_{64}$ | $W_{65}$ | $W_{66}$ |

Fig. 22

|   | C     | $C^M$ |
|---|-------|-------|
| C | $M_1$ | $M_2$ |

Fig. 25

$$f_k^0 = 0 \quad \forall k \quad \text{Initialise forward vector}$$
$$f_k^{i+1} = \max_j f_j^i + w_{jk}^i \quad \text{Best path update}$$
$$t_k^{i+1} = \operatorname*{argmax}_j f_j^i + w_{jk}^i \quad \text{Traceback update}$$
$$S = \max_j f_j^n \quad \text{Calculate score}$$
$$P_n = \operatorname*{argmax}_j j_j^n \quad \text{Highest score state at final position}$$
$$P_{i-1} = t_{P_i}^i \quad \text{Traceback to find best path}$$

Fig. 26

$$f_k^0 = p_k^0 \quad \text{Initialise forward vector}$$
$$f_k^{i+1} = \max_j f_j^i + T_{jk} p_k^{i+1} \quad \text{Best path update}$$
$$t_k^{i+1} = \operatorname*{argmax}_j f_j^i + T_{jk} p_k^{i+1} \quad \text{Traceback update}$$
$$S = \max_j f_j^n \quad \text{Calculate score}$$
$$P_n = \operatorname*{argmax}_j j_j^n \quad \text{Highest score state at final position}$$
$$P_{i-1} = t_{P_i}^i \quad \text{Traceback to find best path}$$

Fig. 27

$$f_k^0 = \log p_k^0 \quad \text{Initialise forward vector}$$
$$f_k^{i+1} = \max_j f_j^i + T_{jk} \log p_k^{i+1} \quad \text{Best path update}$$
$$t_k^{i+1} = \operatorname*{argmax}_j f_j^i + T_{jk} \log p_k^{i+1} \quad \text{Traceback update}$$
$$S = \max_j f_j^n \quad \text{Calculate score}$$
$$P_n = \operatorname*{argmax}_j j_j^n \quad \text{Highest score state at final position}$$
$$P_{i-1} = t_{P_i}^i \quad \text{Traceback to find best path}$$

Fig. 28

$$f_k^0 = 0 \quad \forall k \quad \text{Initialise forward vector}$$

$$f_k^{i+1} = \log \sum_j e^{f_j^i + w_{jk}^i} \quad \text{Forward update}$$

$$b_k^N = 0 \quad \forall k \quad \text{Initialise backward vector}$$

$$b_k^{i-1} = \log \sum_j e^{b_j^i + w_{kj}^i} \quad \text{Backward update}$$

$$S = \quad \text{Score (normalising factor)}$$

$$p_j^i = \frac{1}{S} e^{f_j^i + b_j^i} \quad \text{Posterior probability (label } j\text{)}$$

$$p_{jk}^i = \frac{1}{S} e^{f_j^i + w_{jk}^i + b_k^{i+1}} \quad \text{Posterior probability (transition } j \to k\text{)}$$

Fig. 29

$$m_{j\,j+1}^i = w_{S_j\,S_{j+1}}^i \quad \text{Move from state } S_j \text{ to } S_{j+1}$$

$$m_{j\,j}^i = w_{S_j\,S_j}^i \quad \text{Stay in state } S_j$$

$$m_{j\,k}^i = 0 \quad \text{otherwise}$$

Fig. 30

$$f_k^0 = 0 \quad k = 1; \; -\infty \text{ otherwise} \quad \text{Initialise forward vector}$$

$$f_k^{i+1} = \log \sum_j e^{f_j^i + m_{jk}^i} \quad \text{All paths update}$$

$$S = f_N^n \quad \text{Calculate score}$$

Fig. 31

$$m^i_{j\,j+1} = w^i_{S_j S_{j+1}} \quad \text{Move from position } j \text{ to } j+1$$
$$m^i_{j+N+1\,j+1} = w^i_{R_j S_{j+1}} \quad \text{Move from position } j \text{ to } j+1 \text{ having remained}$$
$$m^i_{j\,j+N+1} = w^i_{S_j R_j} \quad \text{Remain in position } j \text{ (newly arrival)}$$
$$m^i_{j+N+1\,j+N+1} = w^i_{R_j R_j} \quad \text{Remain in position } j \text{ (previous arrival)}$$
$$m^i_{j\,k} = 0 \quad \text{otherwise}$$

Fig. 32

$$m^i_{j\,j+1} = w^i_{S_j S_{j+1}} + r^i_{S_{j+1}:L_{j+1}} \quad \text{Move from position } j \text{ to } j+1$$
$$m^i_{j+N+1\,j+1} = w^i_{R_j S_{j+1}} + r^i_{S_{j+1}:L_{j+1}} \quad \text{Move from position } j \text{ to } j+1 \text{ having remained}$$
$$m^i_{j\,j+N+1} = w^i_{S_j R_j} \quad \text{Remain in position } j \text{ (newly arrival)}$$
$$m^i_{j+N+1\,j+N+1} = w^i_{R_j R_j} \quad \text{Remain in position } j \text{ (previous arrival)}$$
$$m^i_{j\,k} = 0 \quad \text{otherwise}$$

CRF flip/flop – chunk 22

$f_k^0 = 0 k = 1; -\infty$ otherwise    Initialise forward vector
$f_k^{i+1} = \max_j f_j^i + m_{jk}^i$    Best path update
$S = f_N^n$    Calculate score

| Functor | | |
|---|---|---|
| $\log \sum_j \exp$ | All paths | $L_1$ norm |
| $\max_j$ | Best path | $L_\infty$ norm |
| $\frac{1}{a}\log \sum_j \exp a$ | Sharpened all paths | $L_a$ norm |
| $\log \sum_j \exp - \max_j$ | All but best path | |
| $p\max_j + (1-p)\log \sum_j \exp$ | Up-weighted best path | |

Fig. 37

| Model | Alignment of call to reference |
|---|---|
| Unsharpened | GATACTAT---CACGATATTTTCTCTTTTTT------------GAGACAG--GTC (SEQ ID NO: 4) Call<br>\|\|\|\|\|\|\|\| \|\|\|\|\|\|\|\|\|\|\|\|\|\|\|\|·\|\|\|\|\|\| \|\|\|\|\|\|\| \|\|\|<br>GATACTATATCACGATATTTTCTTTTTTTTTTTTTTTTTTTTTTTTGAGACGGAGTC (SEQ ID NO: 6) Ref |
| Sharpened | GATACTAT---CACGATATTTTCTTTTTTTTTTTTTTTTTTTTTTTTGAGACGG--GTC (SEQ ID NO: 5) Call<br>\|\|\|\|\|\|\|\| \|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\| \|\|\|<br>GATACTATATCACGATATTTTCTTTTTTTTTTTTTTTTTTTTTTTTGAGACGGAGTC (SEQ ID NO: 6) Ref |

SEQUENCE LISTING

```
<160> NUMBER OF SEQ ID NOS: 6

<210> SEQ ID NO 1
<211> LENGTH: 13
<212> TYPE: DNA
<213> ORGANISM: Artificial Sequence
<220> FEATURE:
<223> OTHER INFORMATION: Synthetic Polynucleotide

<400> SEQUENCE: 1
aaaaaaaaaa aaa                                                        13

<210> SEQ ID NO 2
<211> LENGTH: 32
<212> TYPE: DNA
<213> ORGANISM: Artificial Sequence
<220> FEATURE:
<223> OTHER INFORMATION: Synthetic Polynucleotide

<400> SEQUENCE: 2
caataccttt aaaaaaaga aacttttagc tc                                    32
```

```
<210> SEQ ID NO 3
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 3
taattcaaac tttttttctg ataagctggt                                    30

<210> SEQ ID NO 4
<211> LENGTH: 40
<212> TYPE: DNA
<213> ORGANISM: Artificial Sequence
<220> FEATURE:
<223> OTHER INFORMATION: Synthetic Polynucleotide

<400> SEQUENCE: 4
gatactatca cgatatttta tctttttttt gagacaggtc                         40

<210> SEQ ID NO 5
<211> LENGTH: 57
<212> TYPE: DNA
<213> ORGANISM: Artificial Sequence
<220> FEATURE:
<223> OTHER INFORMATION: Synthetic Polynucleotide

<400> SEQUENCE: 5
gatactatca cgatattttc tttttttttt tttttttttt tttttttgag acgggtc      57

<210> SEQ ID NO 6
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 6
gatactatat cacgatattt tcttttttttt tttttttttt ttttttttg agacggagtc   60
```

ANALYSIS OF NANOPORE SIGNAL USING A MACHINE-LEARNING TECHNIQUE

CROSS-REFERENCE TO RELATED APPLICATIONS

This application claims priority under 35 U.S.C. § 119(a) to British application number 1819378.9, filed Nov. 28, 2018, the entire contents of which is hereby incorporated by reference in its entirety.

TECHNICAL FIELD

Provided herein are techniques for the analysis of a signal derived from a polymer, for example but without limitation a polynucleotide, during translocation of the polymer with respect to a nanopore.

REFERENCE TO A SEQUENCE LISTING SUBMITTED AS A TEXT FILE VIA EFS-WEB

The instant application contains a Sequence Listing which has been submitted in ASCII format via EFS-Web and is hereby incorporated by reference in its entirety. Said ASCII copy, created on Jan. 7, 2020, is named 0036670094US00-SEQ-MZA and is 2 kilobytes in size.

BACKGROUND

Transmembrane pores (e.g., nanopores) have been used to identify small molecules or folded proteins and to monitor chemical or enzymatic reactions at the single molecule level. The electrophoretic translocation of DNA across nanopores reconstituted into artificial membranes holds great promise for practical applications such as DNA sequencing, and biomarker recognition.

SUMMARY

According to some aspects, a method is provided of estimating a sequence of polymer units within a polymer based on a time-ordered series of measurements produced during translocation of the polymer through a nanopore, the method comprising selecting, using at least one processor, a contiguous portion of the time-ordered series of measurements, determining, using the at least one processor, a set of weights based on the portion of the time-ordered series of measurements, each weight of the set of weights being associated with respective first and second labels and being indicative of the likelihood that a transition between a polymer unit having the first label and a polymer unit having the second label occurred within a measurement period represented by the portion of the time-ordered series of measurements, repeating, using the at least one processor, the selecting and determining steps for a plurality of different contiguous portions of the time-ordered series of measurements, thereby determining a plurality of sets of weights with each set of weights being associated with a different respective measurement period, and determining, using the at least one processor, an estimate of the sequence of polymer units within the polymer based on the plurality of sets of weights.

According to some embodiments, determining the set of weights based on the portion of the time-ordered series of measurements comprises providing the portion of the time-ordered series of measurements as an input to a first neural network, and generating, by executing the first neural network using the at least one processor, a feature vector comprising a plurality of values each representing detected features within the portion of the time-ordered series of measurements.

According to some embodiments, the first neural network is a convolutional neural network (CNN).

According to some embodiments, a number of the measurements in the portion of the time-ordered series of measurements is different than a number of the plurality of values of the feature vector.

According to some embodiments, determining the set of weights based on the portion of the time-ordered series of measurements comprises providing the feature vector as an input to a second neural network, and generating, by executing the second neural network using the at least one processor, the set of weights based on the feature vector.

According to some embodiments, the second neural network is a recurrent neural network (RNN).

According to some embodiments, the method further comprises selecting a first contiguous portion of the time-ordered series of measurements, the first contiguous portion of the time-ordered series of measurements consisting of a first number of measurements, and selecting a second contiguous portion of the time-ordered series of measurements, different from the first contiguous portion, the second contiguous portion of the time-ordered series of measurements consisting of the first number of measurements, wherein at least some of the time-ordered series of measurements are present in both the first and second contiguous portions of the time-ordered series of measurements.

According to some embodiments, each of the polymer units in the polymer is one of a finite, known group of polymer units, the group of polymer units consisting of N distinct polymer units, each of the first label and second label is one of a finite, known, group of labels, the group of labels consisting of M distinct labels, and M is greater than N.

According to some embodiments, the set of weights consists of M2 weights.

According to some embodiments, M is equal to N+1, and the group of labels consists of N labels each corresponding to respective ones of the group of polymer units, and a single label corresponding to a blank label, which represents a lack of a transition within the measurement period represented by the portion of the time-ordered series of measurements.

According to some embodiments, M is equal to 2×N, and the group of labels consists of N labels each corresponding to a first instance of respective ones of the group of polymer units, and N labels each corresponding to a second instance of the respective ones of the group of polymer units.

According to some embodiments, determining the estimate of the sequence of polymer units within the polymer based on the plurality of sets of weights comprises generating a Hidden Markov Model (HMM) wherein emission and transition probabilities of the HMM are represented by weights of the plurality of sets of weights, and determining, using the at least one processor, a most likely sequence of polymer units within the polymer based on the HMM.

According to some embodiments, each of the first label and second label is one of a finite, known, group of labels, and determining the most likely sequence of polymer units within the polymer based on the HMM comprises determining the most likely sequence of labels of the group of labels based on the HMM, and identifying polymer units that correspond to the labels of the group of labels.

According to some embodiments, the method further comprises measuring a current through the nanopore during translocation of the polymer through the nanopore, thereby generating a current measurement signal.

According to some embodiments, the method further comprises digitizing the current measurement signal, thereby producing the time-ordered series of measurements.

According to some aspects, a system is provided for estimating a sequence of polymer units within a polymer based on a time-ordered series of measurements produced during translocation of the polymer through a nanopore, the system comprising an analysis system comprising at least one processor, and at least one non-transitory computer readable medium storing instructions that, when executed by the at least one processor, perform a method comprising selecting, using the at least one processor, a contiguous portion of the time-ordered series of measurements, determining, using the at least one processor, a set of weights based on the portion of the time-ordered series of measurements, each weight of the set of weights being associated with respective first and second labels and being indicative of the likelihood that a transition between a polymer unit having the first label and a polymer unit having the second label occurred within a measurement period represented by the portion of the time-ordered series of measurements, repeating, using the at least one processor, the selecting and determining steps for a plurality of different contiguous portions of the time-ordered series of measurements, thereby determining a plurality of sets of weights with each set of weights being associated with a different respective measurement period, and determining, using the at least one processor, an estimate of the sequence of polymer units within the polymer based on the plurality of sets of weights.

According to some embodiments, determining the set of weights based on the portion of the time-ordered series of measurements comprises providing the portion of the time-ordered series of measurements as an input to a first neural network, and generating, by executing the first neural network using the at least one processor, a feature vector comprising a plurality of values each representing detected features within the portion of the time-ordered series of measurements.

According to some embodiments, the first neural network is a convolutional neural network (CNN).

According to some embodiments, a number of the measurements in the portion of the time-ordered series of measurements is different than a number of the plurality of values of the feature vector.

According to some embodiments, determining the set of weights based on the portion of the time-ordered series of measurements comprises providing the feature vector as an input to a second neural network, and generating, by executing the second neural network using the at least one processor, the set of weights based on the feature vector.

According to some embodiments, the second neural network is a recurrent neural network (RNN).

According to some embodiments, the method further comprises selecting a first contiguous portion of the time-ordered series of measurements, the first contiguous portion of the time-ordered series of measurements consisting of a first number of measurements, and selecting a second contiguous portion of the time-ordered series of measurements, different from the first contiguous portion, the second contiguous portion of the time-ordered series of measurements consisting of the first number of measurements, wherein at least some of the time-ordered series of measurements are present in both the first and second contiguous portions of the time-ordered series of measurements.

According to some embodiments, each of the polymer units in the polymer is one of a finite, known group of polymer units, the group of polymer units consisting of N distinct polymer units, each of the first label and second label is one of a finite, known, group of labels, the group of labels consisting of M distinct labels, and wherein M is greater than N.

According to some embodiments, the set of weights consists of $M^2$ weights.

According to some embodiments, M is equal to N+1, and the group of labels consists of N labels each corresponding to respective ones of the group of polymer units, and a single label corresponding to a blank label, which represents a lack of a transition within the measurement period represented by the portion of the time-ordered series of measurements.

According to some embodiments, M is equal to 2×N, and the group of labels consists of N labels each corresponding to a first instance of respective ones of the group of polymer units, and N labels each corresponding to a second instance of the respective ones of the group of polymer units.

According to some embodiments, determining the estimate of the sequence of polymer units within the polymer based on the plurality of sets of weights comprises generating a Hidden Markov Model (HMM) wherein emission and transition probabilities of the HMM are represented by weights of the plurality of sets of weights, and determining, using the at least one processor, a most likely sequence of polymer units within the polymer based on the HMM.

According to some embodiments, each of the first label and second label is one of a finite, known, group of labels, and wherein determining the most likely sequence of polymer units within the polymer based on the HMM comprises determining the most likely sequence of labels of the group of labels based on the HMM, and identifying polymer units that correspond to the labels of the group of labels.

According to some embodiments, the system further comprises a measurement unit configured to measure a current through the nanopore during translocation of the polymer through the nanopore, thereby generating a current measurement signal.

According to some embodiments, the measurement unit is further configured to digitize the current measurement signal, thereby producing the time-ordered series of measurements, and to provide the time-ordered series of measurements to the analysis unit.

The foregoing apparatus and method embodiments may be implemented with any suitable combination of aspects, features, and acts described above or in further detail below. These and other aspects, embodiments, and features of the present teachings can be more fully understood from the following description in conjunction with the accompanying drawings.

BRIEF DESCRIPTION OF DRAWINGS

Various aspects and embodiments will be described with reference to the following figures. It should be appreciated that the figures are not necessarily drawn to scale. In the drawings, each identical or nearly identical component that is illustrated in various figures is represented by a like numeral. For purposes of clarity, not every component may be labeled in every drawing.

FIG. 10 is table of a weight distribution where the weights correspond to transitions between labels representing four types of polynucleotide;

FIG. 11 is table of a weight distribution where the weights correspond to transitions between labels representing four types of polynucleotide and a blank;

FIG. 12 is table of a weight distribution where the weights correspond to transitions between labels representing five types of polynucleotide, one of which is methylated-C, and a blank FIG. 13 is table of a weight distribution where the weights correspond to transitions between labels including two labels corresponding to each of four types of polynucleotide;

FIG. 14 is table of a weight distribution where the weights correspond to homopolymers using a flip-flop representation;

FIG. 16A is table of a weight distribution where the weights represent homopolymers using a run-length encoded representation;

FIG. 16B is a table of a weight distribution where the weights represent first and second labels for each possible type of homopolymer;

FIG. 17 is a table of further weights of a weight distribution, which represent a categorical distribution over a set of possible lengths for each possible type of homopolymer;

FIG. 18 is a table of further weights of a weight distribution, which represent a parameterized distribution over possible lengths for each possible type of homopolymer;

FIG. 20A is a table of possible distributions that may be used to represent homopolymers;

FIG. 20B is a table of further weights of a weight distribution, which represent a categorical distribution over a set of possible lengths for each possible pair of polymer unit;

FIG. 20C is a table of further weights of a weight distribution, which represent a categorical distribution over a set of possible lengths for each possible triplet of polymer unit;

FIG. 21 is a table of a weight distribution where the set of labels is expanded to include a label corresponding to a modified polymer unit;

FIG. 22 is a table of further weights for unmodified and modified forms of a type of polymer unit in a factored representation of modifications;

FIGS. 25 to 27 are definitions of different decoding algorithms;

FIG. 28 is a definition of a further decoding algorithm;

FIG. 29 is a definition of an algorithm for constructing an objective transition matrix for a flip-flop representation;

FIG. 30 is a definition of an objective function for training over all paths;

FIG. 31 is a definition of an algorithm for constructing an objective transition matrix for a multi-stay representation;

FIG. 32 is a definition of an algorithm for constructing an objective transition matrix for a run-length encoded representation;

FIG. 37 is a table illustrating alignment of an estimated series of polymer units to a reference for representations that are trained without and with sharpening.

DETAILED DESCRIPTION

Figure 1:
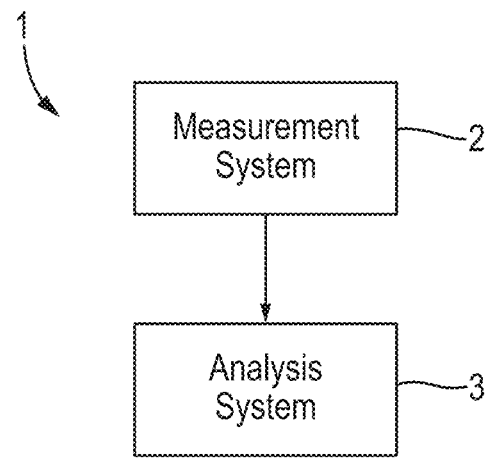
FIG. 1 is a schematic diagram of a nanopore measurement and analysis system.

A sequence of a polymer units present within a polymer may be determined using a measurement system in which the polymer is translocated through a nanopore. The measurement system may make one or more measurements during the translocation that depend in some way on the polymer units in the polymer. For example, a current across the nanopore may be measured during translocation of the polymer through the nanopore. In some cases, the measurements made by the measurement system depend on the identity of the polymer unit(s) as they translocate through the nanopore, so the signal over time allows the sequence of polymer units to be estimated. However, the signal must be decoded to estimate the underlying sequence of polymer units that produced the signal.

Such nanopore measurement systems can provide signals representing long continuous reads of polynucleotides ranging from hundreds to hundreds of thousands (and potentially more) nucleotides. This type of measurement system using a nanopore has considerable promise, particularly in the field of sequencing a polynucleotide such as DNA or RNA, and has been the subject of much recent development. However, the accuracy of estimation of the polymer units is limited by the sensitivity of the measurement system. In practice, machine learning techniques may be beneficial in producing an estimation of a polymer sequence with high accuracy.

The inventors have recognized and appreciated techniques for estimating a polymer sequence of a polymer based on a signal produced as a result of translocation of the polymer through a nanopore. The techniques analyze portions of the signal to estimate whether there was a transition in the polymer sequence during each respective portion and which units of the sequence the transition was between. As used herein, a "transition" refers to the boundary between two units (e.g., polynucleotides) of the polymer sequence, each of which may be represented by a suitable label, examples of which are provided below. Since a transition refers to a boundary between labeled units, it will be appreciated that the boundary need not be between two different labeled units, and may in some cases represent a boundary between identical labeled units.

According to some embodiments, the techniques for analyzing a signal produced as a result of translocation of the polymer through a nanopore may comprise operation of one or more neural networks into which data from the signal may be input. In some cases, such neural networks may include one or more convolutional neural network (CNNs) and/or one or more recurrent neural networks (RNNs), examples of which are discussed below.

According to some embodiments, the techniques for analyzing a signal produced as a result of translocation of the polymer through a nanopore may comprise selecting windows of a time-ordered signal. A "window" of a signal may, for instance, refer to a contiguous subset of the signal that retains the time-ordering present in the original signal. Each window may be analyzed to determine whether there was a transition in the polymer sequence in the window and which units of the sequence the transition was between. A plurality of windows of the signal may be analyzed in this manner, which may in some cases be overlapping in the time ordered sequence of measurements. For instance, a first window may be analyzed that includes the samples 1-20 in the signal, a second window may be analyzed that includes the samples 3-22, etc. In the discussion below, the number of sequential samples in a window is referred to as its "length," and the size of the step between successive windows selected for analysis is referred to as the "stride."

According to some embodiments, the techniques for analyzing a signal produced as a result of translocation of the polymer through a nanopore may comprise deriving a feature vector based on a number of samples from the signal. In some cases, a feature vector may be derived from a selected window of the signal. In some embodiments, the feature vector may be generated by a neural network wherein the samples are provided as an input to the neural network and the feature vector is output from the neural network. In some cases, such a neural network may be a CNN.

According to some embodiments, the techniques for analyzing a signal produced as a result of translocation of the polymer through a nanopore may comprise generating a plurality of weights for a portion of the signal, wherein each weight is associated with a transition between labeled units of the polymer. The weights may be indicative of a likelihood that a transition occurred between a first of the labeled units to a second of the labeled units within the portion of the signal. As one example, if the labeled units of the polymer were to correspond to polynucleotides having one of the four bases A, C, G and T, for a given portion of the signal sixteen weights may be generated each corresponding to one of the possible transitions between these four labels, A→A, A→C, etc. In some cases, a set of weights may be derived from a selected window of the signal. In some embodiments, the set of weights may be generated by a neural network wherein samples from the signal (or data derived from the samples, such as a feature vector) are provided as an input to the neural network and the weights are output from the neural network. In some cases, such a neural network may be a RNN.

According to some embodiments, the techniques for analyzing a signal produced as a result of translocation of the polymer through a nanopore may comprise performing a Bayesian analysis of a plurality of sets of weights, wherein each set of weights is associated with a particular portion of the signal. Since each set of weights is indicative of the likelihood of various transitions between labeled units occurring within a particular portion of the signal, the most likely sequence of labeled units represented by all the sets of weights together may be determined. Such a determination may comprise, for instance, a Hidden Markov Model (HMM) analysis, such as one based on the Viterbi algorithm.

In some embodiments, labeled units of the polymer may not be identical to the physical units of the polymer. Examples of such labeling are discussed below. In these cases, the most likely sequence of physical units of the polymer may be determined based on the most likely sequence of labeled units based on the known correspondence(s) between the labeling of units and the physical structures to which they correspond.

FIG. 1 illustrates a nanopore measurement and analysis system 1 comprising a measurement system 2 and an analysis system 3. In the example of FIG. 1, the measurement system 2 derives a signal from a polymer comprising a series of polymer units during translocation of the polymer with respect to a nanopore, and the analysis system 3 performs a method of analyzing the signal to derive an estimate of the series of polymer units.

According to some embodiments, the signal produced by measurement system 2 may comprise one or more electrical signals generated by the measurement system that have some dependency on the contents of the polymer that is translocated through the nanopore. In some cases, translocation of the polymer through the nanopore may generate a current within an electrical circuit of the measurement system 2 and/or may cause a voltage across electrical terminals of the measurement system to vary. Thus, the signal may represent a series of current measurements and/or voltage measurements, for example.

In some embodiments, measurement system 2 may comprise an analog-to-digital converter (ADC) and/or other means for digitizing an analog signal to produce a time-ordered series of digital measurements. The digital measurements may be provided to the analysis system 3, which may perform a plurality of operations based on the digital measurements to determine a most likely sequence of polymer units present in the polymer.

According to some embodiments, the measurement system 2 may comprise a nanopore system that comprises one or more nanopores. In a simple type, the measurement system 2 has only a single nanopore, but a more practical measurement systems 2 employ many nanopores, typically in an array, to provide parallelized collection of information. The signal may be recorded during translocation of the polymer with respect to the nanopore, typically through the nanopore. The nanopore is a pore, typically having a size of the order of nanometers, that may allow the passage of polymers therethrough. The nanopore may be a protein pore or a solid state pore. The dimensions of the pore may be such that only one polymer may translocate the pore at a time.

In general, the polymer may be of any type, for example a polynucleotide (or nucleic acid), a polypeptide such as a protein, or a polysaccharide. The polymer may be natural or synthetic. The polynucleotide may comprise a homopolymer region. The homopolymer region may comprise between 5 and 15 nucleotides.

In the case of a polynucleotide or nucleic acid, the polymer units may be nucleotides. The nucleic acid is typically deoxyribonucleic acid (DNA), ribonucleic acid (RNA), cDNA or a synthetic nucleic acid known in the art, such as peptide nucleic acid (PNA), glycerol nucleic acid (GNA), threose nucleic acid (TNA), locked nucleic acid (LNA) or other synthetic polymers with nucleotide side chains. The PNA backbone is composed of repeating N-(2-aminoethyl)-glycine units linked by peptide bonds. The GNA backbone is composed of repeating glycol units linked by phosphodiester bonds. The TNA backbone is composed of repeating threose sugars linked together by phosphodiester bonds. LNA is formed from ribonucleotides as discussed above having an extra bridge connecting the 2' oxygen and 4' carbon in the ribose moiety. The nucleic acid may be single-stranded, be double-stranded or comprise both single-stranded and double-stranded regions. The nucleic acid may comprise one strand of RNA hybridized to one strand of DNA. Typically cDNA, RNA, GNA, TNA or LNA are single stranded.

The polymer units may be any type of nucleotide. The nucleotide can be naturally occurring or artificial. For instance, the method may be used to verify the sequence of a manufactured oligonucleotide. A nucleotide typically contains a nucleobase, a sugar and at least one phosphate group. The nucleobase and sugar form a nucleoside. The nucleobase is typically heterocyclic. Suitable nucleobases include purines and pyrimidines and more specifically adenine, guanine, thymine, uracil and cytosine. The sugar is typically a pentose sugar. Suitable sugars include, but are not limited to, ribose and deoxyribose. The nucleotide is typically a ribonucleotide or deoxyribonucleotide. The nucleotide typically contains a monophosphate, diphosphate or triphosphate.

The nucleotide can be a modified base, such as a damaged or epigenetic base. For instance, the nucleotide may comprise a pyrimidine dimer. Such dimers are typically associated with damage by ultraviolet light and are the primary cause of skin melanomas. The nucleotide can be labelled or modified to act as a marker with a distinct signal. This technique can be used to identify the absence of a base, for example, an abasic unit or spacer in the polynucleotide. The method could also be applied to any type of polymer.

In the case of a polypeptide, the polymer units may be amino acids that are naturally occurring or synthetic. In the case of a polysaccharide, the polymer units may be monosaccharides. Particularly where the measurement system 2 comprises a nanopore and the polymer comprises a polynucleotide, the polynucleotide may be long, for example at least 5 kB (kilo-bases), i.e., at least 5,000 nucleotides, or at least 30 kB (kilo-bases), i.e., at least 30,000 nucleotides, or at least 100 kB (kilo-bases), i.e., at least 100,000 nucleotides.

Where the nanopore is a protein pore, it may have the following properties. The biological pore may be a transmembrane protein pore. Transmembrane protein pores for use in accordance with the invention can be derived from β-barrel pores or α-helix bundle pores. β-barrel pores comprise a barrel or channel that is formed from β-strands. Suitable β-barrel pores include, but are not limited to, β-toxins, such as α-hemolysin, anthrax toxin and leukocidins, and outer membrane proteins/porins of bacteria, such as *Mycobacterium smegmatis* porin (Msp), for example MspA, MspB, MspC or MspD, lysenin, outer membrane porin F (OmpF), outer membrane porin G (OmpG), outer membrane phospholipase A and *Neisseria* autotransporter lipoprotein (NalP). α-helix bundle pores comprise a barrel or channel that is formed from α-helices. Suitable α-helix bundle pores include, but are not limited to, inner membrane proteins and a outer membrane proteins, such as WZA and ClyA toxin. The transmembrane pore may be derived from Msp or from α-hemolysin (α-HL). The transmembrane pore may be derived from lysenin. Suitable pores derived from lysenin are disclosed in WO 2013/153359. Suitable pores derived from MspA are disclosed in WO-2012/107778. The pore may be derived from CsgG, such as disclosed in WO-2016/034591. The pore may be a DNA origami pore.

The protein pore may be a naturally occurring pore or may be a mutant pore. Typical pores are described in WO-2010/109197, Stoddart D et al., Proc Natl Acad Sci, 12; 106(19): 7702-7, Stoddart D et al., Angew Chem Int Ed Engl. 2010; 49(3):556-9, Stoddart D et al., Nano Lett. 2010 Sep. 8; 10(9):3633-7, Butler T Z et al., Proc Natl Acad Sci 2008; 105(52):20647-52, and WO-2012/107778. The protein pore may be one of the types of protein pore described in WO-2015/140535 and may have the sequences that are disclosed therein.

The protein pore may be inserted into an amphiphilic layer such as a biological membrane, for example a lipid bilayer. An amphiphilic layer is a layer formed from amphiphilic molecules, such as phospholipids, which have both hydrophilic and lipophilic properties. The amphiphilic layer may be a monolayer or a bilayer. The amphiphilic layer may be a co-block polymer such as disclosed in Gonzalez-Perez et al., Langmuir, 2009, 25, 10447-10450 or WO2014/064444. Alternatively, a protein pore may be inserted into an aperture provided in a solid state layer, for example as disclosed in WO2012/005857.

A suitable apparatus for providing an array of nanopores is disclosed in WO-2014/064443. The nanopores may be provided across respective wells wherein electrodes are provided in each respective well in electrical connection with an ASIC for measuring current flow through each nanopore. A suitable current measuring apparatus may comprise the current sensing circuit as disclosed in WO-2016/181118.

The nanopore may comprise an aperture formed in a solid state layer, which may be referred to as a solid state pore. The aperture may be a well, gap, channel, trench or slit provided in the solid state layer along or into which analyte may pass. Such a solid-state layer is not of biological origin. In other words, a solid state layer is not derived from or isolated from a biological environment such as an organism or cell, or a synthetically manufactured version of a biologically available structure. Solid state layers can be formed from both organic and inorganic materials including, but not limited to, microelectronic materials, insulating materials such as $Si_3N_4$, $Al_2O_3$, and SiO, organic and inorganic polymers such as polyamide, plastics such as Teflon® or elastomers such as two-component addition-cure silicone rubber, and glasses. The solid state layer may be formed from graphene. Suitable graphene layers are disclosed in WO-2009/035647, WO-2011/046706 or WO-2012/138357. Suitable methods to prepare an array of solid state pores is disclosed in WO-2016/187519.

Such a solid state pore is typically an aperture in a solid state layer. The aperture may be modified, chemically, or otherwise, to enhance its properties as a nanopore. A solid state pore may be used in combination with additional components which provide an alternative or additional measurement of the polymer such as tunneling electrodes (Ivanov A P et al., Nano Lett. 2011 Jan. 12; 11(1):279-85), or a field effect transistor (FET) device (as disclosed for example in WO-2005/124888). Solid state pores may be formed by known processes including for example those described in WO-00/79257. The nanopore may be a hybrid of a solid state pore with a protein pore.

The measurement system 2 takes a series of measurements of a property that depends on the polymer units translocating with respect to the pore may be measured. The series of measurements form a signal. The property that is measured may be associated with an interaction between the polymer and the pore. Such an interaction may occur at a constricted region of the pore.

In one type of measurement system 2, a property that is measured may be the ion current flowing through a nanopore. These and other electrical properties may be measured using single channel recording equipment as describe in Stoddart D et al., Proc Natl Acad Sci, 12; 106(19):7702-7, Lieberman K R et al, J Am Chem Soc. 2010; 132(50):17961-72, and WO-2000/28312. Alternatively, measurements of electrical properties may be made using a multi-channel system, for example as described in WO-2009/077734, WO-2011/067559 or WO-2014/064443.

Ionic solutions may be provided on either side of the membrane or solid state layer, which ionic solutions may be present in respective compartments. A sample containing the polymer analyte of interest may be added to one side of the membrane and allowed to move with respect to the nanopore, for example under a potential difference or chemical gradient. The signal may be derived during the movement of the polymer with respect to the pore, for example taken during translocation of the polymer through the nanopore. The polymer may partially translocate the nanopore.

In order to allow measurements to be taken as the polymer translocates through a nanopore, the rate of translocation can be controlled by a polymer binding moiety. Typically the moiety can move the polymer through the nanopore with or against an applied field. The moiety can be a molecular motor using for example, in the case where the moiety is an enzyme, enzymatic activity, or as a molecular brake. Where the polymer is a polynucleotide there are a number of methods proposed for controlling the rate of translocation including use of polynucleotide binding enzymes. Suitable enzymes for controlling the rate of translocation of polynucleotides include, but are not limited to, polymerases, helicases, exonucleases, single stranded and double stranded binding proteins, and topoisomerases, such as gyrases. For other polymer types, moieties that interact with that polymer type can be used. The polymer interacting moiety may be any disclosed in WO-2010/086603, WO-2012/107778, and Lieberman K R et al, J Am Chem Soc. 2010; 132(50):17961-72), and for voltage gated schemes (Luan B et al., Phys Rev Lett. 2010; 104(23):238103).

The polymer binding moiety can be used in a number of ways to control the polymer motion. The moiety can move the polymer through the nanopore with or against the applied field. The moiety can be used as a molecular motor using for example, in the case where the moiety is an enzyme, enzymatic activity, or as a molecular brake. The translocation of the polymer may be controlled by a molecular ratchet that controls the movement of the polymer through the pore. The molecular ratchet may be a polymer binding protein. For polynucleotides, the polynucleotide binding protein is preferably a polynucleotide handling enzyme. A polynucleotide handling enzyme is a polypeptide that is capable of interacting with and modifying at least one property of a polynucleotide. The enzyme may modify the polynucleotide by cleaving it to form individual nucleotides or shorter chains of nucleotides, such as di- or trinucleotides. The enzyme may modify the polynucleotide by orienting it or moving it to a specific position. The polynucleotide handling enzyme does not need to display enzymatic activity as long as it is capable of binding the target polynucleotide and controlling its movement through the pore. For instance, the enzyme may be modified to remove its enzymatic activity or may be used under conditions which prevent it from acting as an enzyme. Such conditions are discussed in more detail below.

Preferred polynucleotide handling enzymes are polymerases, exonucleases, helicases and topoisomerases, such as gyrases. The polynucleotide handling enzyme may be for example one of the types of polynucleotide handling enzyme described in WO-2015/140535 or WO-2010/086603.

Translocation of the polymer through the nanopore may occur, either cis to trans or trans to cis, either with or against an applied potential. The translocation may occur under an applied potential which may control the translocation.

Exonucleases that act progressively or processively on double stranded DNA can be used on the cis side of the pore to feed the remaining single strand through under an applied potential or the trans side under a reverse potential. Likewise, a helicase that unwinds the double stranded DNA can also be used in a similar manner. There are also possibilities for sequencing applications that require strand translocation against an applied potential, but the DNA must be first "caught" by the enzyme under a reverse or no potential. With the potential then switched back following binding the strand will pass cis to trans through the pore and be held in an extended conformation by the current flow. The single strand DNA exonucleases or single strand DNA dependent polymerases can act as molecular motors to pull the recently translocated single strand back through the pore in a controlled stepwise manner, trans to cis, against the applied potential. Alternatively, the single strand DNA dependent polymerases can act as a molecular brake slowing down the movement of a polynucleotide through the pore. Any moieties, techniques or enzymes described in WO-2012/107778 or WO-2012/033524 could be used to control polymer motion.

Similarly, the properties that are measured may be of types other than ion current. Some examples of alternative types of property include without limitation: electrical properties and optical properties. A suitable optical method involving the measurement of fluorescence is disclosed by J. Am. Chem. Soc. 2009, 131 1652-1653. Possible electrical properties include: ionic current, impedance, a tunneling property, for example tunneling current (for example as disclosed in Ivanov A P et al., Nano Lett. 2011 Jan. 12; 11(1):279-85), and a FET (field effect transistor) voltage (for example as disclosed in WO2005/124888). One or more optical properties may be used, optionally combined with electrical properties (Soni G V et al., Rev Sci Instrum. 2010 January; 81(1):014301). The property may be a transmembrane current, such as ion current flow through a nanopore. The ion current may typically be the DC ion current, although in principle an alternative is to use the AC current flow (i.e., the magnitude of the AC current flowing under application of an AC voltage).

Figure 2:
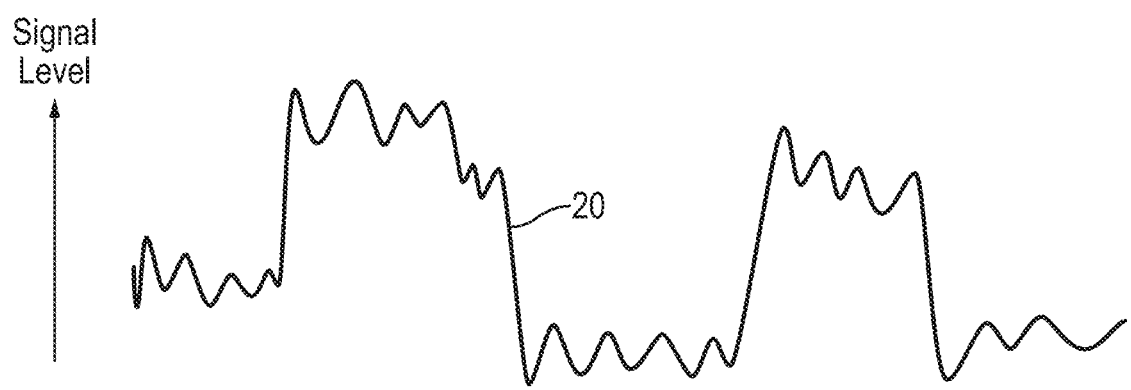
FIG. 2 is a plot of a typical signal over time.

In some types of the measurement system 2, the signal may be characterized as comprising measurements from a series of events, where each event provides a group of measurements. FIG. 2 illustrates a typical example of such a signal in the case of the measurement system 2 producing a time ordered series of current measurements. The group of measurements from each event have a level that is similar, although subject to some variance. This may be thought of as a noisy step wave with each step corresponding to an event. The events may have biochemical significance, for example arising from a given state or interaction of the measurement system 2. This may in some instances arise from translocation of the polymer through the nanopore occurring in a ratcheted manner. However, this type of signal is not produced by all types of measurement system and the methods described herein are not dependent on the type of signal. For example, when translocation rates approach the measurement sampling rate, for example, measurements are taken at 1 times, 2 times, 5 times or 10 times the translocation rate of a polymer unit, events may be less evident or not present, compared to slower sequencing speeds or faster sampling rates.

In addition, where events are present, typically there is no a priori knowledge of number of measurements in the group, which varies unpredictably. These factors of variance and lack of knowledge of the number of measurements can make it hard to distinguish some of the groups, for example where the group is short and/or the levels of the measurements of two successive groups are close to one another.

The group of measurements corresponding to each event typically has a level that is consistent over the time scale of the event, but for most types of the measurement system 2 will be subject to variance over a short time scale. Such variance can result from measurement noise, for example arising from the electrical circuits and signal processing, notably from the amplifier in the particular case of electrophysiology. Such measurement noise is inevitable due to the small magnitude of the properties being measured. Such variance can also result from inherent variation or spread in the underlying physical or biological system of the measurement system 2, for example a change in interaction, which might be caused by a conformational change of the polymer.

Most types of the measurement system 2 will experience such inherent variation to greater or lesser extents. For any given types of the measurement system 2, both sources of variation may contribute or one of these noise sources may be dominant.

With increase in the sequencing rate, being the rate at which polymer units translocate with respect to the nanopore, then the events may become less pronounced and hence harder to identify, or may disappear. Thus, analysis methods that rely on detecting such events detection may become less efficient at as the sequencing rate increases.

However, the methods disclosed herein are not dependent on detecting such events. The methods described below are effective even at relatively high sequencing rates, including sequencing rates at which the polymer translocates at a rate of at least 10 polymer units per second, preferably 100 polymer units per second, more preferably 500 polymer units per second, or more preferably 1000 polymer units per second.

As discussed above, measurement system 2 may be configured to digitize analog measurements produced by translocation of the polymer through a nanopore. The resulting digital signal, being a time-ordered series of digital measurements, has a sample rate that is a rate of digital measurements with respect to the time over which the corresponding analog measurements were taken. Typically, the sample rate is higher than the sequencing rate. For example, the sample rate may be in a range from a 100 Hz to 30 kHz, but this is not limitative. For example, each second of an analog signal produced by the measurement system may be digitized into 100 values (at a sample rate of 100 Hz) or may be digitized into 30,000 values (at a sample rate of 30 kHz). In practice the sample rate may depend on the nature of the measurement system 2.

In some cases, operations performed by the analysis system 3 may be based on plural series of measurements that are measurements of series of polymer units that are related. For example, the plural series of measurements may be series of measurements of separate polymers having related sequences, or may be series of measurements of different regions of the same polymer having related sequences.

In the case of polynucleotides, the plural series of polymer units may be related by being complementary, so that one series of polymer units is referred to as a template and the other series of polymer units that is a complementary thereto is referred to as a complement.

In this case, measurements of the template and the complement may be taken using any suitable technique, for example being taken sequentially using a polynucleotide binding protein or via polynucleotide sample preparation.

The series of measurements form a raw signal that is analyzed by the analysis system 3. The raw signal may be pre-processed in the measurement system 2 before supply to the analysis system 2 or as an initial stage in the analysis system 3, for example filtered to reduce noise. In such cases, the analysis below is performed on the pre-processed signal.

The analysis system 3 may be physically associated with the measurement system 2, and may also provide control signals to the measurement system 2. In that case, the nanopore measurement and analysis system 1 comprising the measurement system 2 and the analysis system 3 may be arranged as disclosed in any of WO-2008/102210, WO-2009/07734, WO-2010/122293, WO-2011/067559 or WO-2014/04443.

Alternatively, the analysis system 3 may be implemented in a separate apparatus, in which case the series of measurement is transferred from the measurement system 2 to the analysis system 3 by any suitable means, typically a data network. For example, one convenient cloud-based implementation is for the analysis system 3 to be a server to which the input signal 11 is supplied over the internet.

The analysis system 3 may be implemented by a computer apparatus executing a computer program or may be implemented by a dedicated hardware device, or any combination thereof. In either case, the data used by the method is stored in a memory in the analysis system 3. In the case of a computer apparatus executing a computer program, the computer apparatus may be any type of computer system but is typically of conventional construction. The computer program may be written in any suitable programming language. The computer program may be stored on a (non-transitory) computer-readable storage medium, which may include any volatile and/or non-volatile storage medium or media, of any type. For example: a recording medium which is insertable into a drive of the computing system and which may store information magnetically, optically or opto-magnetically; a fixed recording medium of the computer system such as a hard drive; and/or a computer memory.

In the case of the computer apparatus being implemented by a dedicated hardware device, then any suitable type of device may be used, for example an FPGA (field programmable gate array) or an ASIC (application specific integrated circuit). In a preferred embodiment, portions of the computer program may be implemented using hardware amenable to parallelization of calculations such as a Graphics processing unit (GPU).

Figure 3:
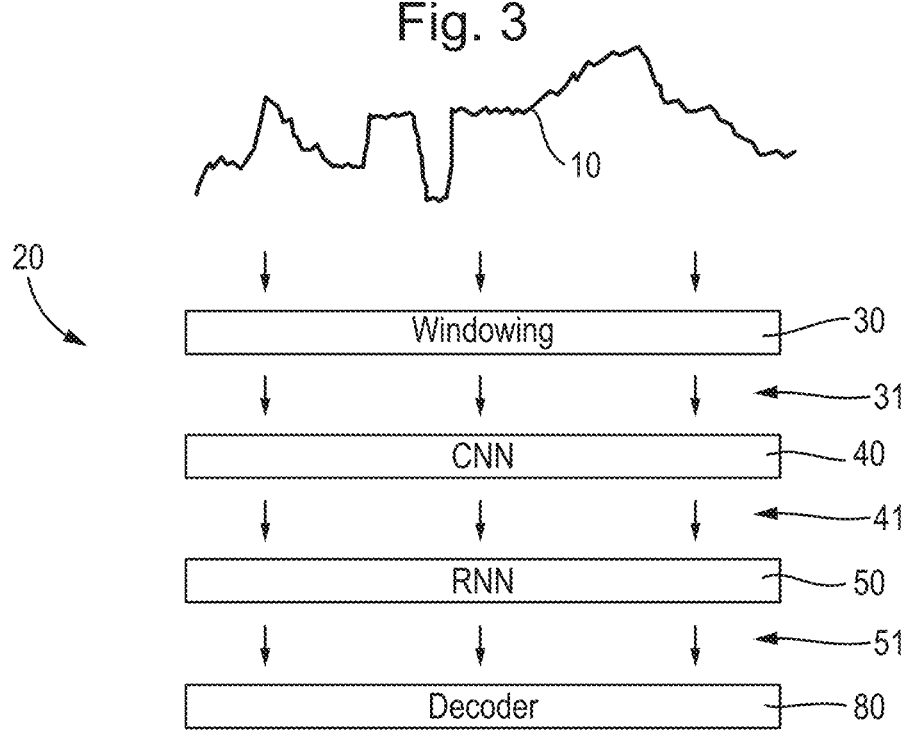
FIG. 3 is a diagram of a neural network in an analysis system.

FIG. 3 illustrates a method of operating the nanopore measurement and analysis system 1 to determine a most likely sequence of polymer units within a polymer. In the method of FIG. 3, an analysis is performed by analysis system 3 discussed above based on a signal representing measurements taken during translocation of the polymer through a nanopore.

In the example of FIG. 3, a signal 10 is obtained by the analysis system 3, such as by reception from the measurement system 2 and/or by reading data from a computer readable storage medium. The signal 10 may be produced by the measurement system 2. For example, as discussed above, a polymer may be translocated with respect to the pore, for example through the pore, and the signal is produced by electronics components of the measurement system during the translocation of the polymer. In some cases, the polymer may be caused to translocate with respect to the pore by providing conditions that permit the translocation of the polymer, whereupon the translocation may occur spontaneously. As further discussed above, signal 10 may be a time-ordered series of digital measurements generated by the measurement system 2. For instance, an analog signal produced by measuring one or more electrical characteristics of the nanopore system (e.g., voltage and/or current across a nanopore) may be digitized by the measurement system to produce signal 10.

Irrespective of how the analysis system 3 obtains the signal 10, the analysis system 3 performs a method of analyzing the signal 10 as will now be described.

In the example of FIG. 3, the analysis system 3 performs an analysis of signal 10 by executing a number of processing operations 20, which includes windowing operation(s) 30, execution of a convolutional neural network (CNN) 40, execution of a recurrent neural network (RNN) 50, and a decoder 80. It will be appreciated that while CNN 40 and RNN 50 are described in the below as being two separate neural networks, in some implementations a single neural network may instead be executed that comprises one or more convolutional layers in addition to one or more recurrent layers.

Figure 4:
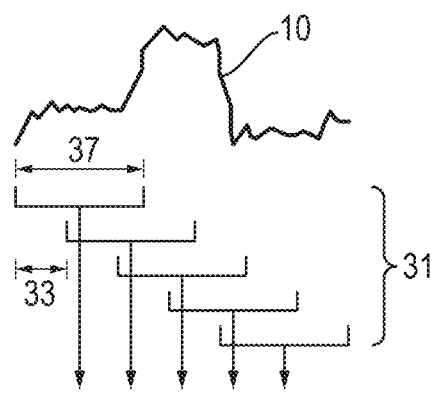
FIG. 4 is a plot of part of the signal illustrating the operation of a windowing section of the neural network.

In the example of FIG. 3, the windowing unit 30 windows the signal 10 to derive successive windowed sections 31 of the signal 10, for example as illustrated in FIG. 4. The windowed sections 11 are supplied to the CNN 40. As discussed above, a window of a signal may refer to a contiguous subset of the signal that retains the time-ordering present in the original signal. For instance, a first window may be analyzed that includes the samples 1-20 in the signal, a second window may be analyzed that includes the samples 3-22, etc. In the discussion below, the number of sequential samples in a window is referred to as its "length," and the size of the step between successive windows selected for analysis is referred to as the "stride."

As shown in FIG. 4, the windowed sections 31 of signal 10 have a length 32, and a stride 33 between successive windowed sections 31, both of which may be counted in time or in numbers of samples of the signal 10. The stride 33 may be a single sample or plural samples. If the stride 33 is larger than a single sample, then the windowing unit 30 may be considered to effectively perform downsampling of the signal, since there are less windowed sections 31 than samples in the signal 10. Typically, the stride 33 is less than the length 33, such that the windowed sections 10 overlap in the signal 10.

In some embodiments, the length 32 may be equal to or greater than 2, 5, 10, 15, 20, 25, 50, or 100 samples. In some embodiments, the length 32 may be less than or equal to 200, 100, 50, 25, 20, 15, 10, or 5 samples. Any suitable combinations of the above-referenced ranges are also possible (e.g., a length equal to or greater than 5 and less than or equal to 20). In some embodiments, the stride 33 may be equal to or greater than 1, 2, 3, 4, 5, 6, 7, 8, 9 or 10 samples. In some embodiments, the stride 33 may be less than or equal to 10, 9, 8, 7, 6, 5, 4, 3, or 2 samples. Any suitable combinations of the above-referenced ranges are also possible (e.g., a stride equal to or greater than 2 and less than or equal to 5). The length and stride may also be expressed in units of time, which correspond to the above values expressed in numbers of samples based on the sample rate of signal 10. In some embodiments, the sample rate of signal 10 may be equal to or greater than 100 Hz, 1 kHz, 5 kHz, 20 kHz, 30 kHz, 50 kHz, or 100 kHz. In some embodiments, the sample rate of signal 10 may be less than or equal to 200 kHz, 100 kHz, 50 kHz, 30 kHz, 20 kHz, 10 kHz or 5 kHz. Any suitable combinations of the above-referenced ranges are also possible (e.g., a sample rate of equal to or greater than 5 kHz and less than or equal to 20 kHz). In addition, any suitable combination of the above length and stride values may be instead expressed at any of the above sample rates (e.g., a stride of a stride equal to or greater than 0.02 s and less than or equal to 0.05 s for a signal at 100 Hz, etc.).

In the example of FIG. 4, the CNN 40 comprises at least one convolutional layer. The at least one convolutional layer performs a convolution of each windowed section 11 to derive a feature vector 41 for each windowed section 31. That is, the input to the CNN 40 includes a time-ordered series of measurements as selected by the windowing unit 30, and the output of the CNN includes a feature vector. By repeatedly executing the CNN for each windowed section of the input signal 10, a plurality of feature vectors may be generated, with each feature vector corresponding to a respective windowed section of the input signal. In some embodiments, the CNN may be executed for each window irrespective of any events that may be evident in the signal, and so is equally applicable to signals where such events are or are not evident, or to signals where events are provided during pre-processing.

According to some embodiments, the CNN 40 may include a single convolutional layer, defined by an affine transform with weights A and bias b, and an activation function g. Here $I_{t-j:t+k}$ represents a window of measurements of the raw signal 20 containing the t−j to the t+k measurements inclusive, and $O_t$ is the output feature vector. The integer t is used as an index and the values j and k are integers that together represent the length of the window of measurements (i.e., length=j+k).

$$y_t = b + A I_{t-j:t+k} \quad \text{Affine Transform}$$

$$O_t = g(y_t) \quad \text{Activation}$$

The activation function g may for instance be the hyperbolic tangent, the Rectifying Linear Unit (ReLU), Exponential Linear Unit (ELU), softplus unit, and sigmoidal unit. Plural convolutional layers may also be used.

It may be noted that the vector $y_t$ may contain a number of elements that is different from the number of values in $I_{t-j:t+k}$; in general, the dimensions of the weight matrix A and the dimensions of $I_{t-j:t+k}$ determine the dimensions of $y_t$. In some embodiments, for instance, the feature vector $y_t$ have contain 96 elements, 256 elements, or 512 elements irrespective of how many measurement values are present within $I_{t-j:t+x}$.

The single layer convolutional network as described above may have a disadvantage that there is a dependence on the exact position of detected features in the raw signal and this also implies a dependence on the spacing between the features. According to some embodiments, this dependence can be alleviated by using the output sequence of feature vectors generated by the first convolution layer as input into a second 'pooling' layer that acts on the order statistics of its input. That is, a filter is applied by the pooling layer to a sorted version of the input vector (e.g., the feature vector) based on a selected order statistic. For instance, one type of filter might pick out only the highest value in the feature vector by selecting the first element of the vector after the vector has been sorted from highest to lowest values. Other examples include picking the lowest value, selecting all values normalized by the number of values in the vector, picking the middle (median) value in the vector, or combinations thereof.

As one example in which the pooling layer is a single layer of the neural network 40, the following equations describe how the output of the pooling layer relates to the input vectors. Letting f be an index over input features, so $A_f$ is the weight matrix for feature f, and let $\mathcal{S}$ be a functor that returns some or all of the order statistics of its input:

$y_t = b + \Sigma_f A_f \mathcal{S} (I_{f,t-j:t+k})$ Affine Transform $O_t = g(y_t)$ Activation For instance, when the filter of the pooling layer is based on returning the maximum value obtained for each respective feature, we may let functor $\mathcal{S}_M$ return only the last order statistic, being the maximum value obtained in its input, and let $U_f$ be the (single column) matrix that consists entirely of zeros other than a unit value at its (f, 1) element:

$y_t = b + \Sigma_f U_f \mathcal{S}_M(I_{f,t-j:t+k})$ Affine Transform $O_t = g(y_t)$ Activation Since the matrices $U_f$ are extremely sparse, for reasons of computation efficiency, the matrix multiplications may be performed implicitly: here effect of $\Sigma_f U_f x_f$ is to set element f of the output feature vector to $x_f$.

The convolutions and/or pooling may be performed only calculating their output for every nth position (a stride of n) and so down-sampling their output. Down-sampling can be advantageous from a computational perspective since the rest of the network has to process fewer blocks (faster compute) to achieve a similar accuracy.

Adding a stack of convolution layers solves many of the problems described above: the feature detection learned by the convolution can function both as nanopore-specific feature detectors and summary statistics without making any additional assumptions about the system; feature uncertainty is passed down into the rest of the network by relative weights of different features and so further processing can take this information into account leading to more precise predictions and quantification of uncertainty.

Figure 5:
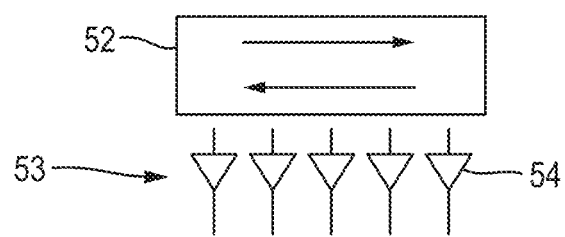
FIG. 5 is a diagram of a recurrent layer of an RNN.

Returning to FIG. 3, irrespective of the particular manner by which CNN 40 calculated the feature vectors, these are input to the RNN 50, which outputs a set of weight values for each input feature vector. According to some embodiments, the RNN 50 may comprise at least one recurrent layer with each recurrent layer being followed by a feed-forward layer. FIG. 5 illustrates this approach for the case of a single recurrent layer 52 in the RNN, whereas in general there may be any plural number of recurrent layers 52 and subsequent feed-forward layers 53. This approach may provide a flexible choice of unit architecture. The layers may have different parameters, be different sizes and/or even be composed of different unit types.

The recurrent layer 52 is preferably bidirectional to allow the influence of each input feature vector to propagate in both directions through the RNN. An alternative preferred embodiment comprises multiple uni-directional recurrent layers, arranged in alternating directions, for example layers arranged in successive directions of reverse, forwards, reverse, forwards, reverse. These bidirectional architectures allow the RNN 50 to accumulate and propagate information in a manner unavailable to HMMs. An additional advantage of recurrent layers is that they do not require an exact scaling of signal to model (or vice versa), e.g., via an iterative procedure.

For the subsampling in the feed-forward layer 53, separate affine transforms may be applied to the output vectors for the forward and backwards layer at each column, followed by summation; this is equivalent to applying an affine transform to the vector formed by concatenation of the input and output. An activation function is then applied element-wise to the resultant matrix.

The recurrent layers 52 may comprise one or more of any of several types of neural network unit as will now be described. The types of unit fall into two general categories depending on whether or not they are 'recurrent'. Whereas non-recurrent units treat each step in the sequence independently, a recurrent unit is designed to be used in a sequence and pass a state vector from one step to the next.

Figure 6:
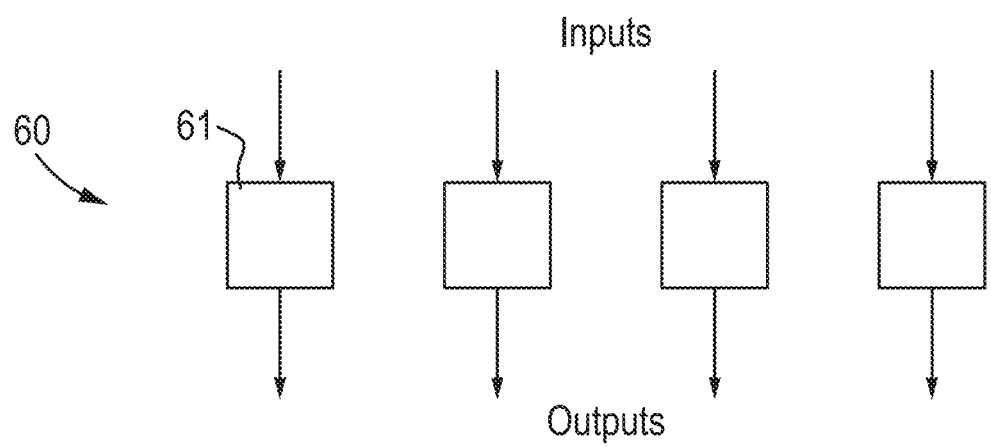
FIG. 6 is a diagram of a non-recurrent layer.
Figure 7:
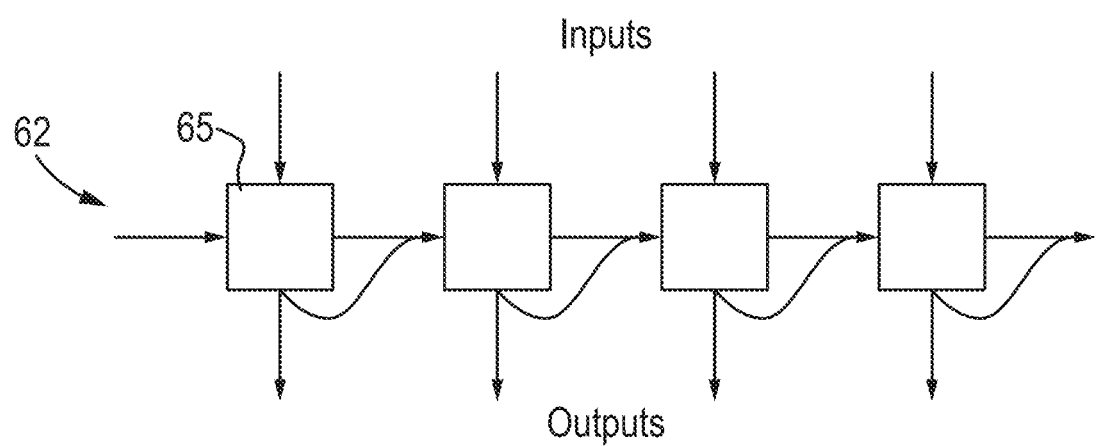
FIG. 7 is a diagram a unidirectional layer.
Figure 8:
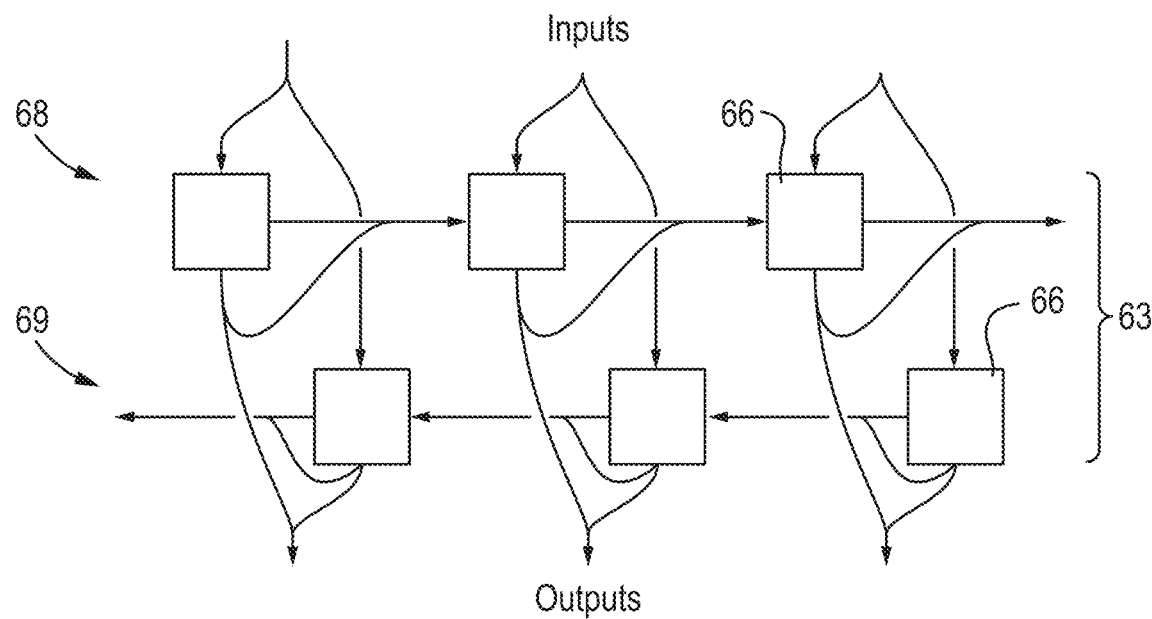
FIG. 8 is a diagram of a bidirectional recurrent layer that combines a 'forward' and 'backward' recurrent layer.
Figure 9:
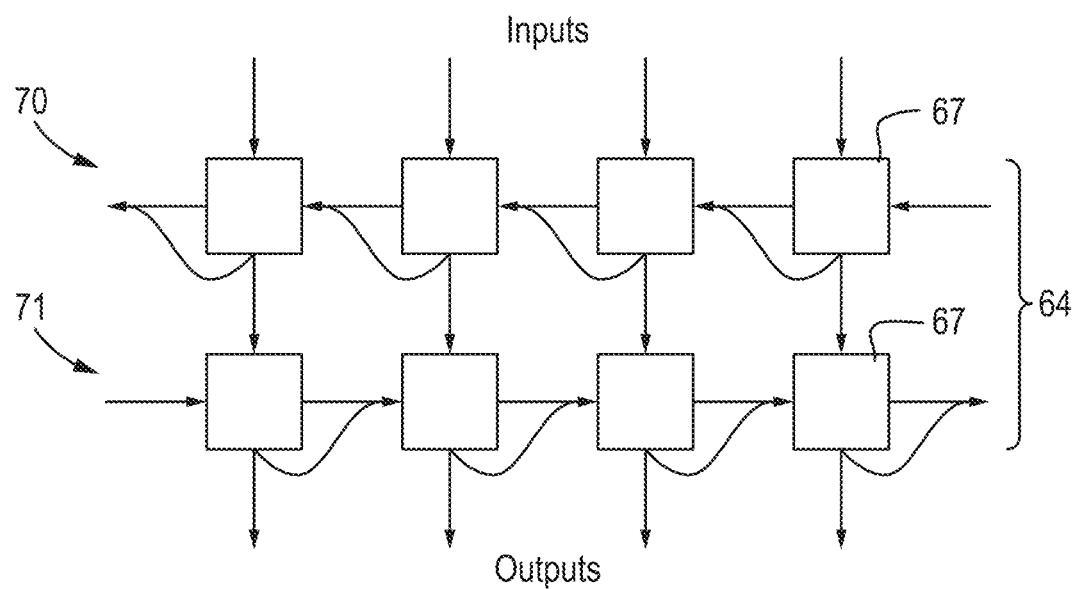
FIG. 9 is a diagram of an alternative bidirectional recurrent layer that combines 'forward' and 'backward' recurrent layer in an alternating fashion.

In order to show diagrammatically the difference between non-recurrent units and recurrent units, FIG. 6 shows a non-recurrent layer 60 of non-recurrent units 61 and FIGS. 7 to 9 show three different layers 62 to 64 of respective non-recurrent units 64 to 66. In each of FIGS. 6 to 9, the arrows show connections along which vectors are passed, arrows that are split being duplicated vectors and arrows which are combined being concatenated vectors.

In the non-recurrent layer 60 of FIG. 6, the non-recurrent units 61 have separate inputs and outputs which do not split or concatenate. The recurrent layer 62 of FIG. 7 is a unidirectional recurrent layer in which the output vectors of the recurrent units 65 are split and passed to unidirectionally to the next recurrent unit 65 in the recurrent layer. While not a discrete unit in its own right, the bidirectional recurrent layers 63 and 64 of FIGS. 8 and 9 each have a repeating unit-like structure made from simpler recurrent units 66 and 67, respectively.

In the bidirectional recurrent layer of FIG. 8, the bidirectional recurrent layer 63 consists of two sub-layers 68 and 69 of recurrent units 66, being a forwards sub-layer 68 having the same structure as the unidirectional recurrent layer 62 of FIG. 7 and a backward sub-layer 69 having a structure that is reversed from the unidirectional recurrent layer 62 of FIG. 7 as though time were reversed, passing state vectors from one unit 66 to the previous unit 66. Both the forwards and backwards sub-layers 68 and 69 receive the same input and their outputs from corresponding units 66 are concatenated together to form the output of the bidirectional recurrent layer 63. It is noted that there are no connections between any unit 66 within the forwards sub-layer 68 and any unit within the backwards sub-layer 69.

The alternative bidirectional recurrent layer 64 of FIG. 9 similarly consists of two sub-layers 70 and 71 of recurrent units 67, being a forwards sub-layer 68 having the same structure as the unidirectional recurrent layer 62 of FIG. 7 and a backwards sub-layer 69 having a structure that is reversed from the unidirectional recurrent layer 62 of FIG. 7 as though time were reversed. Again the forwards and backwards sub-layers 68 and 69 receive the same inputs, However, in contrast to the bidirectional recurrent layer of FIG. 8, the outputs of forwards sub-layer 68 are the inputs of the backwards sub-layer 69 and the outputs of the backwards sub-layer 69 form the output of the bidirectional recurrent layer 64 (the forwards and backwards sub-layers 68 and 69 could be reversed).

A generalization of the bidirectional recurrent layer shown in FIG. 9 would be a stack of recurrent layers consisting of plural 'forwards' and 'backward' recurrent sub-layers, where the output of each layer is the input for the next layer.

The bidirectional recurrent layers 52 of the RNN 50 may take the form of either of the bidirectional recurrent layers 63 and 64 of FIGS. 8 and 9. In general, the bidirectional recurrent layers 34 of FIG. 3 could be replaced by a non-recurrent layer, for example the non-recurrent layer 60 of FIG. 6, or by a unidirectional recurrent layer, for example the recurrent layer 62 of FIG. 7, but improved performance is achieved by use of bidirectional recurrent layers 34.

The feed-forward layers of the RNN 50 (e.g., feed-forward layer 53 of FIG. 5) will now be described. According to some embodiments, the feed-forward layers of the RNN 50 comprise feed-forward units that process respective vectors. The feed-forward units may be conventional feed-forward units in which an affine transform is applied to the input vector and then a non-linear function is applied element-wise to the result. In the case of RNN 50, the feed-forward layers may all use the hyperbolic tangent for the non-linear function, although many others may be used with little variation in the overall accuracy of the network.

For instance, if the input vector at step t is $I_t$, and the weight matrix and bias for the affine transform are A and b respectively, then the output vector $O_t$ is:

$$y_t = b + A I_t \quad \text{Affine transform}$$

$$O_t = \tan h(y_t) \quad \text{Non-linearity}$$

The weight distributions of the RNN 50 may in some cases be normalized globally. This is discussed in more detail below.

In some embodiments, the non-recurrent units 62 and recurrent units 65 to 67 treat each event independently, but may be replaced by Long Short-Term Memory units having a form as will now be described. A Long Short-Term Memory (LSTM) unit is a recurrent unit and so passes a state vector from one step in the sequence to the next. The LSTM is based around the notion that the unit is a memory cell: a hidden state containing the contents of the memory is passed from one step to the next and operated on via a series of gates that control how the memory is updated. One gate controls whether each element of the memory is wiped (forgotten), another controls whether it is replaced by a new value, and a final gate that determines whether the memory is read from and output. What makes the memory cell differentiable is that the binary on/off logic gates of the conceptual computer memory cell are replaced by notional probabilities produced by a sigmoidal function and the contents of the memory cells represent an expected value.

In the below, the implementation of the LSTM is described along with a 'peep-hole' modification.

For the non-modified LSTM, the probabilities associated with the different operations on the LSTM units are defined by the following set of equations. Letting $I_t$ be input vector for step t, $O_t$ be the output vector and let the affine transform indexed by x that has bias $b_x$ and weight matrices $W_{xI}$ and $W_{xO}$ for the input and previous output respectively; $\sigma$ is the non-linear sigmoidal transformation.

$$f_t = \sigma(W_{fI} I_t + W_{fO} O_{t-1} + b_f) \quad \text{Forget probability}$$

$$u_t = \sigma(W_{uI} I_t + W_{uO} O_{t-1} + b_u) \quad \text{Update probability}$$

$$o_t = \sigma(W_{oI} I_t + W_{oO} O_{t-1} + b_o) \quad \text{Output probability}$$

Given the update vectors defined above and letting the · operator represent element-wise (Hadamard) multiplication, the equations to update the internal state $StS_t$ and determine the new output are:

$$v_t = \tan h(W_{vI} I_t + W_{vO} O_{t-1} + b_v) \quad \text{Value to update with}$$

$$S_t = S_{t-1} \cdot f_t + v_t \cdot u_t \quad \text{Update memory cell}$$

$$O_t = \tan h(s_t) \cdot o_t \quad \text{Read from memory cell}$$

The peep-hole modification of an LSTM is as follows. The 'peep-hole' modification adds some additional connections to the LSTM architecture allowing the forget, update and output probabilities to 'peep at' (be informed by) the hidden state of the memory cell. The update equations for the network are as above but, letting $P_x$ be a 'peep' vector of length equal to the hidden state, the three equations for the probability vectors become:

$$f_t = \sigma(W_{fI} I_t + W_{fO} O_{t-1} + b_f + P_f \cdot S_{t-1}) \quad \text{Forget probability}$$

$$u_t = \sigma(W_{uI} I_t + W_{uO} O_{t-1} + b_u + P_u \cdot S_{t-}) \quad \text{Update probability}$$

$$o_t = \sigma(W_{oI} I_t + W_{oO} O_{t-1} + b_o + P_o \cdot S_{t-1}) \quad \text{Output probability}$$

The non-recurrent units 62 and recurrent units 65 to 67 may alternatively be replaced by Gated Recurrent Units having a form as follows. In at least some cases, the Gated Recurrent Unit (GRU) has been found to be quicker to execute but may also yield poorer accuracy. The architecture of the GRU is not as intuitive as the LSTM, dispensing with the separation between the hidden state and the output and also combining the 'forget' and 'input gates'.

$$o_t = \sigma(W_{oI} I_t + W_{oS} S_{t-1} + b_o) \quad \text{Output probability}$$

$$u_t = S_{t-1} \cdot \sigma(W_{uI} I_t + W_{uS} S_{t-1} b_u) \quad \text{Update from state}$$

$$v_t = \tan h(W_{vI} I_t + W_{vR} u_t + b_v) \quad \text{Value to update with}$$

$$S_t = (1 - o_t) \cdot S_{t-1} + o_t \cdot v_t \quad \text{Update state}$$

While there are the same number of columns output as there are events, it is not correct to assume that each column is identified with a single event in the input to the network since its contents are potentially informed by the entire input set of events because of the presence of the bidirectional layers. Any correspondence between input events and output columns is through how they are labelled with symbols in the training set.

Returning to FIG. 3, the sets of weight values 51 output by the RNN 50 will now be discussed (a set of weight values is also referred to herein as a "weight distribution"). In the example of FIG. 3, a set of weight values is output for each of the feature vectors input to the RNN. Since a feature vector is generated by the CNN 40 for each window of the measurements in the input signal 10, in the method of FIG. 3 a set of weight values is produced for each window. As discussed above, a set of weight values may represent the likelihoods that there was a transition between a particular pair of labeled units in the polymer sequence during the respective window.

The time-step between successive windows of the input signal 10 may in principle be of the same length as the sample period of the signal, but is typically longer than the sample period of the signal 10 due to oversampling in the neural network 20. However, the time-steps of are a regular length, for example corresponding to the stride 13 of the windowing unit 30, which contrast to systems where event-calling is performed and so the time-steps between successive weight distributions 51 corresponds the length of successively detected events, which are variable.

In some embodiments, the weight distributions 51 may be output at a higher rate than the rate at which successive polymer units translocate with respect to the nanopore, i.e., there are more weight distributions 51 than polymer units. Notwithstanding the above, it may be noted that the plural number of weight distributions 51 which correspond to each polymer unit in the series may be a priori unknown.

Each weight distribution 51 comprises a plurality weights, wherein each of the weights is associated with two labels—a first label representing an initial unit of the polymer prior to a transition, and a second label representing a final unit of the polymer unit after the transition. The labels are each associated with a physical unit of the polymer, although there need not be a 1:1 correspondence between a label and a physical unit, as in some cases multiple labels may correspond to the same physical unit, as discussed further below.

In some embodiments, the weights represent posterior probabilities. For instance, the weights may be actual posterior probabilities, or may be weights which are not actual probabilities but nonetheless are representative of the posterior probabilities. Generally, where the weights are not actual probabilities, the posterior probabilities could in principle be determined therefrom, taking account of the normalization of the weights.

As noted above, the RNN 50 may output a set of weights where each weight corresponds to a transition between labels over a set of labels including labels representing the possible types of polymer unit. Thus, a weight associated with a given transition represents a posterior probability for that transition. As there are more weight distributions 51 than polymer units, it is to be understand that in some representations a transition from a label to the same label is allowed and so the weight distributions 51 may include a weight corresponding to such a transition. Put another way, the word "transition" as used herein does not imply that the label must change, nor does it imply that an additional polymer unit must be emitted.

Various illustrative types of weight distributions 51 that may be output by the RNN 50 are described below. Each of those example refers to the case where the polymer units are polynucleotides and the types of polymer units are the four bases A, C, G and T. As discussed above, the present methods are equally applicable to larger numbers of types of polynucleotide and/or to polymer units that are not nucleotides, so these examples may be generalized accordingly. In each of the examples, the weight distributions 51 include weights representing transitions between labels. Thus, the weights are notated as $w_{ij}$, where i is an index for the label from which the transition occurs and j is an index for the label to which the transition occurs. Thus weight $w_{ij}$ is weight for the transition from label i to label j. In each of the drawings, the rows correspond to the labels i from which the transitions occur and the columns correspond to the labels j to which the transition.

In the discussion of the various different types of weight distributions below, it will be appreciated that an RNN configured to produce a series of weight distributions of a given type may be configured specifically to produce that type of weight distribution. For instance, an RNN that produces a weight distribution in which multiple labels correspond to the same polynucleotide (e.g., as in the multi-stay example of FIG. 13) may be configured differently than an RNN that produces the 'basic' weight distribution of FIG. 10. One example of such a configuration is an RNN configured with a number of feed-forward elements in its output (final) layer that is equal to the number of weights in the weight distribution to be produced. FIGS. 7-9 also provide examples showing a number of outputs from units of an RNN; it will be appreciated that any one or more of these configurations may be present within the RNN such that the number of outputs is equal to the number of weights in the weight distribution to be produced.

FIGS. 10 and 11 show examples of two different weight distributions 51 that may be output by the RNN 50. In the example of FIG. 10, there is a single label for each of the four bases shown as A, C, G and T. All transitions between any pair of these four bases are allowed, so there are a total of sixteen weights $w_{ij}$ corresponding to the 16 transitions from any of the four labels to any of the four labels.

The example of FIG. 10 does not provide a good representation of homopolymers, which are a succession of plural polymer units of the same type within the series of polymer units. This is because a transition from a label to the same label does not distinguish between there being no transition in a given window of the input signal and there being a transition between the same two labels in the window. As a result, a series of transitions from a label to the same label represents a series of any number (one or more) of instances of a polymer unit (i.e., both a single polymer unit and a homopolymer of the same type of polymer unit of any length).

However, FIG. 11 is an example that improves the representation of homopolymers by expanding the representation of FIG. 10 so that the set of labels includes (i) a single label each representing a different one of the four bases, and (ii) a label representing a blank in the series of polymer units. All transitions between labels are allowed in the example of FIG. 11, so there are a total of 25 weights $w_{ij}$ corresponding to the 25 transitions from each of the labels to each of the labels. In this representation, a blank label represents a separation between two instances of a base (polymer units) in the series, even if they are of the same type. Put another way, in the sequence of polymer units it may be the case that a window of data measurements is analyzed but in that data window no transition between polymer units is present. In this case, the transition may be represented as a transition from the prior label to a 'blank' label, which represents that no new instance of a polymer unit was transitioned to in the window.

In some embodiments, blanks may be treated as compulsory, in that a blank must be present in the determined sequence of polymer units in order to treat polymer units on either side of the blank as being separate polymer units. For example, in the case of the following generated sequence of labels in which blanks are represented by a "-": A A A - - A, this would be resolved to an actual sequence of polymer units=A A. Each of the first three instances of the "A" label are treated as being instances of the same actual polymer unit "A," whereas the last "A" label is treated as distinct because it is separated from the first three "A"s by two blank labels.

In some embodiments, blanks may be treated as optional, in that a blank represents a spacer between polymer units and repetition of a label. For example, in the case of the following generated sequence of labels in which blanks are represented by a "-": A A A - - A, this would be resolved to an actual sequence of polymer units=A A A A. Each of the first three instances of the "A" label are treated as distinct polymer units, and the blank labels act as a spacer between these units and the final "A" label.

This representation in the output of the RNN 50 using weights corresponding to transitions between labels contrasts with approaches in which an RNN outputs posterior probabilities (a specific example of a weight) corresponding to one of four labels representing each of four types of polynucleotide (i.e., bases C, G, A and T) and a label representing a blank. That is, the approach described herein produces and analyzes weights that are each associated with a transition between labeled units, whereas other approaches may analyze weights that are each associated with a single labeled unit.

The approach described herein provides advantages over an approach in which a weight corresponds to a single label, because in the approach described herein additional information is conveyed by the weights that improves the accuracy of estimation of the series of polymer units. This is because the weights provide information on possible paths through the series of polymer units, whereas weights corresponding to the labels themselves lack this information because each weigh carries no information about event prior to, and later than the identified label. Thus, in the approach described herein additional information is provided to the step of estimating the polymer units, which improves the accuracy of the decoding.

In addition, the representation allows allowed and non-allowed transitions to be represented. That is, the labels may represent the possible types of polymer unit in a manner in which one or more of the transitions between labels is not allowed and other transitions are allowed. For instance, the weight distributions 51 may comprise weights corresponding to transitions that are allowed, and/or the weight distributions 51 may comprise null weights corresponding to transitions that are not allowed.

A null weight, which represents a non-allowed transition, may be represented in the weight distribution output by the RNN 50 as simply the absence of a weight. In the examples shown in the drawings, for example, the null weights are illustrated by replacing a weight with a dash ("-"). Alternatively, a null weight may be represented in the weight distribution as a weight having a nominal value. Such a nominal value may be a value having a zero value or an insignificant magnitude so that it does affect the estimation performed by the decoder 80 as described below. Alternatively, such a nominal value may be a value that is present in the weight distribution 51 output by the RNN but ignored by the decoder 80, for example by using a transition matrix as described below.

Some examples of weight distributions that model allowed and/or non-allowed transitions are as follows.

A first example where allowed and non-allowed transitions occur is where the set of possible types of polymer unit includes a type of polymer unit that always appears in a known sequence of polymer units. In this case transitions in accordance with the known sequence are allowed and transitions contrary to the known sequence are not allowed. An example of this for polynucleotides is that 5-methyl cytosine in vertebrates only occurs on cytosines that precede a guanine ("CpG"), and this can be used to further restrict the possible transitions and so fewer weights from the RNN 50 are needed that would otherwise be required if all transitions were allowed. That is, CpG methylation results in methylated C (which will be represented herein as $C^M$) always being followed by G, so $C^M$ always occurs in the known sequence $C^M G$.

FIG. 12 is an example of a weight distribution 51 used to represent $C^M$ in which certain transitions from $C^M$ to other bases are not allowed. In the example of FIG. 12 and subsequent illustrated examples of weight distributions, the initial state in the transition is shown as a row index (left) whereas the final state in the transition is shown as a column index (top). The weight distribution in FIG. 12 is adapted from that of FIG. 11 to add a label representing methylated C to the four labels representing the four types of polynucleotide (i.e., bases C, G, A and T) and a label representing a blank. In this case, transitions from $C^M$ to A, C or T are not allowed, so there are null weights for those transitions, i.e., weights $w_{61}$, $w_{62}$ and $w_{64}$ are null in the weight distribution. This allows the RNN to provide better information about the methylated C base, which improves the accuracy of estimation of the methylated C base.

Optionally, the weight of a transition from $C^M$ to $C^M$ can be null. This may be described as a "stay," which is a situation in which a transition occurs between the same two labels. In the case of $C^M$ to $C^M$, the weight may be null because although it can be identified during measurements said transition does not form part of a sequence because CpG methylation results in methylated C always being followed by G, i.e., the sequence $C^M G$. A further example of this is the flip-flop representation described below, wherein transitions from the modified-flip or modified-flop to guanine or modified-flop labels are allowed reducing the number of weights needed from the RNN 50 from 60 to 52 (compared with 100 weights needed for all possible transitions). Aside from the reduction in the amount of network outputs needed, restricting the transitions to those that are possible prevents the method from producing estimates of types of polymer unit with modifications in impossible contexts which would be both errors in the estimate and false positive modification calls.

A second example where allowed and non-allowed transitions occur is a representation in which each type of polymer is represented by multiple labels instead of a single label. For example, the set of labels may include a first and a second label both corresponding to the same polymer unit, where the first label represents the start of an instance of the type of polymer unit, and the second label represents a stay in the instance of the type of polymer unit. As mentioned above, a "stay" represents a situation in which the method determines that the label associated with successive weight distributions does not change, which may be considered as two weight distributions corresponding to the same instance of a polymer unit. Herein, this example will be referred to as "multi-stay". This improves the representation because a stay is represented by a different label. This improves the accuracy of estimation of the polymer unit.

The multi-stay representation has the consequence that some transitions are allowed and some are not. For example, in one implementation a first label e.g., "A" is only allowed to transition into a second label corresponding to the same type of polymer unit e.g., "$A^S$" or into a first label of a different type of polymer unit e.g. "C", "G" or "T". More specifically, the following transitions are allowed and not allowed:

a) transitions from each first label to the first label for any other type of polymer unit are allowed, and transitions from each first label to the first label for the same type of polymer unit are allowed;

b) transitions from each first label to the second label (the 'stay' label) for the same type of polymer unit are allowed;

c) transitions from each first label to the second label (the 'stay' label) for any other type of polymer unit are not allowed;

d) transitions from each second label (the 'stay' label) to the first label for the same type of polymer unit or the first label for any other type of polymer unit are allowed;

e) transitions from each second label (the 'stay' label) to the second label (the 'stay' label) for the same type of polymer unit are allowed; and f) transitions from each second label (the 'stay' label) to the second label (the 'stay' label) for any other type of polymer unit are not allowed.

The above illustrative multi-stay representation scheme may be considered to be a "compulsory" scheme in a similar manner to the scheme of FIG. 11 in which blanks may be considered compulsory or optional as described above. As such, it will be appreciated that a similar scheme to the above may be envisioned for the multi-stay representation in which a first label is allowed to transition into the same first label. Such a scheme may be considered an "optional" multi-stay representation scheme.

FIG. 13 illustrates an example of a weight distribution 51 which is adapted from that of FIG. 10 to implement the above-described 'multi-stay' type of representation. Thus, in FIG. 13, the set of labels includes four first labels for the four types of base shown as A, C, G and T, and four second labels for the four types of base shown as $A^S$, $C^S$, $G^S$ and $T^S$. Herein, the superscript S (for "stay") is used to distinguish the second labels from the first labels corresponding to the same type of base, and represents a stay. As shown in FIG. 13, in view of the transitions that are allowed and not allowed, the following weights are present or null:

a) transitions from each first label (e.g., A) to the first label for any other type of polymer unit (e.g., C, G and T) are allowed, and transitions from each first label (e.g., A) to the first label for the same type of polymer unit (e.g., A) are allowed, so all the weights in the top left quadrant are present;

b) transitions from each first label (e.g., A) to the second label for the same type of polymer unit label (e.g., $A^S$) are allowed, so weights in the top right quadrant $w_{15}$, $w_{26}$, $w_{37}$ and $w_{48}$ are present;

c) transitions from each first label (e.g., A) to the second label for any other type of polymer unit (e.g., $C^S$, $G^S$ and $T^S$) are not allowed, so weights in the top right quadrant other than $w_{15}$, $w_{26}$, $w_{37}$ and $w_{48}$ are null;

d) transitions from each second label (e.g., $A^S$) to the first label for the same type of polymer unit (e.g., A) or the first label for any other type of polymer unit (e.g., C, G and T) are allowed, so all weights in the bottom left quadrant are present;

e) transitions from each second label (e.g., $A^S$) to the second label for the same type of polymer unit (e.g., $A^S$) are allowed, so weights in the bottom right quadrant $w_{55}$, $w_{66}$, $w_{77}$ and $w_{88}$ are present; and f) transitions from each second label (e.g., $A^S$) to the second label for any other type of polymer unit (e.g., $C^S$, $G^S$ and $T^S$) are not allowed, so weights in the bottom right quadrant other than $w_{55}$, $w_{66}$, $w_{77}$ and $w_{88}$ are null.

The multi-stay representation can be combined with the representation for methylated C set out above, or indeed with any similar representations for a type of polymer unit that always appears in a known sequence of polymer units.

Representations of homopolymers will now be considered. A homopolymer is a sequence of consecutive instances of polymer units of the same type in the series of polymer units. Homopolymers are properly represented by the multi-stay representation discussed above because a transition from the second label (e.g., $A^S$) to the first label for the same type of polymer unit (e.g., A) represents a second instance of the same type of polymer unit. For example, a series of labels $AA^SA^SAA^SAA^SA^SAA^SA^SA^SA^S$ (SEQ ID NO: 1) represents a homopolymer of length four polymer units: $AA^SA^S$, $AA^S$, $AA^SA^S$, and $AA^SA^SA^SA^S$, the number of consecutive labels A or $A^S$ being arbitrary and varying in practice. However, accuracy of estimation may be improved by adapting the representation so that the labels represent homopolymers in an encoded form, for example as follows.

A first representation of homopolymers in encoded form will be referred to as a "flip-flop" representation and is as follows.

One of the benefits of having the output of an analysis method being overlapping fixed length fragments is that amount of overlap can be used to determine if, and how many, translocations of polymer units have taken place. Methods of analysis relying on overlaps fail in low complexity regions of a polymer, like homopolymers, where the overlap may be ambiguous (e.g., AAA→AAA may be zero, one, two or more translocations of the A homopolymer) and a different representation is desirable. In a flip-flop representation, the labels represent homopolymers by including plural labels for each type of polymer unit, wherein the plural labels for each type of polymer unit represent consecutive instances of the type of polymer unit in the series of polymer units. Typically, there are two labels for each type of polymer unit, which may be called "flip" and "flop" for ease of reference.

Thus, rather than decoding to fixed length fragments, the flip-flop method of decoding represents a sequence of polymer units as a sequence of "flip" and "flop" labels with the following restriction: homopolymers must start in the "flip" label and then alternate between "flip" and "flop" labels until they terminate. The flip-flop representation ensures that no label is ever the same as its neighboring labels and so a translocation of one unit with a homopolymer (a change from flip to flop, or vice versa) is always distinguishable from no translocation (a flip to flip, or flop to flop). By way of example, the series of polymer units CAATACCTT-TAAAAAAAAGAAACTTTTAGCTC (SEQ ID NO: 2) is represented as $CAA^FTACC^FTT^FTAA^FAA^FAA^FAA^F$-$GAA^FACTT^FTT^FAGCTC$ (SEQ ID NO: 2) where the flip label for polymer unit X is represented by X and the corresponding flop label is represented by $X^F$.

Under the flip-flop encoding, a translocation of one is always distinguishable from no translocation, although in at least some cases translocations of a greater number of polymer units may still be ambiguous. Thus, in terms of the labels represented by the successive weight distributions 51, if the two labels for the base A are A (being flip) and $A^F$ (being flop), then a series of labels $AAAAAAA^FA^FA^FA$-$^FAAA$ (SEQ ID NO: 1) represents a homopolymer of length three polymer units, the number of consecutive labels A or $A^F$ being arbitrary and varying in practice. There may in principle be more than two labels for each type of polymer unit, but two labels are sufficient.

The plural labels for each type of polymer unit may have a predetermined cyclical order. In an example of two labels for each type of polymer unit, flip and flop, the predetermined cyclical order may be that the first polymer unit is always flip and thereafter flip and flop alternate. Thus, some transitions between labels are allowed by the predetermined cyclical order and other transitions between are not allowed by the predetermined cyclical order. There are null weights for transitions that are not allowed by the predetermined cyclical order in the weight distributions, whereas of course there are weights for transitions that are allowed by the predetermined cyclical order.

In the above example that the predetermined cyclical order is that the first polymer unit is always flip and thereafter flip and flop alternate, transitions from a flip of any given type of polymer unit to the flop of any other type of polymer are not permitted, and similarly transitions from a flop of any given type of polymer unit to the flop of any other type of polymer are not permitted.

FIG. 14 illustrates an example of a weight distribution 51 for this type of flip-flop representation. Thus, in FIG. 14, the set of labels includes four first labels (flip) corresponding to the four types of base shown as A, C, G and T, and four second labels (flop) corresponding to the four types of base shown as $A^F$, $C^F$, $G^F$ and $T^F$. As shown in FIG. 14, in view of the transitions that are allowed and not allowed, the following weights are present or null:

a) transitions from each first label (flip, e.g., A) to the first label (flip) for all types of polymer unit (e.g., A, C, G and T) are allowed, so all weights in the top left quadrant are present;

b) transitions from each first label (flip, e.g., A) to the second label for the same type of polymer unit (flop, e.g., $A^F$) are allowed, so weights in the top right quadrant $w_{15}$, $w_{26}$, $w_{37}$ and $w_{48}$ are present;

c) transitions from each first label (flip, e.g., A) to the second label for any other type of polymer unit (e.g., $C^F$, $G^F$ and $T^F$) are not allowed, so weights in the top right quadrant other than $w_{15}$, $w_{26}$, $w_{37}$ and $w_{48}$ are null;

d) transitions from each second label (flop, e.g., $A^F$) to the first label for all types of polymer unit (flip, e.g., A, C, G and T) are allowed, so all weights in the bottom left quadrant are present;

e) transitions from each second label (flop, e.g., $A^F$) to the second label for the same type of polymer unit (flop, e.g., $A^F$) are allowed, so weights in the bottom right quadrant $w_{55}$, $w_{66}$, $w_{77}$ and $w_{88}$ are present; and f) transitions from each second label (flop e.g., $A^F$) to the second label for any other type of polymer unit (flop, e.g., $C^F$, $G^F$ and $T^F$) are not allowed, so weights in the bottom right quadrant other than $w_{55}$, $w_{66}$, $w_{77}$ and $w_{88}$ are null.

Depending on the rate at which measurements are taken relative to the speed of translocation of the polymer unit, apparent translocation of more than one unit may be observed when the polymer translocates multiple times between measurements. Where this is a probable occurrence, additional redundant labels of each polymer unit ("flap", "flup", "flep", etc.) can be added so that the presence of additional units can be represented, For example, a sequence going from flip to flap implies the presence of an intermediate flop label.

A second representation of homopolymers in encoded form will be referred to as a run-length encoded representation and is as follows.

Figure 15:
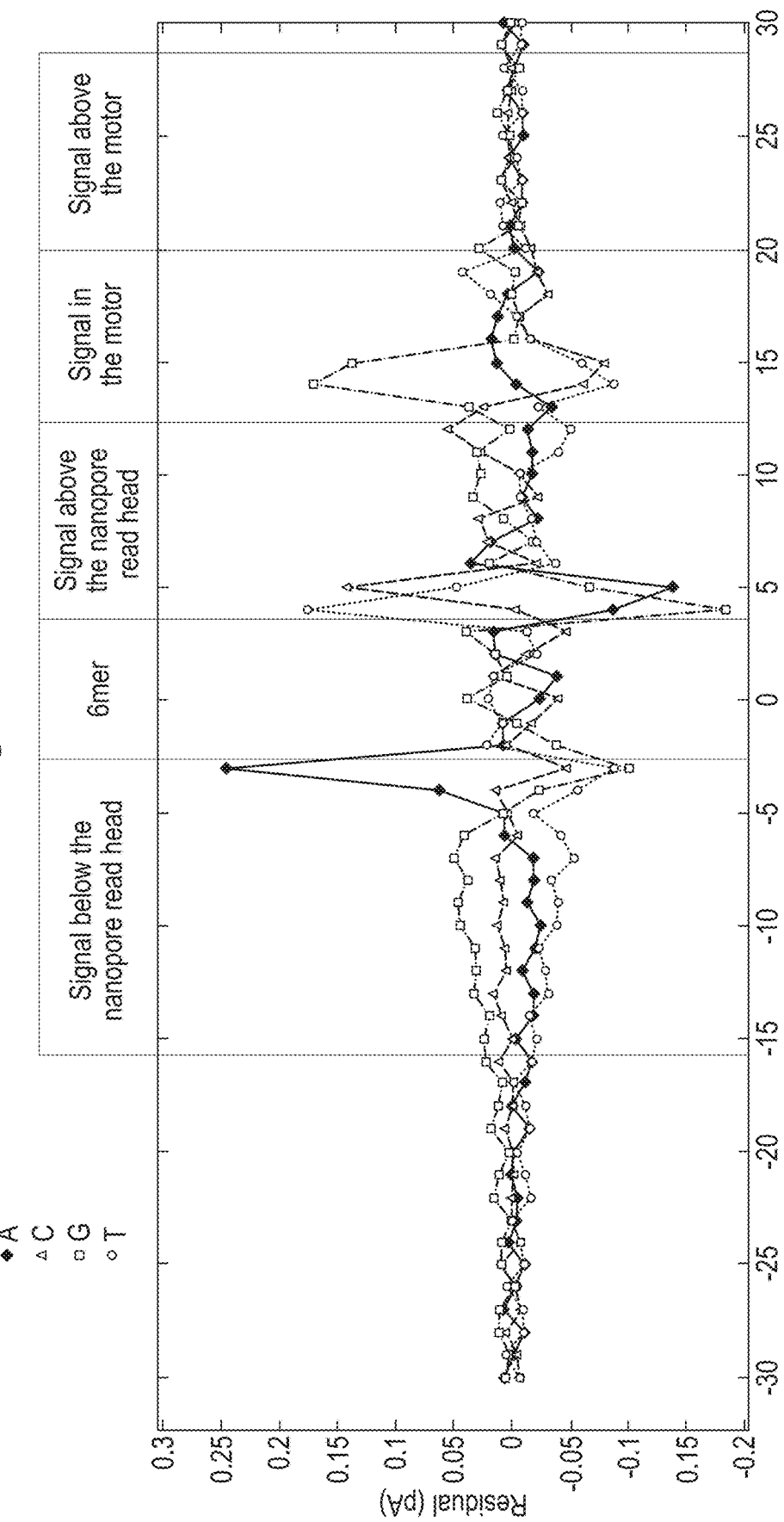
FIG. 15 is a plot of residual currents for four bases using a 6-mer model of signal and approximate location of relative to read head and other components of the system.

The flip-flop representation can call through long homopolymers but must do so as a path of alternating labels and make multiple connected calls. For longer homopolymers, the flattening of the observed signal may mean there is no longer a clear time when the signal changes due to the polymer translocating with respect to the nanopore and the position of each change in label becomes more arbitrary. FIG. 15 shows an example of this loss of specificity for an example region where the weights are split between T-flip or T-flop despite the cumulative evidence for both being high.

Thus, rather than represent a homopolymer as a sequence of alternating labels, instead the entire homopolymer can be represented by a label corresponding to the type of polymer unit. Thus, rather than training the RNN 50 to call the canonical sequence or its flip-flop encoding, the RNN 50 is trained to call the run-length encoding of the series of polymer units. For example, the run-length encoding of the canonical sequence TAATTCAAACTTTTTTCTGA-TAAGCTGGT (SEQ ID NO: 3) is $TA^2T^2CA^3CT^7CTGATA^2GCTG^2T$ (SEQ ID NO: 3) where the run-length follows the base and lengths of one are implicit. The longest possible run is always taken so no run is adjacent to a run with the same base.

In a first formulation of run-length encoded representation, the labels include labels for different run-lengths of each type of polymer unit. FIG. 16A illustrates an example of such a weight distribution. In this example, there is a single label for each of the four bases shown as A, C, G and T and for each of the homopolymers of each base shown as $A^2$, $A^3$, etc. This is unwieldy as there are a large number of labels to accommodate all possible lengths of homopolymer and all transitions are allowed, except for a transition from label corresponding to a homopolymer of one type of base to a homopolymer of the same type of base but of a different length, so there are a large number of weights $w_{ij}$ corresponding to most transitions between labels almost equal in number to the square of the number of labels (other possible transition schemes could alternatively be implemented).

Long homopolymers in large genomes occur more frequently than would be expected by chance, and so the number of labels needed to represent all homopolymer lengths that might be encountered during routine sequencing is extremely high. Since the weights output by the network are explicitly parameterizing the transitions between homopolymer labels, training data becomes an issue both because of the large number of parameters that need to be trained and because they are weakly coupled. Shuffling the labels of the labels (e.g., $A^6 \rightarrow A^3$, $T^2 \rightarrow T^7$, $G^8 \rightarrow G^1$) results in an equivalent model that can be trained to identical performance, so training examples of homopolymers of length 4 and 6 don't inform the model about those of length 5.

An alternative and preferred formulation of a run-length encoding is to factor the weight distributions 51 into several dependent distributions. Thus, the labels include a label for each type of polymer unit, and the weight distributions 51 comprise further weights over possible lengths of the run-length compressed homopolymer for each type of polymer unit, in addition to the weights corresponding to transitions. Transition weights are emitted by the RNN 50 to describe a distribution over run-length compressed sequences, that is the run-length encoded sequence with all the lengths dropped, and a separate set of conditional distributions for the length of a run given the polymer unit.

In this preferred formulation of a run-length encoding, the weight distribution 51 output by the RNN may include weights in the form shown in FIG. 10 to represent transitions between different types of polymer unit. As discussed above, in this case a series of transitions from a label to the same label represents a series of any number of instances of a polymer unit (i.e., a single polymer unit or a homopolymer of the same type of polymer unit of any length).

As an alternative to that, this preferred formulation of a run-length encoding, the weight distribution 51 output by the RNN may be defined over a set of labels where each type of polymer is represented by first and second labels instead of a single label, for example labels A and $A^H$ corresponding to a first type of polymer unit. This is similar to the multi-stay representation shown in FIG. 13, except that the allowed transitions differ so that a series of labels for a polymer unit of a given type always starts with a single instance of the first label and then one or more instances of the second label. This is achieved as follows:

a) transitions from each first label to the first label for any other type of polymer unit are allowed, but transitions from each first label to the first label for the same type of polymer unit are not allowed;

b) transitions from each first label to the second label for the same type of polymer unit are allowed, c) transitions from each first label to the second label for any other type of polymer unit are not allowed;
d) transitions from each second label to the first label for the same type of polymer unit are not allowed;
e) transitions from each second label to the first label for any other type of polymer unit are allowed;
f) transitions from each second label to the second label for the same type of polymer unit are allowed; and
g) transitions from each second label to the second label for any other type of polymer unit are not allowed.

FIG. 16B illustrates an example of such a weight distribution 51 which is adapted from that of FIG. 10 to implement this type of representation. Thus, in FIG. 16B, the set of labels includes four first labels corresponding to the four types of base shown as A, C, G and T, and four second labels corresponding to the four types of base shown as $A^H, C^H, G^H$ and $T^H$. As shown in FIG. 16B, in view of the transitions that are allowed and not allowed, the following weights are present or null:

a) transitions from each first label (e.g., A) to the first label for any other type of polymer unit (e.g., C, G and T) are allowed, but transitions from each first label (e.g., A) to the first label for the same type of polymer unit (e.g., A) are not allowed, so weights in the two left quadrant are present other than $w_{11}, w_{22}, w_{33}$ and $w_{44}$ which are null;
b) transitions from each first label (e.g., A) to the second label (e.g., $A^H$) for the same type of polymer unit are allowed, so weights in the top right quadrant $w_{15}, w_{26}, w_{37}$ and $w_{48}$ are present;
c) transitions from each first label (e.g., A) to the second label for any other type of polymer unit (e.g., $C^H, G^H, T^H$) are not allowed, so weights in the top right quadrant other than $w_{15}, w_{26}, w_{37}$ and $w_{48}$ are null;
d) transitions from each second label (e.g., $A^H$) to the first label (e.g., A) for the same type of polymer unit are not allowed, so weights in the bottom left quadrant $w_{51}, w_{62}, w_{73}$ and $w_{84}$ are null;
e) transitions from each second label (e.g., $A^H$) to the first label for any other type of polymer unit (e.g., C, G and T) are allowed, so weights in the bottom left quadrant other than $w_{51}, w_{62}, w_{73}$ and $w_{84}$ are present;
f) transitions from each second label (e.g., $A^H$) to the second label for the same type of polymer unit (e.g., $A^H$) are allowed, so weights in the bottom right quadrant $w_{55}, w_{66}, w_{77}$ and $w_{88}$ are present; and
g) transitions from each second label (e.g., $A^H$) to the second label for any other type of polymer unit (e.g., $C^H, G^H, T^H$) are not allowed, so weights in the bottom right quadrant other than $w_{55}, w_{66}, w_{77}$ and $w_{88}$ are null.

Thus, a series of labels for a polymer unit of a given type always starts with a single instance of the first label and then one or more instances of the second label. For example, any of the series of labels A, $AA^H$, $AA^HA^H$, etc. (with any arbitrary number of labels $A^H$) represents a series of any number of instances of a polymer unit (i.e., a single polymer unit or a homopolymer of the same type of polymer unit of any length).

As mentioned above, the example of FIG. 10 does not provide a good representation of homopolymers, and the same is true of the example of FIG. 16A. However, homopolymers are represented by the further weights over possible lengths of the run-length compressed homopolymer. There will now be described several possibilities for such further weights, each of which may be applied in combination with the weights in the form of FIG. 10 or in the form of FIG. 16A.

A first possibility for the further weights is that they comprise a categorical distribution of weights over a set of possible lengths of the homopolymer for each possible type of polymer unit. The possible lengths are a category and the RNN 50 outputs assigns a weight to each category. In general, each category could represent a single homopolymer length, or some or all of the categories could represent a range of homopolymer lengths. Categories could include one representing all homopolymers greater than a given length. Categories need not be uniformly spaced.

FIG. 17 shows an example of such further weights in accordance with this first possibility. In this example, there is a weight $I_{ij}$ for each possible length of each of the four bases A, C, G, T, the bases being indexed by the index i, and the lengths being indexed by the index j. In this example each category corresponds to a single length, but alternatively each category could correspond to a range of lengths to reduce the number of categories. The further weights shown in FIG. 17 form part of the weight distribution 51 together with the weights for transitions between labels, which may take the form as described above, for example as shown in any of FIGS. 10 to 13.

A categorical distribution requires fewer parameters than fully specifying the transitions between all homopolymer labels and allows the underlying run-length compressed genome to be estimated, but still has the problem of weak coupling that make poor use of training data and makes long homopolymers difficult to train.

A second possibility for the further weights is that they comprise parameters of a parameterized distribution over possible lengths of the homopolymer for each possible type of polymer unit. Such parameters can be used to calculate the probability that a homopolymer of a given polymer unit was any given length.

FIG. 18 shows an example of such further weights in accordance with this second possibility. In this example, there are weights $p_{ij}$ for each of four types of bases shown as A, C, G, T and indexed by the index i. The weights indicate j parameters $P_1, P_2, \ldots P_j$ of the distribution which parameters are indexed by the index j. The parameters may be any parameters that represent a distribution. In general, j may have any plural value, depending on the distribution. The further weights shown in FIG. 18 form part of the weight distribution 51 together with the weights for transitions between labels, which may take the form as described above, for example as shown in any of FIGS. 10 to 13.

By way of example, FIG. 18 gives an example of two parameters, mean and variance, used to represent different weight distributions for the homopolymer length.

Figure 19:
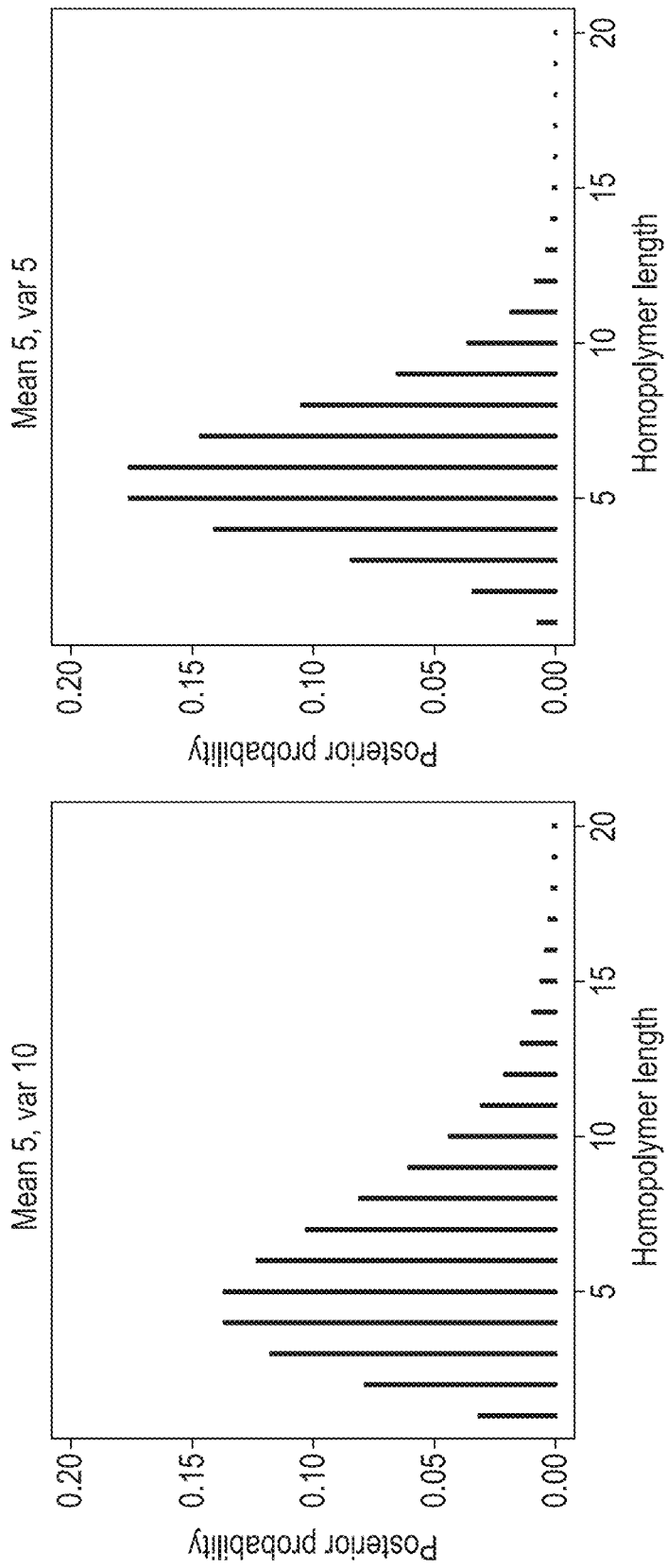
FIG. 19 is a plot of two distributions represented by different values of mean and variance parameters.

An advantage of using a parameterized distribution over homopolymer length is that the distribution can interpreted as a posterior distribution for the homopolymer length, allowing a confidence to be placed in the estimated length. For example in FIG. 19, both the distributions give the same posterior mean estimate of the homopolymer length but give a different confidence in it, the distribution with the higher variance (left) being less confident than that with the lower variance (right).

Since the predictions for different homopolymer lengths are all via the same set of network outputs, they are much more tightly coupled than before and allow the network to generalize from examples of one homopolymer to those of similar lengths.

Many different probability distributions could be used in conjunction with the output of the network. It is advantageous to select a distribution that is able to represent any homopolymer length that is likely to occur and so the distribution should have support over a large or even semi-infinite set of potential lengths. It is also desirable that there exist values of the parameters that represent both high confidence (low variance) and low confidence (high variance) in a given homopolymer length. Negative binomial or geometric distributions may be used, and cannot distinguish between the high and low confidence cases.

The variance of a geometric distribution is a function of the mean, the negative binomial has an additional degree of freedom, and its variance must always be greater than the mean. Distributions satisfying both these criteria can found by discretizing a continuous distribution that has support over $[0,\infty]$. One way of discretizing would be set the probability of a homopolymer being of length L to the integral of the density function from L to L+1, alternatively L-0.5 to L+0.5 with appropriate treatment of L=0.

Preferably, the distribution that is discretized has an explicit cumulative density function. Examples of such densities are, but not limited to, Weibull distribution, Log-Logistic distribution, Log-Normal distribution, Gamma distribution. It is advantageous, but not necessary, if there are explicit expressions for the mean, mode and variance of the parametric distribution used or its discretized counterpart.

FIG. 20A illustrates some suitable discrete distributions for representing homopolymer lengths, all having support on $\mathbb{N}$. $\Gamma(\alpha)$ is the Gamma function, $\gamma(\alpha, \beta)$ is the incomplete gamma function, and $\Phi(x)$ is the cumulative distribution of the standard normal distribution.

In each of the first and second possibilities, the further weights are defined for each possible type of polymer unit, i.e., the possible type of polymer unit of the homopolymer. While this is effective, further improvement may be provided by a modification in which the further weights (a) for possible pairs of the type of the given polymer unit and the type of the preceding polymer unit, (b) for possible pairs of the type of the given polymer unit and the type of the following polymer unit, or (c) for possible triplets of the type of the given polymer unit, the type of the preceding polymer unit, and the type of the following polymer unit.

With this modification, the weights take the same form, for example a categorical distribution of weights over a set of possible lengths of the homopolymer in accordance with the first possibility or parameters of a parameterized distribution over possible lengths of the homopolymer in accordance with the second possibility, but the number of weights is increased. For cases (a) and (b), the number of weights is increased by three times, so as to define distributions for each possible pair instead of each possible type of polymer unit, for example for 12 pairs of bases {(A,C), (A,G), (A,T), (C,A), (C,T), (C,G), (G,A), (G,C), (G,T), (T,A), (T,C), (T,G)} instead of for 4 types of base {A, C, G, T}. By way of example, FIG. 20B shows an example of such further weights that comprise parameters of a parameterized distribution over possible lengths of the homopolymer defined for each pair of types of polymer unit. This corresponds to cases (a) and (b), the pairs being in case (a) the given polymer unit and the type of the preceding polymer unit, and in case (b) being the type of the given polymer unit and the type of the following polymer unit. The form of the parameters themselves is the same as for FIG. 18 and can be used in the same way to calculate the probability that a homopolymer of a given polymer unit was any given length.

Similarly, for case (c), the number of weights is increased by nine times, so as to define distributions for each possible triplet, for example for 36 triplets of bases instead of for 4 types of base. By way of example, FIG. 20C shows an example of such further weights that comprise parameters of a parameterized distribution over possible lengths of the homopolymer defined for each triplet of types of polymer unit. This corresponds to case (c), the triplet being the given polymer unit, the type of the preceding polymer unit, and the type of the following polymer unit. The form of the parameters themselves is the same as for FIG. 18 and can be used in the same way to calculate the probability that a homopolymer of a given polymer unit was any given length.

This modification improves the accuracy based on an appreciation that the ability to discriminate of the edges of long homopolymers may vary in dependence on the preceding and/or following polymer units. For example, a transition from a base T to a homopolymer of base A is much easier to discriminate than a transition from a base C to a homopolymer of base A. Thus, the provision of different further weights representing the distributions for the various pairs or triplets provides a representation that may estimate the polymer units more accurately.

Similar factoring of the weight distributions 51 into several dependent distributions may be used to represent other properties of the polymer. One example is the representation of a type of polymer unit that has unmodified and modified forms, for example a polynucleotide that may include a type of base and a modified type of the same base.

Natural strands of DNA contain modified bases, for example 5-methyl cytosine or 6-methyl adenine, and their presence and location are detectable using a series of nanopore measurements. The flip-flop and other representations readily generalize to being able to call modifications by extending the set of labels from the bases A, C, G and T to include an additional label to represent the modified bases, for example $C^M$ to represent a modified C.

FIG. 21 shows an example of the weight distribution where the set of labels is expanded to additionally include a label $C^M$ corresponding to a modified base. Similarly, an additional label $C^M$ may be added to the set of labels in any of the weight distributions 51 shown in FIG. 10, 12 to 14, or 16A-16B.

This expansion of the alphabet of labels can also be used with previous methods described in the art, which assume that the signal at particular time can be represented by a fixed length fragment of bases, but these scale poorly as the number of modifications considered increases as the network must have an output for each possible transition between bases of the fixed length. For example, there are 1024 possible combinations ($4^5$) for fragments of length 5 consisting of the four canonical bases, 3125 ($=5^5$) if an additional modified base is allowed, and 7776 ($=6^5$) if two modifications are allowed. There are over a hundred modifications know in RNA and so fragment based models require amounts of processing that quickly increase.

The unmodified form of a polymer unit may be described as a canonical polymer unit and the modified form of a polymer unit may be described as a non-canonical polymer unit. A modified (or non-canonical) polymer unit typically affects a signal differently from a corresponding unmodified (canonical) polymer unit.

International Patent Appl. No. PCT/GB2019/052456, filed 4 Sep. 2019, to which reference is made and which is incorporated herein by reference, contains teachings relating to canonical and non-canonical bases which may be applied to any of the present methods disclosed herein. International Patent Appl. No. PCT/GB2019/052456 discloses examples of non-canonical bases that may be applied in any of the present methods. International Patent Appl. No. PCT/GB2019/052456 also discloses methods of preparing and analyzing a polymer comprising one or more non-canonical polymer unit that may be used in combination with any of the present methods.

By way of non-limitative example, one method disclosed in International Patent Appl. No. PCT/GB2019/052456 which may be combined with any of the present present methods is to convert a proportion of canonical polymer units (e.g., amino acids) to a corresponding non-canonical polymer unit (e.g., amino acid) in a non-deterministic manner, e.g., by chemical conversion or by enzymatic conversion. In that case, when deriving an estimate of the series of polymer units ("calling"), the non-canonical bases may be estimated ("called) as being the corresponding canonical base. This includes the methods described with reference to FIGS. 18b-18k of International Patent Appl. No. PCT/GB2019/052456.

Because of the non-deterministic incorporation of canonical and non-canonical polymer units into the target polymer, the underlying sequence of polymer units is not known and will vary on a strand-to-strand basis. Even though each strand contains alternative polymer units, there is still an associated canonical sequence, and it is of interest to call this directly rather than attempting to infer the type and location of any alternatives. In other words, despite there being additional polymer units in the target polymer, the analysis only attributes canonical values to the signal such that the determined sequence consists of bases from the group of A, C, G and T. In this manner, by recognizing a non-canonical polymer unit as a canonical polymer unit in the analysis, the initial conversion can provide a way to provide a signal with more information, for example having a consequence that any errors present in the analysis of the signal will be non-systematic, thereby leading to an improvement in the accuracy of the estimation.

Flip-flop, and similar representations, are much more tractable since the number of weights output from the RNN 50 required at each time point to parameterize the transition weight scales quadratically with the number of modifications rather than as a power equal to the fragment length (40 outputs for 4 canonical bases, 60 for one additional modified base, 84 for two, etc.).

According to some embodiments, in terms of the steps shown in FIG. 3, when the RNN 50 uses a flip-flop representation, training of the RNN may be performed to maximize the probability of the correct sequence, for each reads it produces a conditional random field that must be further decoded to produce an estimated sequence. The method of decoding used can introduce unwanted biases in the final call that reveal themselves in bulk metrics, like the total number of bases called read or summary statistics of its composition. Further biases may be apparent when estimated sequences from reads of strands with the same sequence, or containing a common subsequence, are considered in aggregate.

To reduce this issue, penalty terms may be incorporated into the trained RNN 50, adjusting its output to improve performance on metrics of interest: for example, subtracting a constant from all weights corresponding to not emitting a new polymer unit (flip-flip in the same base, or a flop-flop transition) will increase the number of polymer units called, whereas the proportion of a particular polymer unit can be increased by adding a constant to all transitions that end in emitting a new polymer unit of that identity.

The value of the penalty terms used can be tuned by calculating the metrics of interest for a representative set of reads over a grid of values, alternatively more formal optimization methods like the simplex method, or the many others known to the art, could be used. Rather than a fixed constant, the penalty term could be a function of prior information about the read.

Penalty terms can be incorporating into the RNN 50 at any layer, but it is preferable to incorporate them into the final layer where possible, directly affecting the transition weights emitted, as this has advantage that the effect on the final estimated sequence can be intuited and so guide the form the penalty.

To retain the interpretation of the output of the RNN 50 as a probabilistic model, it is desirable, but not essential, that penalties are incorporated before "global normalization" is performed.

Often, accurately determining the sequence of canonical bases and the presence of any modification are both of interest and it is undesirable for an attempt to estimate a modification to adversely affect the estimate of the underlying canonical sequence. One example of how this may occur is the splitting of weight between canonical cytosine and 5-methyl cytosine, so another base becomes the most likely estimation.

To prevent weight splitting behavior, the weight distributions 51 output by the RNN can be factored into two dependent distributions. In this case, the first distribution is a weight distribution 51 taking any of the forms described above a single label representing the type of polymer unit that has unmodified and modified forms, and the second distribution is a conditional distribution comprising further weights for the unmodified and modified forms. This representation may be expanded for any number of modified forms and for modified forms of any of the possible types of polymer unit.

FIG. 22 shows an example of the further weights for representing an unmodified form of the base C and a modified form of the same base $C^M$. In this case, the further weights are a weight ml corresponding to the unmodified form of the base C and a weight $m_2$ for the modified form of the base $C^M$. This may be applied instead of the weight distribution 51 of the type shown in FIG. 21. The further weights form part of the weight distribution 51 together with the weights for transitions between labels, which may take the form as described above, for example as shown in any of FIG. 10 to 14, or 16A-16B.

This factored representation means that the canonical sequence can be determined as if modifications were not present and then the location of any modification can be determined afterwards. The conditional distributions for modification may themselves be factored perhaps reflecting prior biological expectation. For example, one distribution might represent whether or not a cytosine is modified and other might represent that, given modification is present, whether that modification was 5-methyl cytosine or 5-hydroxymethyl cytosine.

Figure 23:
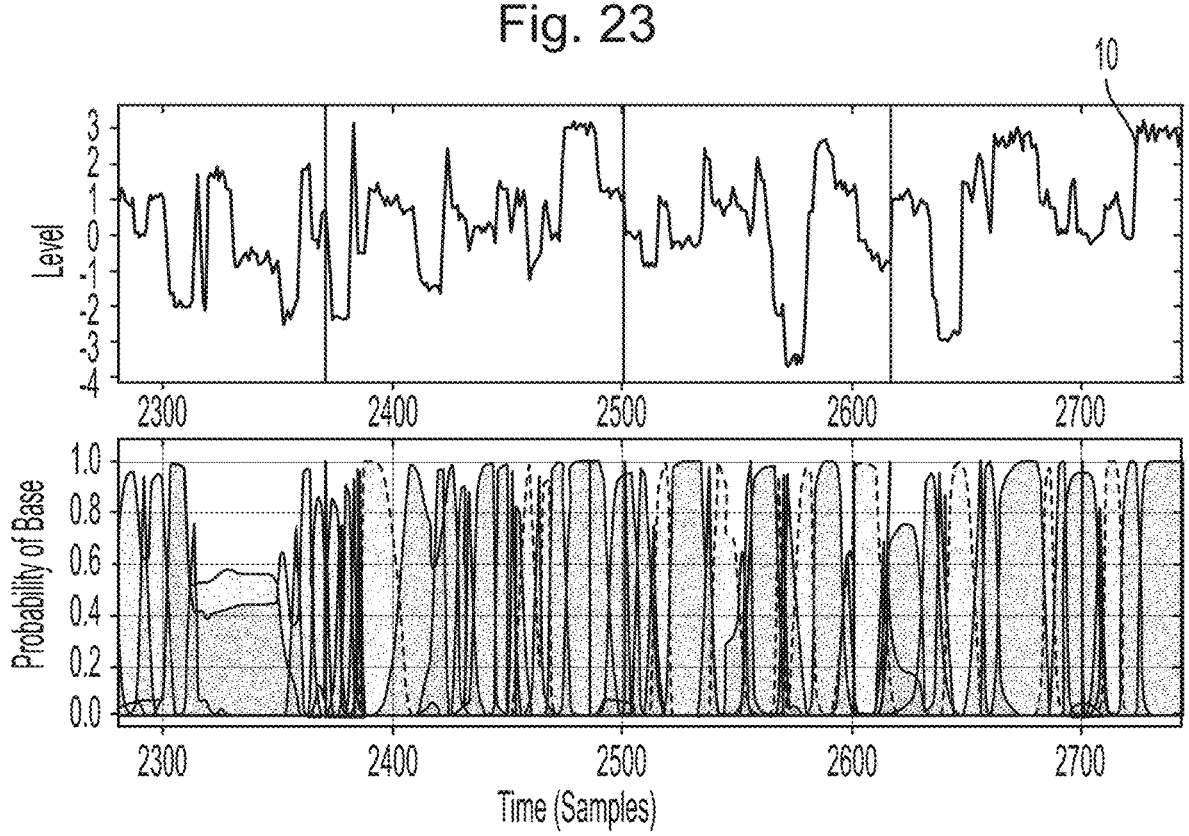
FIG. 23 is a plot of a signal and polymer units estimated therefrom for a 5-base representation.

As an example, FIG. 23 shows bases predicted by the output of the RNN 50 when employing a flip-flop representation of four bases that has been extended in this manner to detect a modified base 5mC. In this example, the modified base 5mC is estimated at three positions, at locations in agreement with external predictions.

As mentioned above, the weight distributions of the RNN 50 are normalized globally. Such a global normalization may be over all paths of labels through the series of weight distributions so that the sum over all possible paths is one. The global normalization may be over the output space such that the weights can be considered as posterior probabilities.

Global normalization is strictly more expressive than local normalization and avoids an issue known as the 'label bias problem'. The advantages of using global normalization over local normalization are analogous to those that Conditional Random Fields (Lafferty et al., Conditional Random Fields: Probabilistic Models for Segmenting and Labelling Sequence Data, Proceedings of the International Conference on Machine Learning, June 2001) have over Maximum Entropy Markov Models (McCallum et al., Maximum Entropy Markov Models for Information Extraction and Segmentation, Proceedings of ICML 2000, 591-598. Stanford, California, 2000). The label bias problem affects models in which the matrix of allowed transitions between labels is sparse, such as extensions to polymer sequences.

Global normalization alleviates this problem by normalizing over the entire sequence, allowing transitions at different times to be traded against each other. Global normalization is particularly advantageous for avoiding biased estimates of homopolymers and other low complexity sequences, as these sequences may have different numbers of allowed transitions compared to other sequences (it may be more or fewer, depending on the model).

The decoder 80 will now be considered. As noted with respect to FIG. 3, the weight distributions generated by the RNN 50 may be analyzed by the decoder 80 to determine a most likely sequence of labels corresponding to the plurality of weight distributions. The decoder 80 (which may be part of the analysis system 3, for instance) performs a method as shown in FIG. 24, as follows.

Figure 24:
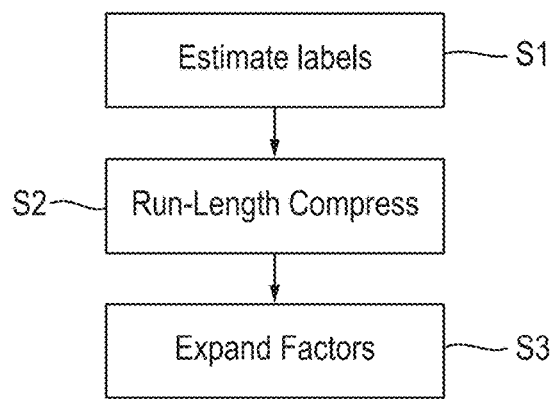
FIG. 24 is a flow diagram of a method performed by a decoder of the neural network.

In step S1 of FIG. 24, an estimate of a sequence of labels is derived based on the plurality of weight distributions 51. This estimation is discussed further below.

In step S2 of FIG. 24, the labels derived in step S1 are run-length compressed (which may also be termed 'decoding') to derive an estimate of the series of polymer units. This step may be needed where there are more weight distributions 51 than polymer units, for example in the schemes illustrated in FIGS. 11, 12, 13, 14, 16A-16B, 17 and 18 and described above. Run-length compression produces the estimates of the polymer units because consecutive sequences of the same label represent the same polymer unit in the representation of the polymer inherent in the RNN 50, as described above.

Step S2 may also account for representations where plural labels are used to represent a given type of polymer unit. For example in the multi-stay representation described above, the second labels may be compressed into the first label, since both correspond to the same type of polymer unit. Similarly, in the flip-flop representation described above, consecutive instances of the first label (flip) are compressed into a single polymer unit, and consecutive instances of the first label (flop) are compressed into another single polymer unit, and so on, thereby providing an estimate of a homopolymer. Step S2 may thereby comprise determining a sequence of polymer units corresponding to a sequence of labeled units by considering which polymer units correspond to each of the labeled units in the sequence of labeled units.

For example, in the scheme of FIG. 11, decoding blanks to distinguish between instances of the same polymer units may be performed in step S2. As discussed above, 'optional' and 'compulsory' schemes may be considered for blanks, so step S2 may decode a sequence of labels: AAA - - A to either AAAA, or AA depending on which of the two schemes are followed.

In the case of a flip-flop scheme, step S2 may comprise collapsing multiple runs of the same label to a single corresponding polymer unit. For example, a sequence of labels $CAA^FTACC^FTT^F$ may be decoded in step S2 to the series of polymer units CAATACCTT.

With respect to a multi-stay scheme, step S2 may comprise decoding by identifying consecutive sequences of the same label as different polymer units of the same type. For example, a sequence of labels $AA^SA^STT^SCAA^SA^S$ may be decoded in step S2 to the series of polymer units ATCA.

With respect to a run length encoding scheme, step S2 may comprise decoding by collapsing runs of the same label (and dropping blanks if necessary in the scheme). For example, a sequence of labels $TA^2T^2CA^3$ may be decoded in step S2 to represent the series of polymer units TAATTCAAA.

Step S3 is performed in the case that the weight distributions 51 are factored into dependent distributions, but otherwise omitted. In this case, steps S1 and S2 are performed using the weights that indicate the likelihood of various transitions occurring in the measured data, and in step S3 the quality of the polymer unit represented thereby is determined based on the weights. For example, in the run-length encoded representation described above, the weights are used to estimate the length of the homopolymer. Similarly, in the factored representation of modified forms described above, the weights are used to estimate whether the polymer unit is of the unmodified or modified form.

The estimation of labels in step S1 of the method of FIG. 24 will now be discussed. As the weights represent posterior probabilities of the respective transitions, the weights may be used to derive posterior probabilities for any given path of labels through the weight distributions 51, that is by combining the posterior probabilities represented by the weight for the series of transitions corresponding to the path in question. This means that the weights allow the likelihood of different paths to be considered which improves the accuracy of estimation. Therefore, step S1 applies a technique that is based on consideration of combined weights for transitions corresponding to paths of labels through the weight distributions 51.

Where one or more transitions is not allowed (as discussed above), the estimation performed by the decoder in step S1 may take into account a transition matrix representing whether transitions between labels are allowed or not allowed.

Two different illustrative approaches are described below for purposes of explanation, and are referred to as "best path" and "best label".

In the best path approach, the most likely path of labels through the series of weight distributions 51 is determined based on the weight distributions 51. As the weight distributions 51 are weights over transitions, one way of decoding to estimate a sequence is to find the path that has the maximal sum of weights. Such a path can be found in an efficient manner from the transition weights, for example using a dynamic program algorithm. The Viterbi algorithm may be used.

For example, FIG. 25 illustrates a best path algorithm where the RNN 50 outputs a weight of $w^i_{jk}$ to the transition from label j to label k at block i. The vectors $t^i$ store the traceback information, which is the best label to have come from the given current label, and is used to determine the score S and best path P.

For run-length encoding, the best path found is for the run-length compressed sequence and the length of each run needs to be determined from the appropriate conditional distribution output from by the RNN 50. Where the best path shows that a new polymer unit has occurred, the length of the run is estimated from the conditional distribution corresponding to that polymer unit. Appropriate ways of making this estimate include finding the mean (with rounding), mode or median of the conditional distribution; given a suitable prior, the length with the maximal Bayes factor could also be used. Where a network outputs conditional distributions representing the possible base modifications that might be present, the process for marking up the best path with their presence proceeds similarly albeit that posterior mean and median are not sensible estimators since modifications are categorical rather than ordinal.

For run-length encoding, a run-length bias correction may be applied. Since the model is trained from real reads, there is some prior distribution of run lengths learned and incorporated into the weights of the model. For reads derived from random strands or real (e.g., genomic) strands, there is a remarkably skew in the proportion of runs of different lengths that the training data will contain, for example long runs are extremely rare. This has implications for the ability of the method to call long runs. There is ambiguity in the length of a run, calling short will be correct more often than calling long and so the maximizing single-read accuracy tends to lead to calling runs short. As such, there is benefit in applying a bias correction towards relatively short run-lengths.

Having found the most probable path, a sequence of canonical bases must be derived. For the flip-flop representation, adjacent repeats of a label are merged since they perform the same spacing role as blank labels in other CTC-like models and then the flip or flop identity of each label is scrubbed to leave the canonical base. For run-length encoding, the blank labels are dropped, and each run is expanded out into the appropriate number of bases.

The best label approach will now be discussed, noting that the best path approach may erroneously estimate some particular labels inaccurately where the correct label is not on the most likely path. The weight distributions 51 from the RNN 50 effectively define a probability distribution over all possible paths of labels, consistent ways of assigning labels to positions, and each path corresponds to a series of labels and hence polymer units although this correspondence is not unique (there may be many paths giving the same sequence). The best label approach improves over the best path approach by estimating the series of labels (and hence polymer units) that are most likely. That is, rather than finding the best path, the posterior probability that the path was in label j after time step i can be found by summing over all paths that satisfy this condition. This may take into account forwards and backwards paths of labels through the series of weight distributions 51. In this case, the labels derived in step S1 for the respective weight distributions 51 are the labels thus derived as most likely.

Dynamic programming both forwards and backwards in time allow this calculation to be performed in an efficient manner using a recursion similar to that for the best path; where the best path algorithm can be seen as a form of Viterbi decoding, the calculation of posterior probabilities can be seen as a form of the Forward and Backward algorithms. Similarly, the posterior probability that there was a change of label at time step i can be calculated by summing over all paths satisfying this transition; this calculation can also be performed in an efficient manner.

While the posterior probabilities are informative about the likely label at each position, decoding by picking the mostly like label can result in an inconsistent path and so sequence. By defining a transition matrix T from one label to another whose entries are either one or zero depending on whether the transition is allowed, the best-path decoding algorithm can be applied to these posterior probabilities to find the path that maximizes the sum of the posterior probabilities of its labels from all consistent paths.

As an example of this, FIG. 26 illustrates such an algorithm applied to the posterior probability $p^i_k$ of being in label k at position i. The vectors $t_i$ store the traceback information, which is the best label to have come from given current label, and is used to determine the score S and best path P.

Alternatively the best-path algorithm can be applied to the logarithm of the posterior probabilities to find the path that maximizes the sum of the logarithm posterior probabilities of its labels over all consistent paths. This is equivalent to finding the path that maximizes the product of the posterior probabilities of its labels over all consistent paths.

As an example of this, FIG. 27 illustrates such a best path algorithm applied to the logarithm posterior probability $p^i_k$ of being in label k at position i. The vectors $t_i$ store the traceback information, which is the best label to have come from given current label, and is used to determine the score S and best path P.

Alternatively, since the weight distributions 51 are defined over transitions, the forwards and backwards algorithms can be used to calculate posterior probabilities for the transition taken between positions rather than the label at each position.

As an example of this, FIG. 28 illustrates calculating the posterior probabilities summing over all paths. Since these weights are over transitions, they have the same shape as the transition matrix and their logarithm can fed into the equations defined in FIG. 25 instead of the transition weights to find a consistent path.

One of the more successful approaches to generating a consensus sequence from a number of signals covering the same region of a genome is referred to as 'polishing' and has been described in several publications. Polishing a consensus sequence is an iterative process where candidate changes to a draft consensus sequence are scored by how well all of the reads match them and high scoring changes are kept, allowing mistakes caused by one read to be corrected by the others; this procedure is repeated until no more high scoring changes can be found.

What is not obvious is that polishing can also be beneficially applied to a single-read. All the approaches to estimating the polymer units described in the previous subsections aim to find a good path, through the network outputs, from which a sequence of bases can be extracted, but the registration-free training objective sums over all paths for a given sequence rather than identifying a single path as good. To be consistent with the training criterion, the output from the RNN 50 should ideally be decoded by finding the most probable sequence, summing over all paths that result in the same sequence, rather than most probable path. Summing over all paths for a given sequence is the criterion that polishing uses to assess whether a candidate change is good and so polishing can be thought of as an iterative heuristic, a variant of greedy hill climbing, to find the most probable sequence.

In cases of analyzing plural series of measurements that are measurements of series of polymer units that are related, then the method is fundamentally the same, but the measurements from the plural series of measurements are treated as being arranged in plural, respective dimensions. This increases the dimensionality, but the form of the CN 40 and/or RNN 50 is otherwise the same as described above. Some further considerations that are applicable in this case are as follows.

When using a penalty term, as an alternative to the penalty for not emitting being constant for all transitions, the penalty could take a different value depending on transition or be absent entirely. For example, some transitions result in no change to the state and may be free, or have a small penalty, since they don't imply a missed state in the other read.

The penalty, or penalties, used need not be the same for each read and there may be good biophysical reasons why the two reads may have different characteristics. For example, one read may be from a molecule that was double-stranded above the motor whereas the other was single stranded; alternatively, the two reads may be strands with different motors; one read might be DNA whereas the other might be RNA; alternatively, the two reads may be the first and second parts of the same forward-reverse-complement strand and hybridization between the two during sequencing changes the kinetics.

The penalty, or penalties, used could be time-dependent. The penalty, or penalties, used could be dependent on local statistics of the read. Examples of this include: speed, presence of a stall, or noise. The penalty, or penalties, used could be dependent on the output of an analysis of the read using other models or techniques, predicting the likelihood of slipping (missing bases) for example.

The state transition models of both a flip-flop representation and a RLE representation have a time ordering and reversing the order of states may not be a valid sequence of states. That is, in RLE representation a base must be emitted before staying, and a flip-flop representation requires that the first base of any repeat must be a 'flip'. A consequence of this is that, where one of the reads is from a strand (or part of strand) that is the reverse complement, or reverse, of the other, it is not sufficient to reverse one of the reads before analysis and apply the same procedure as for two forwards reads.

While a more complex procedure could be used to combine reads in two different direction, keeping track of the state of both reads as a pair, it is advantageous to use the standard model on one read and, on the other, one that that has been trained 'backwards'—during training the signal from the read and the target sequence are reversed (and possibly complemented). The use of such a pair of models ensures that both the forward and reverse reads go through the states of the model in the same order and so can be combined as if they were both forwards reads.

Each of the neural networks, CNN 40 and RNN 50, may for instance be trained as follows.

In the case of RNN 50, the network outputs a distribution representing weights representing probabilities over paths of labels (consistent labelling of measures with a label) which is then decoded into an estimate of the sequence of polymer units. The RNN 50 is trained with a criterion that aims to ensure that this estimate has a low proportion of errors.

An important aspect of defining a probability distribution over paths using transition weights is that the weights must be normalized such that the sum over all paths is 1. Given a set of transition weights, the normalization factor can be calculated using dynamic programming by applying the forwards algorithm (or backwards algorithm) as used in the calculation of posterior probabilities as discussed above. Since it is the sum of all possible paths that is normalized to 1 rather than the output of the network at each point in time, this technique is referred to as global normalization and ensures that the score for each path has interpretation as a (logarithm of a) probability. Every path, which has consistent labels, corresponds to a probability and these probabilities form a distribution over all paths.

In contrast to global normalization, normalizing the RNN 50, so that the output at every point in time sums to 1, is referred to as local normalization. The score for each path can be calculated and has the form of a probability but they do not form a distribution since the total probability mass is less than 1. Local normalization assigns probability to all sequences of labels, regardless of whether they form a consistent path.

The training for sequence labelling requires training examples, that is pairs of input signals and their corresponding sequence of labels, as well as an objective function to optimize over the training examples. Since the true registration between the nanopore measurements and the sequence of polymer units is unknown, registration-free training methods like those described in Graves et al. (2006) are preferred. Where registered training methods require each element of the sequence of measurements to be labelled, registration-free methods only require the true sequence of polymer units to be known. The true sequence of polymer units for a read can be determined by measuring polymers of known sequence in the nanopore device or comparing the reads to a reference sequence or set of measurements with known sequence.

Examples of measurements of known sequence may include small genomes, where it is possible to sequence the complete genome in a single read such as lambda phage (50 kilobases). Restriction digests may also be used, and fragments identified by their length. Another example involves adding known fragments sequentially to a run, which are therefore identifiable by the time at which they appear in the data. It will be apparent that any method that can assign sequence to signal reads may be used.

When training the RNN 50, it is beneficial to have measurements spanning each polymer unit in a variety of contexts, and over a variety of experiments, so the network has been exposed to much of the full range of variation it will encounter under normal running conditions. Ideally, The RNN 50 is trained using complete reads, i.e., pairs of signal and sequence that cover full length polymers, as read by the nanopore. However, for practical considerations (compute time, memory), it is typical to operate over smaller chunks of signal and sequence.

Recurrent, convolutional and attention neural network units have a concept of time order and the size of the window of measurements presented in training limits the context that can be learnt from. Because of the large range of influence each polymer unit can have, it is beneficial to present the RNN 50 with a large window of measurements to train from. The size of the window used is a balance between presenting a sufficiently large sequence of measurements that the RNN 50 can create an adequate internal representation of the interaction between the pore, the polymer strand and the other system components, and the amount of computational power available. Ideally the entirety of each read would be used, but in practice fixed sized chunks of measures present a good compromise. The size of chunks that are adequate depend on the nanopore, and the rate of translocation of the strand, but a chunk size corresponding to around 200 to around 300 bases has proven adequate. For example, this has proven adequate for a CsgG nanopore.

An example training set size may comprise~1 million sets of ~300 base chunks of signal and sequence. Smaller training sets of only a few thousand chunks may be sufficient, and larger training sets >1 million chunks may provide more diversity for the training.

Many techniques of training a neural network, or other machine learning method, are known to the art and may be applied here. Since the ability of the method to generalize to different experimental runs and polymer sequences benefits from a large set of training data, it is often impractical to seek to maximize the objective function direction as it is preferred to perform the calculations on Graphical Processing Units (GPUs), or other specialized hardware, are memory limited. Rather than directly maximize the objective function over the full set of data, it is preferred to approximately maximize it using Stochastic Gradient Descent (SGD), or related techniques, in an iterative fashion using subsets ("minibatches") of the full training set. The minibatch size preferred depends on the available memory on the computational device used and the number of measures in each element of the minibatch.

Many variants of Stochastic Gradient Descent (SGD) are known to the art, for example: SGD, SGD with momentum, SGD with Nesterov momentum, RMSprop, AdaMax, Adam. A modification of Adam, "Adamski", in which the momentum for iteration N increases by a momentum ramping factor r from 0 to a maximum value μ: where $\mu_N = \mu(1-e^{-rN})$, is preferred. Adamski has a learning rate, two smoothing parameters (often referred to as decay1 and decay2 in the art) and a momentum ramping rate. Many choices of these parameters are beneficial. The preferred parameterization has an initial learning rate of $10^{-3}$, smoothing parameters of 0.9 and 0.999 and momentum ramping factor of 0.005. Smoothing parameters of 0.95 and 0.99 have also proven effective for refining an already trained model, as has dropping the initial learning rate to $10^{-4}$.

SGD and related techniques proceed iteratively, each iteration consisting of the following steps:
1. Pick a subset of the full training data.
2. Calculating the objective function for this subset
3. Calculate gradient for all network parameters using backpropagation
4. Update network parameters using SGD or variant
5. Go to 1 (start of next iteration)

The size of the update in step 4 is scaled by a factor known as the learning rate. A high learning rate means the parameters can change rapidly, and so maximization can proceed more quickly, but the effect of each minibatch can be large, meaning that updates when the model is close to convergence can be dominated by minibatch to minibatch variability. It is preferred to slowly reduce the learning rate from iteration to iteration; this reduction can be dynamic, adjusting to the learning rate according the change and variability of the objective function from batch to batch, or according to some predetermined schedule. For preference, a hyperbolic decay is used where the learning rate for the $N^{th}$ minibatch is $R/(1+(N/K))$ for some initial learning rate R and number of minibatches K.

While summation has been used to combine the score for each member of the minibatch together into the score for the minibatch, other methods of combination are possible. Summation results in a minibatch score that is proportional to the mean of the scores of its constituent elements, combinations corresponding to other measures of central trend also have favorable properties. Combinators such as the median, trimmed or weighted mean, or fitting an M-estimator can be used to change the sensitivity of the objective to minibatch elements with outlier values.

The contribution from each element of the minibatch to the total score is the (logarithm of the) posterior probability of the true sequence summed over all consistent paths. For the flip-flop representation, transitions of flip-to-flip or flop-to-flop represent staying in the same position of the sequence whereas all other transitions involve a move of a position. Given weights representing transitions between labels output from the RNN 50 at each time point, these can be converted into transition weights between positions of a known sequence.

FIG. 29 shows how to construct the elements of the objective transition matrix mi for each time point i for a flip-flop encoded sequence of labels $S_1, S_2, \ldots, S_N$. The objective function, described in FIG. 30 uses this objective transition matrix to calculate the score for each element of the minibatch.

Since the transition matrix for the objective function is extremely sparse, only having non-zero elements on the diagonal (stay) and super-diagonal (move on position), the preferred embodiment of this calculation only ignores the zero elements and reduces the apparent complexity of each step, in terms of the length of the true sequence, from quadratic to linear.

The objective function for the multi-stay representation is structurally similar to the flip-flop objective but the states representing staying in the same position are different. A transition from a stay or non-stay state to any non-stay state implies a change of position; any transition to stay state does not. For the multi-stay representation, the transitions representing staying in a new position (base to stay transition) and staying in an old position (stay to stay transition) are distinguished and efficient calculation of the objective function requires the use of a duplicate set of "remain" positions for the true sequence: $S_1, R_1, S_2, R_2 \ldots, S_N, R_N$.

FIG. 31 shows how to construct the elements of the objective transition matrix for this example. For the purposes of forming the objective transition matrix, the original positions are enumerated 1 . . . N, whereas the corresponding duplicated positions are enumerated N+1 . . . 2N.

The objective function described in FIG. 30 uses this objective transition matrix to calculate the score for each element of the minibatch. The objective transition matrices are sparse and the preferred embodiment of the objective calculation takes advantage of this sparsity.

According to some embodiments, each score of the objective transition matrix could be multiplied by a weight before being used in the objective function, and this weight may represent the value of the corresponding element of the minibatch to the training process. The weight may, for example, be larger for elements with an unusual sequence composition or one that is known to be involved in base calling errors, which may be found during testing of previously trained network. One method of determining a weight for an element of the minibatch is set it equal to the inverse of the frequency of its rarest homopolymer, the frequencies determined from the whole of the set of training data or from other external reference.

The objective for run-length encoding is defined similarly to that for multi-stay model but an additional factor incorporated whenever a new sequence position is transitioned to representing how well the length of the run is predicted by the corresponding conditional distribution output by the network. The form of the objective transition matrix over the run length compressed sequence has the same form as that for the many stay objective, the restriction that no base can follow the same base being implicit in the allowed transitions between positions, but with an additional component from the log-probability that the network assigns to the length of the homopolymer at each position given its composition.

When the homopolymer content of the training data is known to be skewed, it can be undesirable in many applications for the network to learn this skew since it may not be representative of other sets of data. Instead of using the log-probability that the network assigns to the length of the homopolymer at each position given its composition directly in the training objective, it can first be combined with another distribution; this other distribution could be obtained by tabulating frequencies of homopolymers from the training data ("training prior distribution"). By training in this manner, the network may learn to assign log-probabilities that overcome the expectations of the training prior distribution.

For the purposes of basecalling, the prior distribution from the training data, or any other expectation of homopolymer lengths, could be combined with the log-probability assigned by the network using standard methods, such as Bayes theorem, to produce a new log-probability informed by external information about the homopolymer length; alternatively, the log-probability from the network could be used directly for an unbiased call.

FIG. 32 shows how to construct the elements of the objective transition matrix for this example. Letting the logarithm of the probability that the network assigns to a run of length $L_j$ with composition $S_j$ for position j of the sequence at time step i of the measurements be $r^iS_j:L_j$. The objective function described in FIG. 30 uses this objective transition matrix to calculate the score for each element of the minibatch.

Figure 33:
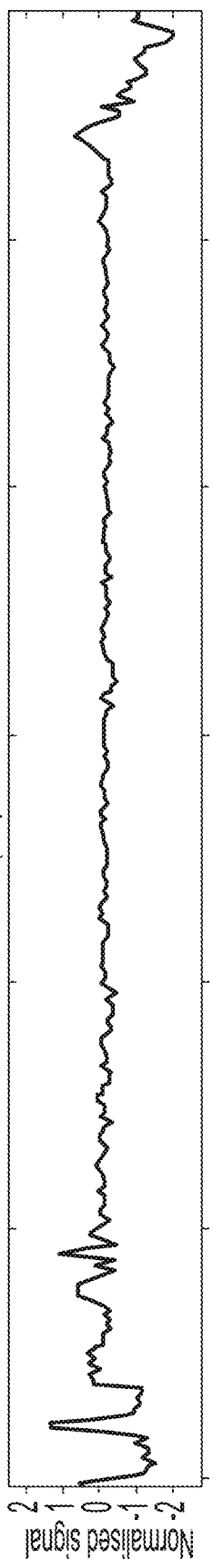
FIG. 33 is a plot of a signal and polymer units estimated therefrom illustrating an example of a long homopolymer.

While the advantages of training basecalling models in a registration-free manner are numerous, there is a disconnect between most of the decoding algorithms presented and the training objective used. The objective function for model training is to maximize the probability of the true sequence of bases, summing over the probabilities of all the individual paths that could represent it, whereas all of the decode routines, other than polishing as described above are looking to find a path with a high score. FIG. 33 shows one of the issues caused by this disconnect. FIG. 33 shows the signal (top) and posterior probabilities (bottom) of being in a particular label over time for an example of a flip-flop representation, in case where there is a long homopolymer region between times 2410 and 2600, approximately, where the models stays in the T-flop state (red dashed line) rather than alternating with the T-flip state (red solid line). Having entered a long homopolymer, estimates are made around the start and end of the region but the flip and flop states quickly become less distinct and the posterior probabilities even out. There are multiple paths through the region where the registration of the flip and flop bases are slightly different and the posterior probabilities reflect an average of this ensemble.

One possible alternative is using the score of the best path as a training objective, rather than summing over all paths, and this would still be registration-free method since no registration is explicitly defined and, unlike labelling, the best registration may change as the model does. While training to the best path seems intuitive, this approach fails quite drastically when training a model from scratch since the initial poor model has a bad best path and the training process reinforces to it.

Figure 34:
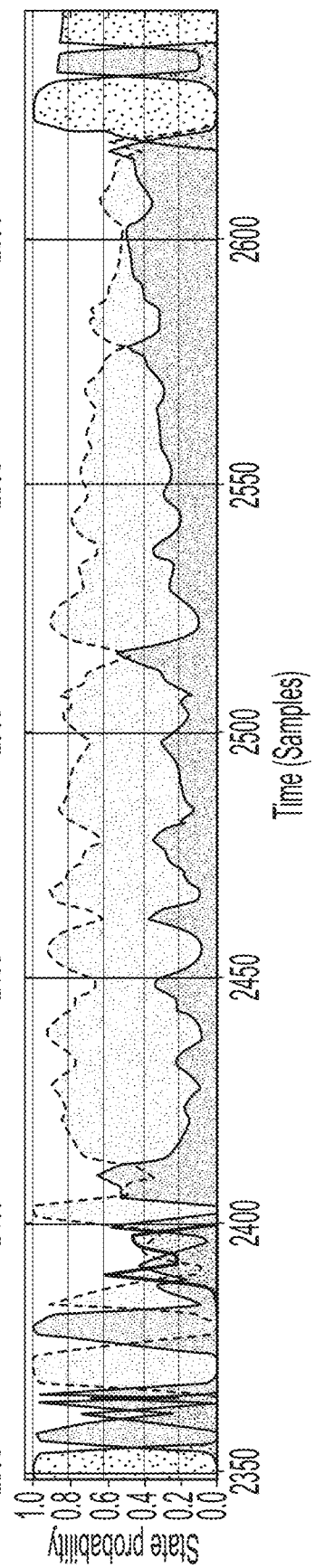
FIG. 34 is a definition of an objective function for training for the best path.

Sharpening is a way of focusing the training towards a single path, without having to specify that registration in advance, while still considering all other possibilities. Firstly, consider the algorithms for calculating the score for the sum over all-paths (FIG. 30) and that of the best-path (FIG. 34). Both of these apply a functor, $\log \Sigma_j \exp$ and $\max_j$ respectively, to combine the transition weights and previous forward vector together. The goal of sharpening is to replace this functor with one that still sums over all possible paths but up-weights those that score highly.

Figures 35, 36:
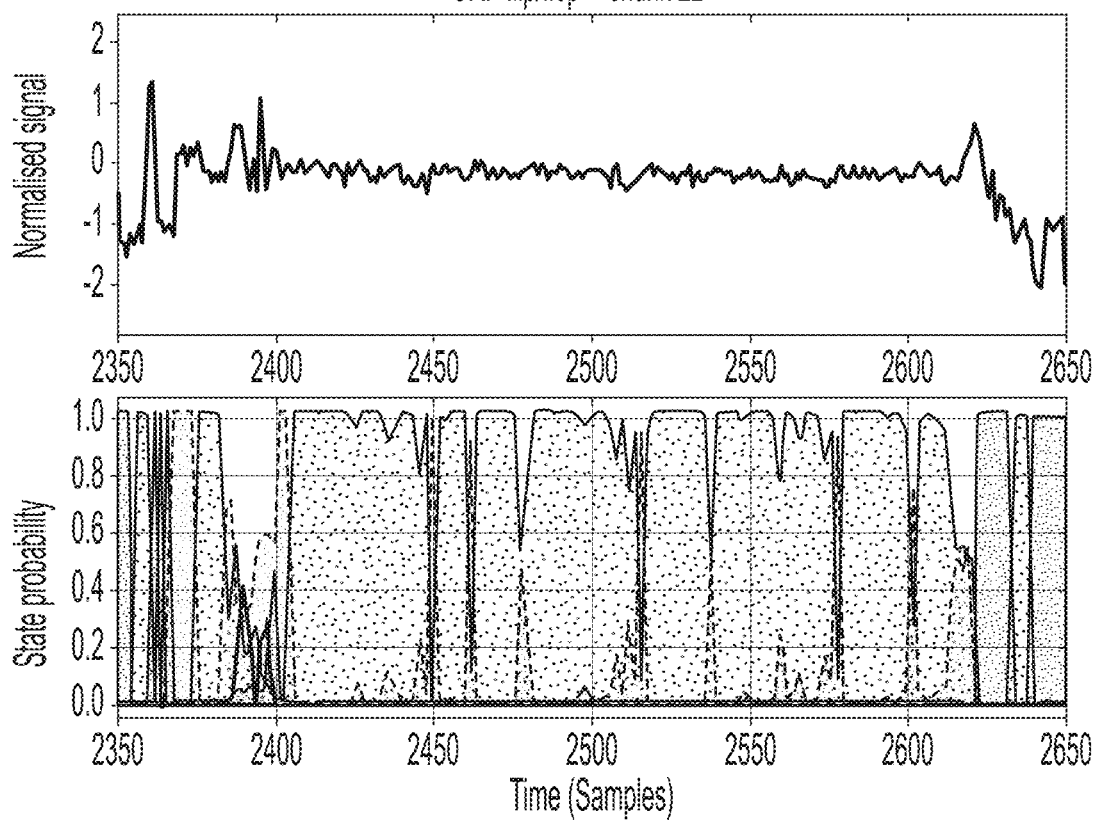
FIG. 35 is a table of functors.
FIG. 36 is a plot of a signal and polymer units estimated therefrom illustrating an example where a flip-flop representation is trained using sharpening.

FIG. 35 shows some functors that may be functions used to combine the forwards vector and transitions or mapping weights together. The functor referred to as 'sharpened all paths' in FIG. 35 is preferred but many others can be used and, indeed, combined together to create new functors.

Rather than training with sharpening enabled from the beginning, it has been found to be advantageous to start training using an all-paths objective function and then increasing the sharpening factor (a) from 1 to a higher value once a good model has been found, potentially repeating with even higher values of sharpening. This multiple-stage process also enables models to train using the best-path objective. Training first to the all paths objective finds a good model such that the best path is good and then this path gets reinforced by further training.

FIG. 36 shows the effect of sharpening a flip-flop representation on the same example region as shown in FIG. 33. FIG. 36 shows the signal (top) and posterior probabilities (bottom) of being in a particular state over time for this example but with training using sharpening. There is a long region between times 2400 and 2620, approximately, where a homopolymer occurs and the model alternates between the T-flop state and T-flip state to call the sequence of bases. The individual calls are more distinct and can be seen to alternate between T-flip and T-flop throughout the homopolymer region.

Decoding this model results in a superior estimation of the polymer units to that of the unsharpened model. This is illustrated in the example shown in FIG. 37, wherein estimates of the polymer unit (basecalls) from unsharpened and sharpened models are compared to the reference sequence. Whereas the unsharpened call only calls 8 T bases, the sharpened call agrees the 27 T bases found in the reference.

Whereas using the best-path or sharpening replaces the training objective, these approaches could also be used to augment the training objective and train the network away from undesirable behavior that has been found during testing. One such undesirable behavior might be a tendency to under-call the lengths of homopolymers, which can occur when the training data is heavily skewed towards short homopolymers, and can be corrected by adding a penalty to the training objective. One such penalty can be found by using the best-path to find positions where homopolymers are called and comparing their true length with an estimate based on the log-probabilities assigned by the network at that position; the comparison could be performed using the sum of absolute differences; the comparison could be performed using the sum of squared difference; many other methods of comparison are known in the art. The penalty could be added to the training objective; the penalty could additionally be weighted by a predetermined factor to change it importance relative to the training objective.

Rather than being predetermined, the factor weighting the penalty term could be treated as a Lagrange multiplier. Training proceeds by the optimizing the training objective while finding a stationary point for the Lagrange multiplier. At, or near these points, the penalty is approximately zero and the network has been trained subject to the penalty condition holding; for the example of where the penalty is the sum of absolute differences between the true and estimated length, the network calls will be the correct length on average.

Multiple penalty terms can be used to augment the training objective, one for each homopolymer length for example; each penalty may either be weighted by a predetermined factor or be treated as a Lagrange multiplier.

The above description considers the case that the weight distributions 51 represent transitions between a set of labels. As an alternative, the methods described herein can be adapted to a case in which the weight distributions 51 represent labels within the set of labels.

In this case in which the weight distributions 51 represent labels within the set of labels, the decoder 80 may use a transition matrix to represent whether transitions between labels are allowed or not allowed. The transition matrix may have a similar form to the matrix of weights in the weight distributions 51 but with binary elements indicating the transitions as allowed or not allowed. The transition matrix may represent at least one transition as not allowed and other transitions being represented as allowed. The decoder 80 may use this transition matrix to derive an estimate of the series of polymer units from the weight distributions 51 that represent labels taking into account the likelihood of different paths through the labels that are allowed in accordance with the transition matrix.

Also in this case in which the weight distributions 51 represent labels within the set of labels, consecutive instances of polymer units of the same type in the series of polymer units may be represented in an encoded form as described above, for example using a flip-flop representation or a run-length encoded representation.

While the above description describes processing operations 20 that include RNN 50, weight distributions having the form and decoding described above may equally be applied to any other form of machine learning technique, for example an HMM.

According to a first aspect of the present invention, there is provided a method of analysis of a signal derived from a polymer during translocation of the polymer with respect to a nanopore, the polymer comprising a series of polymer units belonging to a set of possible types of polymer unit, the method comprising: analyzing the signal using a machine learning technique that outputs a series of weight distributions, each weight distribution comprising weights in respect of transitions between labels over a set of labels including labels representing the possible types of polymer unit; and deriving an estimate of the series of polymer units from the weight distributions. The set of labels can include labels representing blanks and/or stays. In other words, the set can be said to represent the possible types of polymer units.

The transitions can be between one label and another. The transmissions can be between consecutive labels.

Thus, the method provides weights that refer to labels which represent the possible types of polymer unit, rather than representing a k-mer comprising k polymer units. However, the method derives weights in respect of transitions between labels, rather than weights in respect of the labels themselves. Such a method provides advantages over a comparative method that derives a series of weights in respect of labels over a set of labels including labels that represent the possible types of polymer unit. By providing weights in respect of transitions between labels over the set of labels, additional information is provided that permits estimation of the series of polymer units in a manner that is more accurate. This is because the weights provide information on possible paths of labels, whereas weights in respect of labels do not.

For example, there are situations where a label for a particular position that is predicted by weights in respect of the labels is not correct, whereas a consideration of the paths of labels through that position may predict a different label that is correct. In this manner additional information is fed into the estimate, thereby improving the accuracy.

By way of example, this technique allows better estimation of regions of repetitive sequences, e.g., homopolymers, including regions where short sequences of one or more polymer units are repeated.

Preferably, at least one transition between labels is not allowed and other transitions are allowed, the weight distributions each comprising weights in respect of transitions that are allowed. In that case, the weight distributions may each comprise null weights in respect of transitions that are not allowed or the step of deriving an estimate of the series of polymer units may take into account a transition matrix representing whether transitions between labels are allowed or not allowed.

In one type of representation, the set of labels may include a first and a second label in respect of each type of polymer unit, the first label representing the start of an instance of the type of polymer unit, and the second label representing a stay in the instance of the type of polymer unit, wherein transitions from each first label to the first label for any other type of polymer unit are allowed, transitions from each first label to the first label for the same type of polymer unit are allowed, transitions from each first label to the second label for the same type of polymer unit are allowed, transitions from each first label to the second label for any other type of polymer unit are not allowed, transitions from each second label to the first label for the same type of polymer unit or the first label for any other type of polymer unit are allowed, and transitions from each second label to the second label for the same type of polymer unit are allowed, and transitions from each second label to the second label for any other type of polymer unit are not allowed.

A "stay" represents a situation in which the method determines that the label does not change, which may be considered as two weight distributions corresponding to the same instance of a polymer unit.

The set of possible types of polymer unit may include a type of polymer unit that always appears in a known sequence of polymer units, transitions in accordance with the known sequence being allowed and transitions contrary to the known sequence being not-allowed.

The labels consecutive instances of polymer units of the same type in the series of polymer units may be represented in an encoded form.

The labels may include plural labels, for example two labels, in respect of each type of polymer unit, wherein the plural labels in respect of each type of polymer unit represent consecutive instances of the type of polymer unit in the series of polymer units.

The plural labels for each type of polymer unit may have a predetermined cyclical order, whereby some transitions between labels are allowed by the predetermined cyclical order and other transitions between are not allowed by the predetermined cyclical order, the weight distributions including weights in respect of transitions that are allowed by the predetermined cyclical order.

The consecutive instances of the same type of polymer unit in the series of polymer units are represented in in a run-length encoded form.

The labels may include labels in respect of different run-lengths of each type of polymer unit.

The labels may include a label in respect of each type of polymer unit, and the weight distributions may comprise further weights over possible lengths of consecutive instances of the same type of polymer unit for each type of polymer unit.

The further weights may comprise a categorical distribution of weights over a set of possible lengths of consecutive instances of the same type of polymer unit for each type of polymer unit.

The further weights may comprise parameters of a parameterized distribution over possible lengths of consecutive instances of the same type of polymer unit for each type of polymer unit.

If the possible types of polymer unit include a type of polymer unit that has unmodified and modified forms, then the set of labels may include a label representing the type of polymer unit that has unmodified and modified forms, and each weight distribution may comprise further weights for the unmodified and modified forms of each of said at least one type of polymer unit that has the unmodified and modified forms. The unmodified form of a polymer unit may be described as a canonical polymer unit and the modified form of a polymer unit may be described as a non-canonical polymer unit. A modified (or non-canonical) polymer unit typically affects a signal differently from a corresponding unmodified (canonical) polymer unit.

In some embodiments, a polymer comprising one or more non-canonical polymer units may be prepared and subsequently analyzed as described in detail in International Patent Application No. PCT/GB2019/052456, filed 4 Sep. 2019, to which reference is made and which is incorporated herein by reference. In one example, a proportion of canonical polymer units (e.g., amino acids) may be converted to a corresponding non-canonical polymer unit (e.g., amino acid) in a non-deterministic manner, e.g., by chemical conversion or by enzymatic conversion. In that case, when deriving an estimate of the series of polymer units ("calling"), the non-canonical bases may be estimated ("called) as being the corresponding canonical base. In this manner, by recognizing a non-canonical polymer unit as a canonical polymer unit in the analysis, the initial conversion can provide a way to provide a signal with more information, for example having a consequence that any errors present in the analysis of the signal will be non-systematic, thereby leading to an improvement in the accuracy of the estimation.

The set of labels may include at least one label in respect of each type of polymer unit and at least one label in respect of a blank in the series of polymer units.

The machine learning technique may be a neural network comprising at least one recurrent layer, which may be a bidirectional recurrent layer.

The neural network may apply a global normalization of the weight distributions over all paths through the series of weight distributions.

The neural network may include plural convolutional layers arranged before the recurrent layers and which perform a convolution of windowed sections of signal.

The weights may represent posterior probabilities.

The step of deriving an estimate of the series of polymer units from the weight distributions may be performed using connectionist temporal classification.

The step of deriving an estimate of the series of polymer units from the weight distributions may comprises deriving a label in respect of each weight distribution and run-length compressing the derived labels.

The step of deriving an estimate of the series of polymer units from the weight distributions may comprise estimating the most likely path of labels through the series of weight distributions on the basis of the weight distributions, the estimate of the series of polymer units being derived from the path of labels estimated as most likely.

Alternatively, the step of deriving an estimate of the series of polymer units from the weight distributions may comprise estimating the labels that are most likely in respect of each weight distribution, taking into account forwards and backwards paths of labels through the series of weight distributions, the estimate of the series of polymer units being derived from the labels estimated as most likely.

According to a second aspect of the present invention, there is provided a method of analysis of a signal derived from a polymer during translocation of the polymer with respect to a nanopore, the polymer comprising a series of polymer units belonging to a set of possible types of polymer unit, the method comprising: analyzing the signal using a machine learning technique that outputs a series of weight distributions, each weight distributions comprising weights in respect of labels over a set of labels including labels representing the possible types of polymer unit; and deriving an estimate of the series of polymer units from the weight distributions, wherein the step of deriving an estimate of the series of polymer units takes into account a transition matrix representing whether transitions between labels are allowed or not allowed, at least one transition between labels being represented as not allowed and other transitions being represented as allowed.

According to a third aspect of the present invention, there is provided a method of analysis of a signal derived from a polymer during translocation of the polymer with respect to a nanopore, the polymer comprising a series of polymer units belonging to a set of possible types of polymer unit, the method comprising: analyzing the signal using a machine learning technique that outputs a series of weight distributions, each weight distributions comprising weights in respect of labels over a set of labels including labels representing the possible types of polymer unit, wherein consecutive instances of the same type of polymer unit in the series of polymer units are represented in a run-length encoded form; and deriving an estimate of the series of polymer units from the weight distributions.

Any features of the first aspect can apply in any combination to the second and third aspects of the invention.

Further according to the present invention, the method may be implemented by a computer program executed in a computer apparatus or there may be provided an analysis apparatus arranged to implement a similar method to any of the aspects of the present invention.

Yet further according to the present invention, there may be provided a nanopore measurement and analysis system comprising such an analysis apparatus in combination with a measurement system arranged to derive a signal from a polymer during translocation of the polymer with respect to a nanopore.

A1. A method of analysis of a signal derived from a polymer during translocation of the polymer with respect to a nanopore, the polymer comprising a series of polymer units belonging to a set of possible types of polymer unit, the method comprising analysing the signal using a machine learning technique that outputs a series of weight distributions, each weight distribution comprising weights in respect of transitions between labels over a set of labels, including labels representing the possible types of polymer unit; and deriving an estimate of the series of polymer units from the weight distributions.

A2. A method according to claim A1, wherein at least one transition between labels is not allowed and other transitions are allowed, the weight distributions each comprising weights in respect of transitions that are allowed.

A3. A method according to claim A2, wherein the weight distributions each comprise null weights in respect of transitions that are not allowed.

A4. A method according to claim A2 or A3, wherein the step of deriving an estimate of the series of polymer units takes into account a transition matrix representing whether transitions between labels are allowed or not allowed.

A5. A method according to any one of claims A2 to A4, wherein the set of labels include a first and a second label in respect of each type of polymer unit, the first label representing the start of an instance of the type of polymer unit, and the second label representing a stay in the instance of the type of polymer unit, wherein transitions from each first label to the first label for any other type of polymer unit are allowed, transitions from each first label to the first label for the same type of polymer unit are allowed, transitions from each first label to the second label for the same type of polymer unit are allowed, transitions from each first label to the second label for any other type of polymer unit are not allowed, transitions from each second label to the first label for the same type of polymer unit or the first label for any other type of polymer unit are allowed, and transitions from each second label to the second label for the same type of polymer unit are allowed, and transitions from each second label to the second label for any other type of polymer unit are not allowed.

A6. A method according to any one of claims A2 to A5, wherein the set of possible types of polymer unit includes a type of polymer unit that always appears in a known sequence of polymer units, transitions in accordance with the known sequence being allowed and transitions contrary to the known sequence being not allowed.

A7. A method according to any one of the preceding claims, wherein consecutive instances of polymer units of the same type in the series of polymer units are represented in an encoded form.

A8. A method according to claim A7, wherein the labels include plural labels in respect of each type of polymer unit, wherein the plural labels in respect of each type of polymer unit represent consecutive instances of the type of polymer unit in the series of polymer units.

A9. A method according to claim A8, wherein the plural labels for each type of polymer unit have a predetermined cyclical order, whereby some transitions between labels are allowed by the predetermined cyclical order and other transitions between are not allowed by the predetermined cyclical order, the weight distributions each including weights in respect of transitions that are allowed by the predetermined cyclical order.

A10. A method according to claim A8 or A9, wherein the plural labels for each type of polymer unit are two labels for each type of polymer unit.

A11. A method according to claim A7, wherein consecutive instances of the same type of polymer unit in the series of polymer units are represented in a run-length encoded form.

A12. A method according to claim A11, wherein the labels include plural labels in respect of different run-lengths of each type of polymer unit.

A13. A method according to claim A11, wherein the labels include a label in respect of each type of polymer unit, and the weight distributions comprise further weights over possible lengths of consecutive instances of the same type of polymer unit for each type of polymer unit.

A14. A method according to claim A13, wherein the further weights comprise a categorical distribution of weights over a set of possible lengths of consecutive instances of the same type of polymer unit for each type of polymer unit.

A15. A method according to claim A13, wherein the further weights comprise parameters of a parameterised distribution over possible lengths of consecutive instances of the same type of polymer unit for each type of polymer unit.

A16. A method according to any one of the preceding claims, wherein the possible types of polymer unit include a type of polymer unit that has unmodified and modified forms.

A17. A method according to claim A16, wherein the set of labels include a label in respect of the type of polymer unit that has unmodified and modified forms.

A18. A method according to claim A17, wherein each weight distribution comprises further weights for the unmodified and modified forms of each of the type of polymer unit that has the unmodified and modified forms.

A19. A method according to any one of the preceding claims, wherein the set of labels includes at least one label representing each type of polymer unit.

A20. A method according to claim A1, wherein the set of labels further include at least one label representing a blank and/or a stay in the series of polymer units.

A21. A method according to any one of the preceding claims, wherein the machine learning technique is a neural network comprising at least one recurrent layer.

A22. A method according to claim A21, wherein the at least one recurrent layer is a bidirectional recurrent layer.

A23. A method according to claim A21 or A22, wherein the neural network applies a global normalization of the weight distributions over all paths of labels through the series of weight distributions.

A24. A method according to any one of claims A21 to A23, wherein the neural network includes at least one convolutional layer arranged before the at least one recurrent layer and which performs a convolution of windowed sections of the signal.

A25. A method according to any one of the preceding claims, wherein the weights represent posterior probabilities.

A26. A method according to any one of the preceding claims, wherein the step of deriving an estimate of the series of polymer units from the weight distributions is performed using connectionist temporal classification.

A27. A method according to any one of the preceding claims, wherein the step of deriving an estimate of a polymer unit from the weight distributions comprises deriving a label in respect of respective weight distribution and run-length compressing the derived labels.

A28. A method according to any one of the preceding claims, wherein the step of deriving an estimate of the series of polymer units from the weight distributions comprises estimating the most likely path of labels through the series of weight distributions on the basis of the weight distributions, and deriving the estimate of the series of polymer units from the path of labels estimated as most likely.

A29. A method according to any one of claims A1 to A24, wherein the step of deriving an estimate of the series of polymer units from the weight distributions comprises estimating the labels that are most likely in respect of each weight distribution, taking into account forwards and backwards paths of labels through the series of weight distributions, and deriving the estimate of the series of polymer units from the labels estimated as most likely.

A30. A method according to any one of the preceding claims, wherein the nanopore is a protein pore.

A31. A method according to any one of the preceding claims, wherein the polymer is a polynucleotide, and the polymer units are nucleotides.

A32. A method according to any one of the preceding claims, wherein the signal is derived from measurements of one or more of the following properties: ionic current, impedance, a tunnelling property, a field effect transistor voltage and an optical property.

A33. A method according to any one of the preceding claims, the method being performed in a computer apparatus.

A34. A method according to any one of the preceding claims, further comprising deriving the signal from the polymer during translocation of the polymer with respect to a nanopore.

A35. An analysis apparatus for analysing a signal derived from a polymer during translocation of the polymer with respect to a nanopore, the polymer comprising a series of polymer units belonging to a set of possible types of polymer unit, the analysis apparatus comprising: a machine learning unit arranged to perform a machine technique on the signal and to output a series of weight distributions, each weight distributions comprising weights in respect of transitions between labels over a set of labels including labels representing the possible types of polymer unit; and an estimation unit arranged to derive an estimate of the series of polymer units from the weight distributions.

A36. A nanopore measurement and analysis system comprising: a measurement device arranged to derive a signal from a polymer during translocation of the polymer with respect to a nanopore; and an analysis apparatus according to claim A35.

A37. A method of analysis of a signal derived from a polymer during translocation of the polymer with respect to a nanopore, the polymer comprising a series of polymer units belonging to a set of possible types of polymer unit, the method comprising: analysing the signal using a machine learning technique that outputs a series of weight distributions, each weight distribution comprising weights in respect of labels over a set of labels including labels representing the possible types of polymer unit; and deriving an estimate of the series of polymer units from the weight distributions, wherein the step of deriving an estimate of the series of polymer units takes into account a transition matrix representing whether transitions between labels are allowed or not allowed, at least one transition between labels being represented as not allowed and other transitions being represented as allowed.

A38. An analysis apparatus for analysing a signal derived from a polymer during translocation of the polymer with respect to a nanopore, the polymer comprising a series of polymer units belonging to a set of possible types of polymer unit, the analysis apparatus comprising: a machine learning unit arranged to perform a machine technique on the signal and to output a series of weight distributions, each weight distributions comprising weights in respect of labels over a set of labels including labels representing the possible types of polymer unit; and an estimation unit arranged to derive an estimate of the series of polymer units from the weight distributions, wherein the estimation unit is arranged to takes into account a transition matrix representing whether transitions between labels are allowed or not allowed, at least one transition between labels being represented as not allowed and other transitions being represented as allowed.

A39. A method of analysis of a signal derived from a polymer during translocation of the polymer with respect to a nanopore, the polymer comprising a series of polymer units belonging to a set of possible types of polymer unit, the method comprising: analysing the signal using a machine learning technique that outputs a series of weight distributions, each weight distributions comprising weights in respect of labels over a set of labels including labels representing the possible types of polymer unit, wherein consecutive instances of the same type of polymer unit in the series of polymer units are represented in a run-length encoded form; and deriving an estimate of the series of polymer units from the weight distributions.

A40. An analysis apparatus for analysing a signal derived from a polymer during translocation of the polymer with respect to a nanopore, the polymer comprising a series of polymer units belonging to a set of possible types of polymer unit, the analysis apparatus comprising: a machine learning unit arranged to perform a machine technique on the signal and to output a series of weight distributions, each weight distributions comprising weights in respect of labels over a set of labels including labels representing the possible types of polymer unit, wherein consecutive instances of the same type of polymer unit in the series of polymer units are represented in a run-length encoded form; and an estimation unit arranged to derive an estimate of the series of polymer units from the weight distributions.

A41. A method according to claim A37, wherein at least one transition between labels is not allowed and other transitions are allowed, the weight distributions each comprising weights in respect labels that are allowed.

A42. A method according to claim A41, wherein the weight distributions each comprise null weights in respect labels that are not allowed.

A43. A method according to claim A41 or A42, wherein the step of deriving an estimate of the series of polymer units takes into account a transition matrix representing whether transitions between labels are allowed or not allowed.

A44. A method according to any one of claims A41 to A43, wherein the set of labels include a first and a second label in respect of each type of polymer unit, the first label representing the start of an instance of the type of polymer unit, and the second label representing a stay in the instance of the type of polymer unit, wherein transitions from each first label to the first label for any other type of polymer unit are allowed, transitions from each first label to the first label for the same type of polymer unit are allowed, transitions from each first label to the second label for the same type of polymer unit are allowed, transitions from each first label to the second label for any other type of polymer unit are not allowed, transitions from each second label to the first label for the same type of polymer unit or the first label for any other type of polymer unit are allowed, and transitions from each second label to the second label for the same type of polymer unit are allowed, and transitions from each second label to the second label for any other type of polymer unit are not allowed.

A45. A method according to any one of claims A41 to A44, wherein the set of possible types of polymer unit includes a type of polymer unit that always appears in a known sequence of polymer units, transitions in accordance with the known sequence being allowed and transitions contrary to the known sequence being not allowed.

A46. A method according to any one of claims A41 to A45, wherein consecutive instances of polymer units of the same type in the series of polymer units are represented in an encoded form.

A47. A method according to claim A46, wherein the labels include plural labels in respect of each type of polymer unit, wherein the plural labels in respect of each type of polymer unit represent consecutive instances of the type of polymer unit in the series of polymer units.

A48. A method according to claim A47, wherein the plural labels for each type of polymer unit have a predetermined cyclical order, whereby some transitions between labels are allowed by the predetermined cyclical order and other transitions between are not allowed by the predetermined cyclical order, the weight distributions each including weights in respect labels that are allowed by the predetermined cyclical order.

A49. A method according to claim A47 or A48, wherein the plural labels for each type of polymer unit are two labels for each type of polymer unit.

A50. A method according to claim A46, wherein consecutive instances of the same type of polymer unit in the series of polymer units are represented in a run-length encoded form.

A51. A method according to claim A50, wherein the labels include plural labels in respect of different run-lengths of each type of polymer unit.

A52. A method according to claim A50, wherein the labels include a label in respect of each type of polymer unit, and the weight distributions comprise further weights over possible lengths of consecutive instances of the same type of polymer unit for each type of polymer unit.

A53. A method according to claim A52, wherein the further weights comprise a categorical distribution of weights over a set of possible lengths of consecutive instances of the same type of polymer unit for each type of polymer unit.

A54. A method according to claim A52, wherein the further weights comprise parameters of a parameterised distribution over possible lengths of consecutive instances of the same type of polymer unit for each type of polymer unit.

A55. A method according to any one of claims A41 to A54, wherein the possible types of polymer unit include a type of polymer unit that has unmodified and modified forms.

A56. A method according to claim A55, wherein the set of labels include a label in respect of the type of polymer unit that has unmodified and modified forms.

A57. A method according to claim A56, wherein each weight distribution comprises further weights for the unmodified and modified forms of each of the type of polymer unit that has the unmodified and modified forms.

A58. A method according to any one of claims A41 to A57, wherein the set of labels includes at least one label representing each type of polymer unit.

A59. A method according to claim A37, wherein the set of labels further include at least one label representing a blank and/or a stay in the series of polymer units.

A60. A method according to any one of claims A37 to A59 the preceding claims, wherein the machine learning technique is a neural network comprising at least one recurrent layer.

A61. A method according to claim A60, wherein the at least one recurrent layer is a bidirectional recurrent layer.

A62. A method according to claim A60 or A61, wherein the neural network applies a global normalization of the weight distributions over all paths of labels through the series of weight distributions.

A63. A method according to any one of claims A60 to A62, wherein the neural network includes at least one convolutional layer arranged before the at least one recurrent layer and which performs a convolution of windowed sections of the signal.

A64. A method according to any one of claims A37 to A63, wherein the weights represent posterior probabilities.

A65. A method according to any one of claims A37 to A64, wherein the step of deriving an estimate of the series of polymer units from the weight distributions is performed using connectionist temporal classification.

A66. A method according to any one of claims A37 to A65, wherein the step of deriving an estimate of a polymer unit from the weight distributions comprises deriving a label in respect of respective weight distribution and run-length compressing the derived labels.

A67. A method according to any one of claims A37 to A59, wherein the step of deriving an estimate of the series of polymer units from the weight distributions comprises estimating the most likely path of labels through the series of weight distributions on the basis of the weight distributions, and deriving the estimate of the series of polymer units from the path of labels estimated as most likely.

A68. A method according to any one of claims A37 to A63, wherein the step of deriving an estimate of the series of polymer units from the weight distributions comprises estimating the labels that are most likely in respect of each weight distribution, taking into account forwards and backwards paths of labels through the series of weight distributions, and deriving the estimate of the series of polymer units from the labels estimated as most likely.

A69. A method according to any one of claims A37 to A59, wherein the nanopore is a protein pore.

A70. A method according to any one of claims A37 to A69, wherein the polymer is a polynucleotide, and the polymer units are nucleotides.

A71. A method according to any one of claims A37 to A70, wherein the signal is derived from measurements of one or more of the following properties: ionic current, impedance, a tunnelling property, a field effect transistor voltage and an optical property.

A72. A method according to any one of claims A37 to A71, the method being performed in a computer apparatus.

A73. A method according to any one of claims A37 to A72, further comprising deriving the signal from the polymer during translocation of the polymer with respect to a nanopore.

A74. A method according to any one of claims A13 to A15, wherein the weight distributions comprise further weights over possible lengths of consecutive instances of the same type of polymer unit (a) for possible pairs of the type of the given polymer unit and the type of the preceding polymer unit, (b) for possible pairs of the type of the given polymer unit and the type of the following polymer unit, or (c) for possible triplets of the type of the given polymer unit, the type of the preceding polymer unit, and the type of the following polymer unit.

Having thus described several aspects of at least one embodiment of this invention, it is to be appreciated that various alterations, modifications, and improvements will readily occur to those skilled in the art.

Such alterations, modifications, and improvements are intended to be part of this disclosure, and are intended to be within the spirit and scope of the invention. Further, though advantages of the present invention are indicated, it should be appreciated that not every embodiment of the technology described herein will include every described advantage. Some embodiments may not implement any features described as advantageous herein and in some instances one or more of the described features may be implemented to achieve further embodiments. Accordingly, the foregoing description and drawings are by way of example only.

The above-described embodiments of the technology described herein can be implemented in any of numerous ways. For example, the embodiments may be implemented using hardware, software or a combination thereof. When implemented in software, the software code can be executed on any suitable processor or collection of processors, whether provided in a single computer or distributed among multiple computers. Such processors may be implemented as integrated circuits, with one or more processors in an integrated circuit component, including commercially available integrated circuit components known in the art by names such as CPU chips, GPU chips, microprocessor, microcontroller, or co-processor. Alternatively, a processor may be implemented in custom circuitry, such as an ASIC, or semi-custom circuitry resulting from configuring a programmable logic device. As yet a further alternative, a processor may be a portion of a larger circuit or semiconductor device, whether commercially available, semi-custom or custom. As a specific example, some commercially available microprocessors have multiple cores such that one or a subset of those cores may constitute a processor. Though, a processor may be implemented using circuitry in any suitable format.

Various aspects of the present invention may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Also, the invention may be embodied as a method, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Further, some actions are described as taken by a "user." It should be appreciated that a "user" need not be a single individual, and that in some embodiments, actions attributable to a "user" may be performed by a team of individuals and/or an individual in combination with computer-assisted tools or other mechanisms.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

The terms "approximately" and "about" may be used to mean within ±20% of a target value in some embodiments, within ±10% of a target value in some embodiments, within ±5% of a target value in some embodiments, and yet within ±2% of a target value in some embodiments. The terms "approximately" and "about" may include the target value. The term "substantially equal" may be used to refer to values that are within ±20% of one another in some embodiments, within ±10% of one another in some embodiments, within ±5% of one another in some embodiments, and yet within ±2% of one another in some embodiments.

The term "substantially" may be used to refer to values that are within ±20% of a comparative measure in some embodiments, within ±10% in some embodiments, within ±5% in some embodiments, and yet within ±2% in some embodiments. For example, a first direction that is "substantially" perpendicular to a second direction may refer to a first direction that is within ±20% of making a 90° angle with the second direction in some embodiments, within ±10% of making a 90° angle with the second direction in some embodiments, within ±5% of making a 90° angle with the second direction in some embodiments, and yet within ±2% of making a 90° angle with the second direction in some embodiments.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

What is claimed is:

1. A method of high rate sequencing of polymers using a nanopore measurement and analysis system, the method comprising:

placing a polymer into the nanopore measurement and analysis system; and sequencing the polymer using the nanopore measurement and analysis system at least in part by:

translocating at least a portion of the polymer through a nanopore of the nanopore measurement and analysis system at a sequencing rate in the range of 10-1000 polymer units per second, wherein the sequencing rate comprises a rate at which the polymer translocates through the nanopore;

measuring, using the nanopore measurement and analysis system and at a sampling rate between 100 Hz and 30 KHz, electrical signals generated by the translocating of the polymer through the nanopore, wherein the sampling rate is greater than or equal to the sequencing rate;

generating a time-ordered series of measurements based on the measuring of the electrical signals generated by the translocating;

organizing the time-ordered series of measurements into a plurality of overlapping subsets of measurements;

generating a plurality of feature vectors from the plurality of overlapping subsets of measurements by processing the subsets of measurements using a convolutional neural network;

generating a plurality of sets of transition weights from the plurality of feature vectors using a recurrent neural network;

generating, using the plurality of sets of transition weights, a Hidden Markov Model (HMM);

determining, using the HMM, an estimate of a sequence of polymer units in the polymer; and outputting the estimated sequence of polymer units, wherein the recurrent neural network comprises a bidirectional recurrent layer, the bidirectional recurrent layer comprising:

a first unidirectional recurrent layer comprising a first plurality of long short-term memory (LSTM) units connected in a first direction; and a second unidirectional recurrent layer comprising a second plurality of LSTM units connected in a second direction, opposite the first direction, wherein outputs of the first unidirectional recurrent layer are inputs into the second unidirectional recurrent layer, wherein generating the plurality of sets of transition weights comprises:
updating state vectors of multiple LSTM units in the first unidirectional recurrent layer based on the feature vectors and state vectors of LSTM units preceding the multiple LSTM units in the first unidirectional recurrent layer; and
updating state vectors of multiple LSTM units in the second unidirectional recurrent layer based on outputs of the first unidirectional recurrent layer and state vectors of LSTM units preceding the multiple LSTM units in the second unidirectional recurrent layer; and
wherein each weight of a particular set of transition weights of the plurality of sets of transition weights is associated with respective first and second labels and is indicative of the likelihood that a transition between a polymer unit having the first label and a polymer unit having the second label occurred within a measurement period represented by a subset of measurements, of the plurality of overlapping subsets, associated with the particular set of transition weights.

2. The method of claim 1, wherein a number of the measurements in a subset of the plurality of subsets of the time-ordered series of measurements is different than a number of a plurality of values of the feature vector.

3. The method of claim 1,
wherein each of the polymer units in the polymer is one of a finite, known group of polymer units, the group of polymer units consisting of N distinct polymer units,
wherein each of the first label and second label is one of a finite, known, group of labels, the group of labels consisting of M distinct labels, and
wherein M is greater than N.

4. The method of claim 3, wherein a set of the plurality of sets of weights consists of $M^2$ weights.

5. The method of claim 3, wherein M is equal to N+1, and wherein the group of labels consists of N labels each corresponding to respective ones of the group of polymer units, and a single label corresponding to a blank label, which represents a lack of a transition within the measurement period represented by an associated subset of the plurality of overlapping subsets of the time-ordered series of measurements.

6. The method of claim 3, wherein M is equal to 2×N, and wherein the group of labels consists of N labels each corresponding to a first instance of respective ones of the group of polymer units, and N labels each corresponding to a second instance of the respective ones of the group of polymer units.

7. The method of claim 1,
wherein generating the HMM comprises determining emission and transition probabilities of the HMM using weights of the plurality of sets of weights; and
wherein determining the estimate of the sequence of polymer units comprises determining, using the HMM, a most likely sequence of polymer units within the polymer.

8. The method of claim 7,
wherein each of the first label and second label is one of a finite, known, group of labels, and
wherein determining the most likely sequence of polymer units within the polymer comprises determining the most likely sequence of labels of the group of labels using the HMM, and identifying polymer units that correspond to the labels of the group of labels.

9. The method of claim 1, further comprising measuring a current through the nanopore during translocation of the polymer through the nanopore, thereby generating a current measurement signal.

10. The method of claim 9, further comprising digitizing the current measurement signal, thereby producing the time-ordered series of measurements.

11. The method of claim 1, wherein:
each of the polymer units in the polymer is one of a finite, known group of polymer units,
each polymer unit of the finite, known group of polymer units has a respective primary label and a respective secondary label, and
transitions, within the plurality of sets of transition weights, from any first label to a second label corresponding to the primary label of a particular polymer unit are allowed, and transitions, within the plurality of sets of transition weights, to any second label corresponding the secondary label of the particular polymer are only allowed from a first label corresponding to the primary or secondary label of the particular polymer unit.

12. The method of claim 1, wherein the sampling rate is between one and ten times the sequencing rate.

13. A system for high rate sequencing of polymers, the system comprising:
a nanopore measurement and analysis system comprising:
a nanopore;
one or more processors; and
at least one non-transitory computer readable medium storing instructions;
wherein the nanopore measurement and analysis system is configured to sequence a polymer at least in part by:
translocating at least a portion of the polymer through the nanopore at a sequencing rate in the range of 10-1000 polymer units per second, wherein the sequencing rate comprises a rate at which the polymer translocates through the nanopore;
measuring, at a sampling rate between 100 Hz and 30Khz, electrical signals generated by the translocating of the polymer through the nanopore, wherein the sampling rate is greater than or equal to the sequencing rate;
generating a time-ordered series of measurements from electrical signals generated by the translocating of the polymer through the nanopore;
performing, by executing the instructions stored on the at least one non-transitory medium with the one or more processors:
organizing the time-ordered series of measurements into a plurality of overlapping subsets of measurements;
generating a plurality of feature vectors from the plurality of overlapping subsets of measurements by processing the subsets of measurements using a convolutional neural network;
generating a plurality of sets of transition weights from the plurality of feature vectors using a recurrent neural network;
generating, using the plurality of sets of transition weights, a Hidden Markov Model (HMM); and
determining, using the HMM, using the one or more processors, an estimate of the sequence of polymer units in the polymer; and outputting the estimated sequence of polymer units,
wherein the recurrent neural network comprises a bidirectional recurrent layer, the bidirectional recurrent layer comprising:
a first unidirectional recurrent layer comprising a first plurality of long short-term memory (LSTM) units connected in a first direction; and
a second unidirectional recurrent layer comprising a second plurality of LSTM units connected in a second direction, opposite the first direction, wherein outputs of the first unidirectional recurrent layer are inputs into the second unidirectional recurrent layer;
wherein generating the plurality of sets of transition weights comprises:
updating state vectors of multiple LSTM units in the first unidirectional recurrent layer based on the feature vectors and state vectors of LSTM units preceding the multiple LSTM units in the first unidirectional recurrent layer; and
updating state vectors of multiple LSTM units in the second unidirectional recurrent layer based on outputs of the first unidirectional recurrent layer and state vectors of LSTM units preceding the multiple LSTM units in the second unidirectional recurrent layer; and
wherein each weight of a particular set of transition weights of the plurality of sets of transition weights is associated with respective first and second labels and is indicative of the likelihood that a transition between a polymer unit having the first label and a polymer unit having the second label occurred within a measurement period represented by a subset of measurements, of the plurality of overlapping subsets, associated with the particular set of transition weights.

14. The system of claim 13, wherein a number of the measurements in a subset of the plurality of overlapping subsets of the time-ordered series of measurements is different than a number of a plurality of values of the feature vector.

15. The system of claim 13,
wherein each of the polymer units in the polymer is one of a finite, known group of polymer units, the group of polymer units consisting of N distinct polymer units,
wherein each of the first label and second label is one of a finite, known, group of labels, the group of labels consisting of M distinct labels, and
wherein M is greater than N.

16. The system of claim 15, wherein a set of the plurality of sets of weights consists of $M^2$ weights.

17. The system of claim 15, wherein M is equal to N+1, and wherein the group of labels consists of N labels each corresponding to respective ones of the group of polymer units, and a single label corresponding to a blank label, which represents a lack of a transition within the measurement period represented by an associated subset of the plurality of overlapping subsets of the time-ordered series of measurements.

18. The system of claim 15, wherein M is equal to 2×N, and wherein the group of labels consists of N labels each corresponding to a first instance of respective ones of the group of polymer units, and N labels each corresponding to a second instance of the respective ones of the group of polymer units.

19. The system of claim 13,
wherein generating the HMM comprises determining emission and transition probabilities of the HMM using weights of the plurality of sets of weights; and
wherein determining the estimate of the sequence of polymer units comprises determining, using the HMM, a most likely sequence of polymer units within the polymer.

20. The system of claim 19,
wherein each of the first label and second label is one of a finite, known, group of labels, and
wherein determining the most likely sequence of polymer units within the polymer comprises determining the most likely sequence of labels of the group of labels using the HMM, and identifying polymer units that correspond to the labels of the group of labels.

21. The system of claim 13, further comprising a measurement unit configured to measure a current through the nanopore during translocation of the polymer through the nanopore, thereby generating a current measurement signal.

22. The system of claim 21, wherein the measurement unit is further configured to digitize the current measurement signal, thereby producing the time-ordered series of measurements, and to provide the time-ordered series of measurements to the analysis unit.

23. The system of claim 13, wherein:
each of the polymer units in the polymer is one of a finite, known group of polymer units,
each polymer unit of the finite, known group of polymer units has a respective primary label and a respective secondary label, and
transitions, within the plurality of sets of transition weights, from any first label to a second label corresponding to the primary label of a particular polymer unit are allowed, and transitions, within the plurality of sets of transition weights, to any second label corresponding the secondary label of the particular polymer are only allowed from a first label corresponding to the primary or secondary label of the particular polymer unit.

24. The system of claim 13, wherein the sampling rate is between one and ten times the sequencing rate.

* * * * *